United States Patent
Peyman

(10) Patent No.: US 10,022,457 B2
(45) Date of Patent: *Jul. 17, 2018

(54) METHODS TO REGULATE POLARIZATION AND ENHANCE FUNCTION OF CELLS

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,323

(22) Filed: Jun. 17, 2015

(65) Prior Publication Data

US 2015/0283265 A1  Oct. 8, 2015

Related U.S. Application Data

(63) Continuation-in-part of application No. 14/635,595, filed on Mar. 2, 2015, which is a continuation-in-part of application No. 14/591,158, filed on Jan. 7, 2015, which is a continuation-in-part of application No. 14/444,668, filed on Jul. 28, 2014, which is a continuation-in-part of application No. 14/160,174, filed on Jan. 21, 2014, which is a continuation-in-part of application No. 14/069,965, filed on Nov. 1, 2013, which is a continuation-in-part of application No. 13/952,875, filed on Jul. 29, 2013, which is a continuation-in-part of application No. 13/772,150, filed on Feb. 20, 2013, now Pat. No. 8,562,660, which is a continuation-in-part of application No. 13/367,984, filed on Feb. 7, 2012, now Pat. No. 8,460,351, which is a continuation-in-part of application No. 13/088,730, filed on Apr. 18, 2011, now Pat. No. 8,409,263, which is a continuation-in-part of application No. 11/197,869, filed on Aug. 5, 2005, now Pat. No. 8,388,668.

(51) Int. Cl.

| A61K 48/00 | (2006.01) |
|---|---|
| A61K 38/46 | (2006.01) |
| A61N 5/06 | (2006.01) |
| A61K 9/00 | (2006.01) |
| A61K 41/00 | (2006.01) |
| A61K 45/06 | (2006.01) |
| A61K 49/00 | (2006.01) |
| A61K 31/7105 | (2006.01) |
| A61K 31/713 | (2006.01) |
| A61K 47/48 | (2006.01) |
| A61N 5/067 | (2006.01) |
| A61B 5/00 | (2006.01) |
| A61B 5/04 | (2006.01) |
| A61B 5/11 | (2006.01) |
| A61F 9/007 | (2006.01) |
| A61F 9/008 | (2006.01) |
| B82Y 5/00 | (2011.01) |
| B82Y 30/00 | (2011.01) |
| A61B 17/00 | (2006.01) |

(52) U.S. Cl.
CPC ........ *A61K 48/0041* (2013.01); *A61K 9/0009* (2013.01); *A61K 31/713* (2013.01); *A61K 31/7105* (2013.01); *A61K 38/465* (2013.01); *A61K 41/0042* (2013.01); *A61K 45/06* (2013.01); *A61K 47/48861* (2013.01); *A61K 47/48884* (2013.01); *A61K 49/0067* (2013.01); *A61N 5/0601* (2013.01); *A61N 5/062* (2013.01); *A61N 5/0613* (2013.01); *A61N 5/0622* (2013.01); *A61B 5/04001* (2013.01); *A61B 5/1114* (2013.01); *A61B 5/6867* (2013.01); *A61B 2017/00345* (2013.01); *A61F 9/008* (2013.01); *A61F 9/0079* (2013.01); *A61N 2005/063* (2013.01); *A61N 2005/067* (2013.01); *A61N 2005/0651* (2013.01); *A61N 2005/0659* (2013.01); *A61N 2005/0661* (2013.01); *A61N 2005/0662* (2013.01); *B82Y 5/00* (2013.01); *B82Y 30/00* (2013.01)

(58) Field of Classification Search
None
See application file for complete search history.

(56) References Cited

U.S. PATENT DOCUMENTS

| 5,118,666 A | 6/1992 | Habener |
|---|---|---|
| 5,220,181 A | 6/1993 | Kanal et al. |
| 5,545,618 A | 8/1996 | Buckley et al. |
| 6,552,053 B2 | 4/2003 | Sun et al. |
| 6,566,595 B2 | 5/2003 | Suzuki et al. |
| 6,583,111 B1 | 6/2003 | DiMarchi et al. |
| 6,641,553 B1 | 11/2003 | Chee et al. |
| 8,324,344 B2 | 12/2012 | Kisiel |

(Continued)

OTHER PUBLICATIONS

Canillas et al., Boletin de la Sociedad Española de Cerámica y Vidrio, 2014, 53: 249-259.*

(Continued)

*Primary Examiner* — Ileana Popa
(74) *Attorney, Agent, or Firm* — The Law Office of Patrick F. O'Reilly III, LLC

(57) ABSTRACT

Methods and compositions to controllably regulate cells at a target site. A quantum dot-targeting agent complex is administered to a patient in need of therapy, and the complex is stimulated using an implanted fiber optic system. In embodiments, the system includes an electrical sensor that detects and monitors electrical activity of the stimulated controllably regulated cells, and relays this information to a controller that can regulate further stimulation.

17 Claims, 4 Drawing Sheets

(56) References Cited

U.S. PATENT DOCUMENTS

| | | | |
|---|---|---|---|
| 2003/0014089 | A1 | 1/2003 | Chow et al. |
| 2003/0022374 | A1 | 1/2003 | Greenbaum et al. |
| 2004/0003839 | A1 | 1/2004 | Curtain |
| 2005/0004625 | A1 | 1/2005 | Chow |
| 2006/0173362 | A1 | 8/2006 | Toms et al. |
| 2010/0185260 | A1 | 7/2010 | Olson |
| 2010/0211146 | A1 | 8/2010 | Strowbridge et al. |
| 2011/0021970 | A1* | 1/2011 | Vo-Dinh ............ A61K 49/0039 604/20 |
| 2011/0270153 | A1 | 11/2011 | Olson |
| 2012/0121712 | A1* | 5/2012 | Ciofani .................. A61N 1/205 424/490 |
| 2014/0148880 | A1* | 5/2014 | Deisseroth ......... A61K 41/0038 607/100 |
| 2014/0324134 | A1* | 10/2014 | Klapoetke ............ C07K 14/405 607/88 |

OTHER PUBLICATIONS

Graves, Q J Med, 2006, 99: 201-217.*
Ousterout et al., Nature Commun., Feb. 18, 2015, 6: 1-13.*
Krook-Magnuson et al., Nature Communications, 2013, 4: 1-8.*
Sahai et al., International Conference of Space Optical Systems and Applications, 2011: 164-170.*
Qi et al., Nano Letters, 2011, 11: 1331-1336.*
Benabid, Current Opinion in Neurobiology, 2003, 13: 696-706.*
U.S. Appl. No. 14/635,595, filed Mar. 2, 2015.
U.S. Appl. No. 14/591,158, filed Jan. 7, 2015.
U.S. Appl. No. 14/444,668, filed Jul. 28, 2014.
U.S. Appl. No. 14/160,174, filed Jan. 21, 2014.
U.S. Appl. No. 14/069,965, filed Nov. 1, 2013.
U.S. Appl. No. 13/952,875, filed Jul. 29, 2013.
U.S. Appl. No. 13/772,150, filed Feb. 20, 2013, now U.S. Pat. No. 8,562,660.
U.S. Appl. No. 13/367,984, filed Feb. 7, 2012, now U.S. Pat. No. 8,460,351.
U.S. Appl. No. 13/088,730, filed Apr. 18, 2011, now U.S. Pat. No. 8,409,263.
U.S. Appl. No. 11/197,869, filed Aug. 5, 2005, now U.S. Pat. No. 8,388,668.
Bakalova et al., "Quantum Dot-Conjugated Hybridization Probes for Preliminary Screening of siRNA Sequences" J. Am. Chem. Soc., (2005), 127 (32), pp. 11328-11335.
Derfus et al. "Targeted Quantum Dot Conjugates for siRNA Delivery" Bioconjugate Chem.,vol. 18, No. 5 (2007) pp. 1391-1396.
Deisseroth "Optogenetics" Nature Methods, Published online Dec. 20, 2010, available at http://www.stanford.edu/group/dlab/papers/deisserothnature2010.pdf.
Dixit et al. "Quantum Dot Encapsulation in Viral Capsids" Nano Letters, vol. 6, No. 9 (2006), pp. 1993-1999.
Ebenstein et al. "Combining atomic force and fluorescence microscopy for analysis of quantum-dot labeled protein—DNA complexes" J. Molecular Recognition, vol. 22, issue 5 (2009), pp. 397-402.
Gill et al. " Fluorescence Resonance Energy Transfer in CdSe/ZnS—DNA Conjugates: Probing Hybridization and DNA Cleavage" J. Phys. Chem. B, vol. 109, (2005), pp. 23715-23719.
Joo et al. "Enhanced Real-Time Monitoring of Adeno-Associated Virus Trafficking by Virus—Quantum Dot Conjugates" ACS Nano, vol. 5, No. 5 (2011), pp. 3523-3535.
Lim et al. "Specific Nucleic Acid Detection Using Photophysical Properties of Quantum Dot Probes" Anal. Chem., vol. 82, No. 3 (2010), 886-891.
Mossman "Quantum dots track who gets into cell nucleus" Physorg.com, Sep. 2, 2010, available at http://www.physorg.com/news202628740.html.
Wang et al. Nucleic Acid Conjugated Nanomaterials for Enhanced Molecular Recognition. ACS Nano 3 (2009) 2451-2460.
You et al. "Incorporation of quantum dots on virus in polycationic solution" Int. J. Nanomedicine, vol. 1, No. 1 (2006), pp. 59-64.
Anscombe "Quantum Dots: Small Structures Poised to Break Big" Photonics Spectra, Jul. 2005, pp. 94-96.
Mali et al. "Intravitreous Injection of a Membrane Depolarization Agent Causes Retinal Degeneration Via Matrix Metalloproteinase-9" Investigative Ophthalmology and Visual Science, vol. 46, No. 6 (2005), pp. 2125-2132.
Greenbaum et al. "Application of Photosynthesis to Artificial Sight" paper presented at the Nanoscale Science and Technology in Medicine Symposium, 23rd International Conference of the IEEE Engineering in Medicine and Biology Society, Oct. 25-28, 2001, Istanbul, Turkey, vol. 4, pp. 4089-4091.
Aylott "Optical nanosensors—an enabling technology for intracellular measurements" Analyst, vol. 128 (2003), pp. 309-312.
Buck et al. " Optochemical nanosensor PEBBLEs: photonic explorers for bioanalysis with biologically localized embedding" Current Opinion in Chemical Biology, vol. 8 (2004), pp. 540-546.
Fehr et al. "Development and use of fluorescent nanosensors for metabolite imaging in living cells" Biochemical Society Transactions, vol. 23, part 1 (2005), pp. 287-290.
Ferreira et al. "Downstream processing of plasmid DNA for gene therapy and DNA vaccine applications," Tibtech, vol. 18 (2000), pp. 380-387.
Fei et al. "Glucose nanosensors based on redox polymer/glucose oxidase modified carbon fiber nanoelectrodes" Talanta, vol. 65 (2005), pp. 918-924.
Haes et al. "A unified view of propagating and localized surface plasmon resonance biosensors" Anal. Bioanal. Chem, vol. 379 (2004), pp. 920-930.
Cullum et al. "The development of optical nanosensors for biological measurements" Tibtech, vol. 18 (2000), pp. 388-393.
Hauser and Zhang, "Peptides as biological semiconductors," Nature, vol. 468 (2010), p. 516.
Audero et al. Sporadic Autonomic Dysregulation and Death Associated with Excessive Serotonin Autoinhibition. Science, vol. 321 (2008), pp. 130-133.
De Crespigny et al. Magnetic Resonance Imaging Assessment of Cerebral Hemodynamics During Spreading Depression in Rats. Journal of Cerebral Blood Flow and Metabolism, vol. 18 (1998), pp. 1008-1017.
Höhne et al. Acetazolamide prevents hypoxic pulmonary vasoconstriction in conscious dogs. J. Appl. Physiol. vol. 97 (2004), pp. 515-521.
Rio-Portilla et al. REM Sleep POST-EYE Movement Activation. International Journal of Bioelectromagnetism, vol. 10, No. 4 (2008), pp. 192-208.
IBM Press Release, Made in IBM Labs: IBM Scientists Demonstrate World's Fastest Graphene Transistor, Feburary 5, 2010, 1 page.
Kurzwiel AI, Engineers envision 2-dimensional grapheme metamaterials and 1-atom-thick optical devices. Jun. 10, 2011, 1 page.
Erogbogbo et al. Plasmonic gold and luminescent silicon nanoplatforms for multimode imaging of cancer cells. Integr. Biol. 5 (2013) 144-150.
Yezhelyev et al., Proton-Sponge-Coated Quantum Dots for siRNA Delivery and Intracellular Imaging. J Am. Chem. Soc. 130 (2008) 9006-9012.
Rajan and Raj. Potential Drug Delivery Applications of Chitosan Based Nanomaterials. I.Re.Ch.E. 5 (2013) 145-155.
Song et al., Tumor Cell Targeting Using Folate-Conjugated Fluorescent Quantum Dots and Receptor-Mediated Endocytosis. Clinical Chemistry 55 (2009) 955-963.
Liu et al. Bioconjugated Pluroinc Triblock-Copolymer Micelle-Encapsulated Quantum Dots for Targeted Imaging of Cancer: In Vitro and In Vivo Studies. Theranostics 2 (2012) 705-713.
Jin et al. Preparation and Characterization of Highly Fluorescent, Glutathione-coated Infrared Quantum Dots for in Vivo Fluorescence Imaging. Int. J. Mol. Sci. 9 (2008) 20440-2061.

(56) References Cited

OTHER PUBLICATIONS

Liu et al., Endocytic Trafficking of Nanoparticles Delivered by Cell-penetrating Peptides Comprised of Nona-arginine and a Penetration Accelerating Sequence, PLOS One 8 (2013) e67100, 12 pages.
Liu et al., Intracellular Delivery of Nanoparticles and DNAs by IR9 Cell-penetrating Peptides, PLOS One 8 (2013) e64205 (13 pages).
Liu et al., Cell-Penetrating Peptide-Functionalized Quantum Dots for Intracellular Delivery. J. Nanosci. Nanotechnol. 10 (2010) 7897-7905.
Liu et al., Cellular Internalization of Quantum Dots Noncovalently Conjugated with Arginine-Rich Cell-Penetrating Peptides. J. Nanosci. Nanotechnol. 10 (2010) 6534-6543.
Xu et al., Nona-Arginine Facilitates Delivery of Quantum Dots into Cells via Multiple Pathways. J. Biomedicine and Biotechnology 2010, Article ID 948543, 11 pages.
Delehanty et al., Self-Assembled Quantum Dot-Peptide Bioconjugates for Selective Intracellular Delivery. Bioconjug Chem 17 (2006) 920-927.
Narayanan et al., Mimicking cellular transport mechanism in stem cells through endosomal escape of new peptide-coated quantum dots. Scientific Reports 3, article No. 2184, 6 pages.
Ho et al., Combining QD-FRET and Microfluidics to Monitor DNA Nanocomplex Self-Assembly in Real-Time. J. Vis Exp. 30 (2009) 1432, 3 pages.
Biju et al., Delivering quantum dots to cells: bioconjugated quantum dots for targeted and nonspecific extracellular and intracellular imaging. Chem. Soc. Rev. 39 (2010) 3031-3056.
Algar and Krull. Toward a Multiplexed Solid-Phase Nucleic Acid Hybridization Assay Using Quantum Dots as Donors in Fluorescence Resonance Energy Transfer. Anal Chem. 81 (2009) 4113-4120.
Gao et al. In vivo cancer targeting and imaging with semiconductor quantum dots. Nature Biotechnology 22 (2004) 969-976.
Gussin et al. Binding of Muscimol-Conjugated Quantum Dots to $Gaba_c$ Receptors. J. Am Chem. Soc. 128 (2006) 15701-15713.
He et al. Highly Luminescent Water-Dispersible Silicon Nanowires for Long Term Immunofluorescent Cellular Imaging. Angew. Chern. Int. Ed. 50 (2011) 3080-3083.
Heiss et al. Image-guided convection-enhanced delivery of muscimol to the primate brain. J Neurosurg. 112 (2010) 790-795.
Lugo et al. Remote switching of cellular activity and cell signaling using light in conjunction with quantum dots. Biomedical Optics Express 3. (2012) 447-454.
Pappas et al. Nanoscale Engineering of a Cellular Interface with Semiconductor Nanoparticle Films for Photoelectric Stimulation of Neurons. Nano Letters 7 (2007) 513-519.
Rosenthal et al. Biocompatible Quantum Dots for Biological Applications. Chem Biol. 18 (2011) 10-24.
Templeton. Tiny Q-dots may enable more precise brain surgery. Pittsburgh Post-Gazette, Apr. 10, 2007, 4 pages.
van Rooy et al. Comparison of five different targeting ligands to enhance accumulation of liposomes into the brain. Journal of Controlled Release 150 (2011) 30-36.
Wen et al. Theranostic liposomes loaded with quantum dots and apomorphine for brain targeting and bioimaging. International Journal of Nanomedicine 7 (2012) 1599-1611.
Zhong et al. Modular design of an ultrahigh-intensity nanoparticle probe for cancer cell imaging and rapid visual detection of nucleic acids. Chem Commun., 48 (2012) 6277-6279.
Baker and Baker. Luminescent Carbon Nanodots: Emergent Nanolights. Angew. Chem. Int. Ed. 49 (2010) 6726-6744.
Hofmann-Amtenbrink et al. Superparamagnetic nanoparticles for biomedical applications. Nanostructured Materials for Biomedical Applications, (ed. M.C. Tan.) 2009, chap. 5, 119-149.
Joeres et al. Quantitative Comparison of Optical Coherence Tomography after Pegaptanib or Bevacizumab in Neovascular Age-Related Macular Degeneration. Ophthalmology 115 (2008) 347-354.
Min et al. Lentivirus-Mediated sFlt-I Gene Fragment Transfer Suppresses Retinal Neovascularization. Current Eye Research 34 (2009) 401-410.
Mulder et al. Quantum dots for multimodal molecular imaging of angiogenesis. Angiogenesis 13 (2010) 131-134.
Singerman. Combination therapy using the small interfering RNA bevasiranib. Retina 2009, Abstract Only.
Smith et al., Bioconjugated Quantum Dots for In Vivo Molecular and Cellular Imaging. Adv. Drug Deliv. Rev. 60 (2008) 1226-1240.
You et al. Incorporation of quantum dots on virus in polycationic solution. Int. J. Nanomedicine 1 (2006) 59-64.
Lee et al. The retinoblastoma susceptibility gene encodes a nuclear phosphoprotein associated with DNA binding activity. Nature, 329(1987) 642-645.
Tomczak et al. Designer polymer-quantum dot architectures. Progress in Polymer Science, 34 (2009) 393-430.
Duan and Nle. Cell-penetrating quantum dots based on multivalent and endosome-disrupting surface coatings. J. Am. Chem. Soc. 129 (2007) 3333-3338.
Kim and Taton. Multicomponent nanoparticles via self-assembly with cross-linked block copolymer surfactants. Langmuir, 23 (2007) 2198-2202.
Pan et al. Silica Cross-linked Micelles Loading with Silicon Nanoparticles: Preparation and Characterization. ACS Appl. Mater. Interfaces 5 (2013) 7042-7049.
Lv et al., Surface modification of quantum dots and magnetic nanoparticles with PEG-conjugated chitosan derivatives for biological applications. Chemical Papers 67 (2013) 1404-1413.
Suzuki et al. Quantum Dot FRET Biosensors that Respond to pH, to Proteolytic or Nucleolytic Cleavage, to DNA Synthesis, or to a Multiplexing Combination. J. Am. Chem. Soc. 130 (2008) 5720-5725.
Huang et al. Intermolecular and Intramolecular Quencher Based Quantum Dot Nanoprobes for Multiplexed Detection of Endonuclease Activity and Inhibition, Anal. Chem. 83 (2011) 8913-8918.
Akbarzadeh et al. Liposome: classification, preparation, and applications. Nanoscale Research Letters 8:102 (2013) 1-9.
Sander et al. CRISPR-Cas systems for editing, regulating and targeting genomes. Nature Biotechnology 32:4 (2014) 347-355.

* cited by examiner

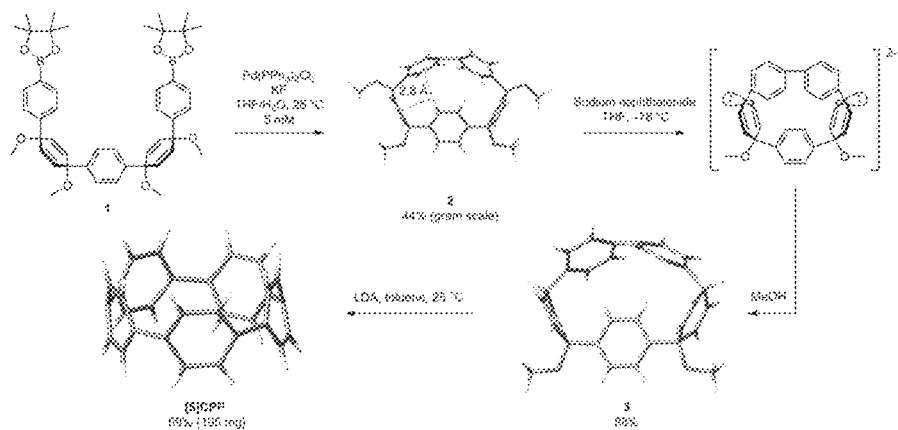
FIG. 6
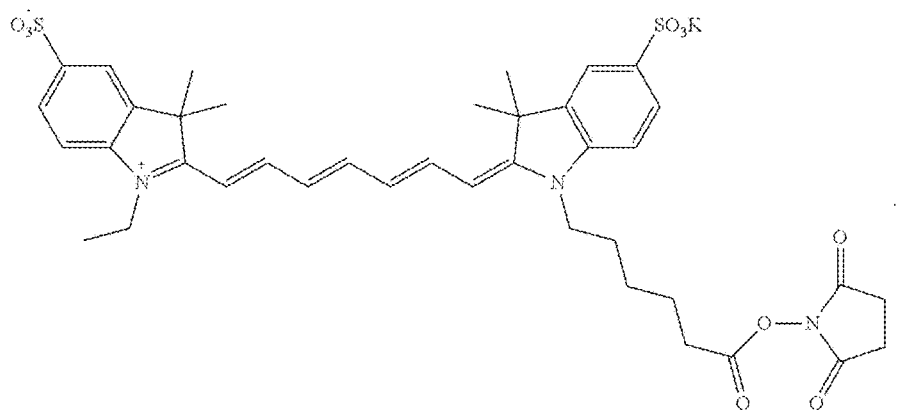
FIG. 7                                Cy7-NHS

METHODS TO REGULATE POLARIZATION AND ENHANCE FUNCTION OF CELLS

This application is a Continuation-In-Part of co-pending application U.S. Ser. No. 14/635,595 filed Mar. 2, 2015; which is a Continuation-In-Part of U.S. Ser. No. 14/591,158 filed Jan. 7, 2015; which is a Continuation-In-Part of co-pending application U.S. Ser. No. 14/069,965 filed Nov. 1, 2013; which is a Continuation-In-Part of co-pending application U.S. Ser. No. 13/952,875 filed Jul. 29, 2013; which is a Continuation-In-Part of U.S. Ser. No. 13/772,150 filed Feb. 20, 2013 now U.S. Pat. No. 8,562,660; which is a Continuation-In-Part of U.S. Ser. No. 13/367,984 filed Feb. 7, 2012 now U.S. Pat. No. 8,460,351; which is a Continuation-In-Part of application Ser. No. 13/088,730 filed Apr. 18, 2011 now U.S. Pat. No. 8,409,263; which is a Continuation-In-Part of application Ser. No. 11/197,869 filed Aug. 5, 2005 now U.S. Pat. No. 8,388,668; each of which is expressly incorporated by reference herein in its entirety.

FIELD OF THE INVENTION

The invention relates to delivery of combined methods to regulate polarization and enhance function of cells.

BRIEF DESCRIPTION OF THE DRAWINGS

FIG. 6 schematically shows synthesis of a cell-penetrating peptide (CPP).

FIG. 7 shows the chemical structure of an activated fluorescent dye.

SUMMARY

Figure 1:
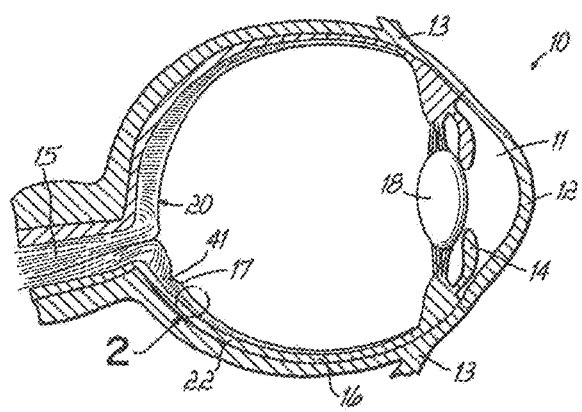
FIG. 1 is a drawing of a longitudinal section of a human eye.

A method to enhance functional recovery of a cell in a patient in need thereof by administering graphene quantum dots, graphene-oxide quantum dots, graphene-zinc oxide quantum dots, graphene nanotubes, and/or carbon nanotubes, collectively termed nanoparticles, to a site in a patient where functional cell recovery is needed. The nanoparticles at the site are controllably activated by light, thus controllably altering a cellular electrical property. Activation uses an internal device of a fiber optic comprising wires and a tip containing a light source, a sensor connectable to the fiber optic wires, and a controller to receive and generate electrical signals. Signals resulting from the altered cellular electrical property at the site are sensed and are optionally provided to a processor to monitor and/or controllably alter the electrical property using the controller. The processor may be implanted in the patient, e.g. under the skin, or may be external to the patient.

In one embodiment the sensor is an implanted graphene ribbon or nanoribbon, a wafer-scale epithaxically grown graphene on the surface of at least a portion of the fiber optic, acting as a transistor providing feedback to the controller, to which it is operatively connected, on the altered cellular electrical property. That is, the sensor monitors target cell electrical conditions and provides these to the controller, which in turn can modify control of the light based on the electrical conditions.

The light source may be a light emitting diode (LED) with a rechargeable battery. Ambient light, ultraviolet light, infrared light, or visible light may be used, and light exposure intensity and/or duration may be controlled. In one embodiment the nanoparticles are injected locally immediately prior to placement of the device through a cannula guided with magnetic resonance imaging (MRI).

The method may be used with neurons, muscle cells cardiac cells, ocular cells, etc.; on any cell that would benefit from such therapy. As an example, one candidate is a patient with a neural-related pathology, a neurodegenerative disease or symptom of such a disease, or blindness, and/or surgically injured neurons (e.g., patients after LASIK surgery and during LASIK surgery, prior to closing the corneal flap). Such patients include those with epilepsy, Parkinson's disease, Alzheimer's disease, depression, spinal cord injury, peripheral nerve injury, stroke, and chronic pain. The nanoparticles may be targeted or provided at a site of brain injury or spinal cord injury to controllably enhance neuronal growth. In one embodiment the nanoparticles contain other agents to facilitate neuronal growth, e.g., myelin basic protein (MBP), valproic acid, ketamine, donepezil hydrochloride, thymosin β10, thymosin α1, choline acetyl esterase, nerve growth factor (NGF), and/or brain derived growth factor (BDGF). As another example, one candidate is a patient with cardiac dysrhythmia, with the nanoparticles provided and controllably activated to control heart rate. Other agents may be included, e.g., stem cells, immunomodulators, anti-vascular endothelial growth factor (VEGF) agents, anti-integrin agents, anti-inflammatory agents, antibiotics, anti-viral agents, anti-fungal agents, anti-proliferative agents, and/or anti-cancer agents, also agents to enhance or impart biocompatibility.

One embodiment is a method for delivering an opsin family gene to an anatomical and/or physiological site for stimulating, modifying polarization of, and/or inducing an action potential in a cell at the site. This embodiment administers a complex comprising a non-quantum dot nanoparticle carrier, a biocompatible molecule for cell uptake of the complex, an opsin family gene, a biocompatible fluid to the anatomical and/or physiological site, to result in formation of a light activated channel in a cell membrane permitting cell stimulation by an external or internal light transmitted by a fiber optic to modify polarization of, and/or induce an action potential in the cell at the site. Optional components include a targeting moiety such as an antibody, antigen, ligand, receptor, etc., and/or a second gene.

Examples of non-quantum dot nanoparticles include fullerenes, buckyballs, dendrimers, liposomes, aptamers, and/or micelles. Such non-quantum dot nanoparticles are known in the art, as only one non-limiting example, dendrimers include poly(amidoamine) (PAMAM), poly(amidoamine-organosilicon) (PAMAMOS), poly(propyleneimine) (PPIO), tecto, multilingual, chiral, hybrid, amphiphilic, micellar, multiple antipen peptide, and Frechet-type dendrimers. The nanoparticle can be functionalized to render or enhance its biocompatibility, and can be further treated or delivered to enhance cell penetration. To enhance biocompatibility, association with or covalent coupling to one or more of cell penetrating peptides (CPP), arginine-CPP, cysteine-CPP, polyethylene glycol (PEG), biotin-streptavadin, acetyl cysteine, an antibody, and/or a ligand for a receptor may be employed.

Opsin family gene members include rhodopsin, halorhodopsin, photopsin, and channelrhodopsin. The second gene is used where the patient has a genetic or acquired degenerative disease or condition, where the second gene ameliorates at least to some extent the disease or condition by providing the component that is lacking, by enhancing gene activity, by silencing gene activity, etc., as known in the art. Examples include a degenerative retinal condition, a degenerative central nervous system disease, and a degenerative cardiovascular disease. The second gene may encode a protein, or it may be an inhibitory RNA (RNAi) for gene silencing.

The method may be used on an excitable cell, such as a retinal cell, a cardiac cell, a muscle cell, a central nervous system cell (CNS), a spinal cord cell, and/or a peripheral nerve cell. The method may also be used on a non-excitable cell, such as a fibroblast, a glial cell, a stem cell, and/or a pluripotential mesenchymal stem cell.

Light-induced cell stimulation may induce cell proliferation, which desirably replaces cell loss due to various diseases or conditions at the targeted site. Examples of such conditions include, but are not limited to, age related macular degeneration, stoke, and ischemia.

The complex may be administered by an injection at an intraocular, intravitreal, intraretinal, subretinal, or intrathecal location. Its entry or penetration into the target cell may be enhanced by electroporation or mechanical force. In one example, the complex is injected in a desired location with an insulated metallic needle connected to a power source for electroporation delivery of the complex inside the cell.

The complex may further contain a therapeutic agent, e.g., immunomodulators, anti-VEGF agents, anti-integrins, anti-inflammatory agents, antibiotics, anti-viral agents, anti-fungal agents, anti-proliferative agents, and/or anti-cancer agents.

One embodiment is a method for providing a gene to a target cell by administering to a patient in need thereof a plurality of nanoparticles, the nanoparticles comprising either a plasmid or a liposome containing at least one G-protein and/or opsin-family gene and an antibody that targets the nanoparticles to a cell and coated with a biocompatible molecule for cell uptake, forming a complex of nanoparticle-plasmid-gene or the nanoparticle-lipsosome-gene, respectively, then stimulating the complex with an energy source under conditions sufficient to introduce the gene into the target cell. In this embodiment is plasmid or liposome is attached to the nanoparticles during a process of coating the nanoparticles with at least one PEG, PEI, chitosan, biotin, streptavidin, CPP, and/or ACPP. The gene may be rhodopsin, holorodopsin, Go opsins, Gq opsins, photoisomerases, and/or neuropsins, may include DNA, RNA, and/or siRNA. The result is regulated membrane potential of the cells, induced action potential of the cells, and/or transmission of a signal from the cell to a second cell. Administration may be systemic or local, and optionally includes administration of at least one medicament. Local administration may be to the eye, central nervous system, peripheral nerves, and/or heart. In this embodiment, the complex is protected from degradation by the blood brain barrier and/or blood ocular barrier. Administration may also be through the nasal mucosal by spraying, drops, or injection to access olfactory nerves and hence providing the complex to brain. For the method in general as described in this embodiment, the patient in need thereof may have, e.g., epilepsy, a mood disorder, post-traumatic stress disorder (PTSD), depression, fright, Parkinsons disease, Alzheimers disease, a brain degenerative diseases, trauma, stroke, migraine headache, and/or an addiction. In one specific embodiment of the general embodiment, the complex is prepared in tissue culture of a cell type, e.g., neuronal, retinal, muscle, neurons, ocular cell, glial cell, and stem cell of any preceding cell type, prior to administering the complex to the patient. Stimulation of the complex may be by any of the following sources: visible light, ultraviolet light, infrared light, diode laser, ultrasound energy, and/or mechanical force. In a specific embodiment of the general embodiment, stimulation is by a processor as a light pulse applied to a site, e.g., the transfected organ, the heart as a pacemaker using a fiber optic implanted in the organ, externally for superficially located nerves, to the retina through the cornea or directly through the sclera, and/or to the brain through the nasal mucosa, where the processor optionally regulates the pulse number and/or duration. Application of light pulses to the transfected cells desirably causes an increase in the number of transfected cells in vivo or in vitro. Nanoparticles may be of any shape: e.g., spheres, nanotubes, nanowires, tetragons, hexagons, and/or cylinders. After cell transfection, the nanoparticles are removed by, e.g., cell expulsion, reticuloendothelial cell uptake, elimination in bile, elimination in sweat, elimination in urine, elimination in feces, etc. A specific embodiment also enhances tolerance of the nanoparticles in vivo. In this specific embodiment, the patient in need of treatment is administered magnetic nanoparticles, the magnetic nanoparticles excluding quantum dots, the nanoparticles comprising a plasmid or liposome containing at least one G-protein and/or opsin-family gene and an antibody that targets the nanoparticles to a cell and coated with a biocompatible molecule for cell uptake, forming a complex of nanoparticle-plasmid-gene. The complex is activated with an energy source. A localized magnet is applied, resulting in formation of a magnetic field at the complex site, with an electrostatic potential of the nanoparticles up to −25 mV. This magnetic field enhances penetration and tranfection of the gene into the cell. The method results in enhanced tolerance of the nanoparticles in vivo compared to quantum dots. In use, the complex is administered and a magnet is positioned at the desired transfection site to generate a magnetic field and attract the nanoparticles to the site. Administration may be, e.g., in the circulation, eye, CNS, peripheral nerves, and/or heart, and the magnet may be positioned, e.g., over the sclera behind the retina, frontal, parietal, posterior cortex, heart, spinal cord, peripheral nerves, and/or nose.

One embodiment is a method for editing and/or regulating a gene in a target excitable cell. The method administers to a patient nanoparticles that are coated with a biocompatible molecule for cell uptake, and conjugated with one or more opsin-family genes, an antibody that targets the nanoparticles to an excitable cell, and a CRISPR/cas9 complex, forming a complex of coated nanoparticle-gene-CRISPR/cas9. The complex is stimulated with an energy source under conditions sufficient to introduce the gene into the target cell and, using the CRISPR/cas9 complex, to modify a pathology-inducing DNA, either nuclear DNA or mitochondrial DNA, in the cell to treat the patient. The CRISPR/cas9 complex excises a DNA segment bearing a pathology-inducing mutation in the opsin-family gene, and may also replace it with an unmutated DNA segment in the opsin-family gene. The excitable cell may be, e.g., a retinal cell, a central nervous system neuronal cell, a central nervous system glial cell, a spinal cord cell, a peripheral nerve cell, and/or a cardiac cell. The complex may be administered systemically or locally, e.g., intraocular, intravitreal, intrathecal, brain ventricle, over a brain, proximate a central nervous system neuron, proximate a peripheral nerve, and/or intracardiac. The patient may have a neurodegenerative disease or a cardiac rhythm disease.

In one example of this embodiment, the complex is injected into an excitable organ with a brain blood barrier, resulting in complex entry into the organ in the absence of degradation by enzymes in the blood.

In one example of this embodiment, before administering the complex of coated nanoparticle-gene-CRISPR/cas9 to the patient, the complex is administered to in vitro cultured patient stem cells, e.g., conjunctival limbal stem cells, heart stem cells, brain stem cells, spinal cord nerve stem cells, mesenchymal stem cells, ectodermal stem cells, etc.

In one example of this embodiment, the nanoparticles are piezoelectric nanoparticles and the stimulating step is controlled remotely to wirelessly stimulate, e.g., by an ultrasound probe, the piezoelectric nanoparticles and produce an electrical current created by a wireless electrical stimulation of cells, resulting in an altered membrane potential, i.e., hyperpolarization, hypopolarization, or depolarization, or an altered action potential of cells in contact with the piezoelectric nanoparticles. The piezoelectric nanoparticles may be administered by injecting submucosally and/or spraying a nasal mucosa to travel through olfactory nerves to the brain, and the brain stimulated with an externally applied ultrasound over the nose by a patient as needed. Piezoelectric nanoparticles can be rendered biocompatible by coating with zirconate titanate, perovskite-based, oxides, barium titanate, polyvinylidene fluoride (PVDF), etc. The piezoelectric nanoparticles may be controlled by a diode laser surgically implanted in the patient, with the piezoelectric nanoparticles acting as an "on"/"off" switch of a battery supplying electricity to the diode laser. Stimulation is controlled by a programmable processor of an extra-corporal ultrasonic probe wirelessly controlled by the diode laser, which is implanted, e.g., external to the skull, internal to the skull, adjacent to an organ, adjacent to sympathetic ganglion cells, adjacent to parasympathetic ganglions cells, adjacent to the brain, adjacent to the heart, adjacent to an eye, adjacent to the spinal cord, adjacent to peripheral nerves, etc. In this example, the patient can be treated for epilepsy, migraine, depression, paresis, paralysis, spastic muscles numbness, nerve injuries, dementia, spinal cord injury, peripheral nerve injury, Parkinson's disease, Alzheimer's disease, restless leg syndrome, etc.

A ribbon of piezoelectric nanoparticles may be attached to the battery of the diode that, upon ultrasound stimulation, creates a pulsating electrical current in the piezoelectric nanoparticles leading to the battery of the diode laser, thus controlling activation of the diode laser light production and initiating an "on"/"off" action potential in the membrane of excitable cells depending on the frequency and duration of the electrical pulse.

These and other embodiments are further described below.

DETAILED DESCRIPTION

Combination mechanisms to correct, reduce, and/or prevent physiological electro-sensory damage or electromotor damage and promote functional recovery of excitable cells, e.g., neurons in the central nervous system (i.e., brain and spinal cord) and neuronal cells involved with visual, auditory, vocal, olfactory responses, e.g., retinal cells in the eye, cochlear cells in the ear, olfactory cells in the nose, etc., and neurons in the peripheral nervous system are provided. The inventive combination methods can be thought of as akin to combination approaches in treating neoplastic lesions, but targeting less than optimally-functioning excitable cells. The combination mechanism may also be used to correct, reduce, and/or prevent damage to tissues by rendering normally non-excitable cells in proximity to partially or wholly non-functional cells artificially functional.

In one embodiment, the combined method promotes functional recovery and controllably regulates plasma membrane polarization of a functional excitable neuronal cell. A biomolecule effecting gene therapy is administered into an eye and/or central nervous system of a patient in need of the therapy (e.g., a patient with a neuronal disease). Quantum dots and/or semiconductor nanowires (generically referred to hereafter as particles or solar cells) are administered into the eye and/or central nervous system of the patient, either simultaneously or sequentially either before or after the biomolecule is administered. Quantum dots are nanoparticulate semiconductors in which excitation is confined in all three spatial dimensions. Semiconductor nanowires are microparticulate semiconductors in which excitation is confined in two of the three spatial dimensions, with a nanoscale diameter but a length to width ratio of 100:1 or more. Semiconductor nanowires tend to be more efficient than quantum dots in converting electromagnetic radiation into electrical charge and more similar to solar cells in creating electromagnetic fields when stimulated by such radiation. In one embodiment, the particle comprises both a semiconductor and a metal, or two semiconductors, thus creating a hetero-junction, which together act as a photodiode. The difference in the chemical potentials of the two components, e.g., the semi-conductor and the metal, bends the energy bands of the semiconductor near the junction, creating a built-in electrical field. In one embodiment, the hetero-junction creates a Schottky junction, where illumination creates electron-hole pairs that separate under the influence of the built-in field, thereby yielding a photovoltage across the structure, e.g., the photovoltaic, or PV effect. Light is applied to the eye or central nervous system to controllably activate the particles by controlling exposure time, exposure intensity, exposure site, etc. to controllably regulate the plasma membrane polarization of the functional excitable neuronal cells and to provide the biomolecule to the neuronal cells. In one embodiment, the biomolecule is directly or indirectly associated with, or covalently conjugated to, the quantum dots and/or semiconductor nanowires so that in a single administration (e.g., one injection), both biomolecule and quantum dots components are provided to the patient. Once administered, the quantum dots can be imaged, tracked, monitoring, evaluated in the patient using a sensor or other tracking agent using methods well known in the art (e.g., digital imaging, etc.).

The light sensitive particles may be provided to specific neurons for therapy. As one example, they may be provided to an optic nerve for retinal therapy. As another example, they may be provided to an olfactory nerve for nasal nerve therapy, and/or as an point of entry for brain therapy, etc. As another example, they may be provided to selective or non-selective sites for selective stimulation of various regions, either alone or in combination. As non-limiting examples of selective stimulation of central nervous system nerves, the visual cortex can be stimulated through specific light stimulation of the retina, the olfactory neuron can be stimulated by smell, the auditory neuron can be stimulation by sound, etc. As non-limiting examples of selective stimulation of peripheral nervous system nerves, chronic pain may be controlled by direct stimulation of the appropriate nerves, and appetite may be suppressed by direct stimulation of appropriate nerves.

Stimulation by light may be achieved by several mechanisms, as known to one skilled in the art. For example, using activation of particles in the brain as an exemplary, non-limiting example, activation may be provided by a fiber optic device surgically placed at the desired area of the brain, located under the scalp, and illuminated by a light source, e.g., a light emitting diode (LED) through a small window made in the skull replaced by clear glass at a desired area. Such a window may remain hidden under the skin, because it is known that light can penetrate a few millimeters into skin. An analogous concept may be used for stimulating other areas of the central nervous system, the peripheral nervous system, or heart or other muscles, with or without application of a fiber optic device if quantum dots are injected through an opening into the superficial area of the brain, nerve, heart muscle, etc. Such stimulation may controllably regulate, i.e., activate/deactivate, by using an appropriate wavelength of light, with or without a processor with the specific neuronal code as pulses. Quantum dots and/or semiconductor nanowires may be used in conjunction with stem cell therapy or in conjunction with other devices, e.g., prosthetic devices, that are activated or otherwise rely or light and/or electrical current.

In addition to using the method for the above indications and for treatment of retinal degeneration, etc. and posttraumatic epilepsy, the method also has applications in amelioration of the underlying pathology and/or symptoms of genetic and/or degenerative diseases, e.g., retinitis pigmentosa, retinal degeneration, central nervous system pathologies such as Alzheimer's disease and Parkinson disease, dopamine-regulated disorders such as migraines, autism, mood disorders, schizophrenia, senile dementia, sleep disorders, restless leg syndrome, and depression. Tourette syndrome, restless leg syndrome, and stuttering are a part of the same spectrum of diseases characterized by malfunctioning membrane potential and electrical pulse transmission. The consequences of infectious diseases, epilepsy, paralysis, and traumatic injury of the brain and/or peripheral nerves are also amenable to therapy with the inventive method. All such disorders can be influenced either with particle administration alone or with particles associated with medication modifying cell membrane potential, e.g., carbonic anhydrase inhibitors. Amelioration includes any reduction in the signs, symptoms, and/or etiology, including but not limited to prevention, therapy, and curative effects, of any of the above indications. As one example, quantum dots and/or semiconductor nanowires may be targeted to dopamine-regulated nerves for therapy of migraines, mood disorders, etc. As another example, quantum dots and/or semiconductor nanowires can be used for deep subthalamic, cerebral, or cortical and peripheral nerve stimulation for therapy of Parkinson's disease, etc.

A viral vector (e.g., adenovirus, adeno-associated virus, retrovirus) can provide the biomolecule, which can be a natural or synthetic protein, peptide, nucleic acid, oligonucleotide, gene, etc. when conjugated with the particles. In one embodiment, the biomolecule is a cell membrane ion channel protein such as rhodopsin, halorhodopsin, or other light-activated membrane ion channel protein. If the same wavelength of light stimulates both quantum dots and protein (or other biomolecule), the effect may be complementary and the result is an enhanced action potential in the excitable cells, i.e., this embodiment achieves a synergistic effect. If a different wavelength of light stimulates the quantum dots and protein (or other biomolecule), the result is a subsequent action potential in the excitable cells, i.e., this embodiment achieves silencing of the action potential in the cell. In one embodiment, the biomolecule, e.g., membrane channel protein, is excited by the same wavelengths of light that also excite the particles. In one embodiment, the biomolecule, e.g., membrane channel protein, is excited by a different wavelength of light than that exciting the particles, and then in turn its electrical field opens the membrane channel protein. The variations can increase or reduce or suppress the action potential in the cell. In all cases, the "tunable" selection of the biomolecule and the particles, as well as the specific excitation energy (typically light but also ultrasound radiation energy can be used) applied, provides a controlled and regulated process. In turn, the selective on or off activation of the particles provides the high degree of control that enhances efficacy and safety and permits close monitoring and regulation.

Delivery and intercellular and/or intracellular and/or intramembrane localization of nano- and micro-particle solar cells within and/or among excitable biological cells to regulate membrane polarization of biological cells combined with other methods to promote functional recovery of damaged excitable cells in the eye and central nervous system. The inventive method provides solar cells in a minimally invasive procedure into the eye, heart, and/or the central nervous system; the solar cells are not implanted in the body in an invasive procedure. The inventive method provides a plurality of solar cells as discrete individual particles; the solar cells are not connected as a unit and do not have a backing layer or backing material. The inventive method uses solar cells that may be activated by ambient light; the method does not use an electrical apparatus and thus does not use photodiodes, stimulating electrodes, or other electrical devices. The inventive method uses solar cells to enhance the regulation of polarization by the excitable biological cells themselves; the solar cells facilitate or boost the ability of excitable biological cells to normalize or regulate their own polarity. In one embodiment, the inventive method provides for excitable biological cells to regulate their own polarity; stimulation of the solar cells used in the invention does not generate an action potential to regulate polarity, but instead facilitates the biological cells themselves to regulate polarity. In one embodiment, the inventive method provides for stimulation of the solar cells used in the invention to generate an action potential. The inventive method provides semiconductor particles in combination with therapies to enhance functional recovery of neuronal cells damaged by different etiologies, including genetic disorders, ischemic or vascular damage, and age-related damage. By combining modulation of cell polarization, which takes advantage of the ability to regulate quantum dots and/or semiconductor nanowires, with genetic and other approaches to therapy, neuronal degenerative process are ameliorated.

Biological cells are bound by a plasma membrane. In all cells, this membrane has a resting potential. The resting potential is an electrical charge across the plasma membrane of the non-excited or resting cell, rendering the interior of the cell negative with respect to the exterior. Hence, the plasma membrane of all biological cells in their resting state is polarized.

The extent of the resting potential varies among different cell types. In cells such as nerve, muscle, and retinal cells, which are excitable in that they can be stimulated to create an electric current, the resting potential is about −70 millivolts (my). This resting potential arises from two components of the plasma membrane: the sodium/potassium ATPase, which pumps two potassium ions ($K^+$) into the cell for every three sodium ions ($Na^+$) it pumps out of the cell, and "leakiness" of some $K^+$ channels, allowing slow facilitated diffusion of $K^+$ out of the cell. The result is a net loss of positive charge from within the resting cell.

Certain external stimuli reduce the charge across the plasma membrane, resulting in membrane depolarization. As one example, mechanical stimuli (e.g., stretching, sound waves) activate mechanically-gated $Na^+$ channels. As another example, certain neurotransmitters (e.g., acetylcholine) open ligand-gated $Na^+$ channels. In each case, the facilitated diffusion of $Na^+$ into the cell depolarizes the membrane; it reduces the resting potential at that membrane location. This creates an excitatory postsynaptic potential (EPSP).

If the potential at any membrane location is reduced to the threshold voltage, many voltage-gated $Na^+$ channels open in that location, generating an influx of $Na^+$. This localized, sudden, complete depolarization opens adjacent voltage-gated $Na^+$ channels. The result is a wave of depolarization along the cell membrane, referred to as the action potential or, in excitable cells, an impulse.

A second stimulus applied to an excitable cell within a short time (less than 0.001 second) after the first stimulus will not trigger another impulse. This is because the membrane is depolarized, leaving the cell in a refractory period. Only when the −70 my polarity is reestablished, termed repolarization, will an excitable cell be able to respond to another stimulus. Repolarization is established by facilitated diffusion of $K^+$ out of the cell. When the cell is finally rested, $Na^+$ that entered the cell at each impulse are actively transported back out of the cell.

Hyperpolarization occurs when negatively charged chloride ions ($Cl^-$) enter the cell and $K^+$ exit the cell. Some neurotransmitters may facilitate this by opening $Cl^-$ and/or $K^+$ channels in the plasma membrane. Hyperpolarization results in an inhibitory postsynaptic potential (IPSP); although the threshold voltage of the cell is unchanged, it requires a stronger excitatory stimulus to reach threshold.

Abnormal cell polarization may affect regenerative and/or functional process of excitable cells, and result in cell dysfunction. Abnormal cell polarization includes, but is not limited to, any of the following and whether transient or sustained: loss of polarization, decreased polarization, altered polarization, hyperpolarization, and any deviation from normal cell polarization. Excitable cells include, but are not limited to, sensory cells (e.g., retina and macula of the eye), neuronal cells in the central nervous system (CNS) (brain and spinal cord) and peripheral nervous system, muscle cells (striated, cardiac, and smooth muscle cells).

The orientation of the cell with respect to its apical, lateral, and basal surfaces may affect polarization and may be regulated by the inventive method. Adjacent cells communicate in the lateral domain, with attachment or contact sites by which cells adhere to one another. Terminal bars, attachment sites between cells that act as a barrier to passage of substances, are located around the entire circumference of cells and are composed of junctional complexes responsible for joining individual cells. Occluding junctions, also referred to as tight junctions or zonula occludentes, are located apically within the lateral domain and encircle the cell, separating the luminal region from the intercellular space and cytoplasm. These are narrow regions of contact between the plasma membranes of adjacent cells and seal off the intercellular space, forming an impermeable diffusion barrier between cells and preventing proteins from migrating between apical and lateral surfaces of the cell. In one embodiment, the method selectively regulates polarization in areas of the cell bound by occluding junctions. Particles may be selectively positioned and/or selectively regulated to regulate polarization at a desired site.

Ischemic cell death is caused by failure of the ionic pumps of the plasma membrane. Depolarization of the plasma membrane in retinal cells and subsequent synaptic release of L-glutamate are implicated in ischemic retinal damage. Mali et al. (Investigative Ophthalmology and Visual Science, 2005, 46, 2125) reported that when KCl, a known membrane depolarizing agent, is injected into the vitreous humor, the subsequent membrane depolarization results in a dose- and time-related upregulation of matrix metalloproteinase (MMP)-9 activity and protein in the retina. This was associated with an increase in proapoptotic protein Bax and apoptotic death of cells in the ganglion cell layer and inner nuclear layer, and subsequent loss of NF-L-positive ganglion cells and calretinin-positive amacrine cells. A synthetic MMP inhibitor inhibited KCl-mediated MMP-9 upregulation, which led to a significant attenuation of KCl-induced retinal damage. Regulating polarization thus inhibits MMP-9 and decreases damage that can diminish visual acuity.

Methods to regulate membrane polarization of excitable cells assist in minimizing physiologic damage and reducing pathology including but not limited to ischemic damage to the retina, degenerative diseases of the retina including but not limited to retinitis pigmentosa, ischemic and/or degenerative diseases of cardiac muscle, and/or ischemic and degenerative diseases of cerebral tissue, etc. In turn, the method minimizes or prevents undesirable effects such as loss of visual acuity, myocardial infarction, cerebral stroke, etc. and enhances a patient's quality of life.

Methods to regulate membrane polarization of cells may also be used to create analogs to excitable cells from target cells that under normal physiologic conditions do not respond to the same stimuli. This embodiment beneficially preserves at least partial, if not substantially complete or complete, function of the overall tissue. For example, because particles such as quantum dots and/or semiconductor nanowires can be inserted into cell membranes and/or pass through cell membranes, the particles and/or nanowires can convert target cells that normally lack significant levels of rhodopsin, e.g., mesenchymal cells, glial cells, etc., into cells that are able to respond to certain wavelengths of light through hypo- or hyperpolarization. In one embodiment, the particles and/or nanowires may be conjugated with agents that stimulate or suppress the production of light-stimulated cell membrane ion channel proteins to influence the target cell's response to light. In one embodiment the agent is a gene encoding a channelrhodopsin protein. In one embodiment the particles and/or nanowire may be conjugated with agents such as nucleic acids or oligonucleotides that direct production of membrane ion channel proteins to make target cells excitable by stimuli such as wavelengths of light (e.g., retinal cells), mechanical vibration (e.g., cochlear cells), small molecules (e.g., olfactory cells), etc. In one embodiment the nucleic acids or oligonucleotides are regulatory sequences that stimulate transcription of genes encoding such regulatory proteins. In one embodiment the nucleic acids or oligonucleotides are sequences that encode such proteins.

Methods to regulate membrane polarization may also be used to modify stem cells for transplantation within patient tissue. Autologous stem cells treated with particles and/or nanowires may be cultured and used to repopulate cells lost or destroyed in degenerative diseases of the retina, brain, heart, etc., with therapeutic stimulation of the particles used to counteract or delay the effects of the underlying disease process. As previously described, modulation of cell plasma membrane polarization may minimize physiologic damage and reduce pathology in the repopulated cells.

In one embodiment autologous stem cells treated with particles conjugated with genes and/or gene therapy vectors may be used to both deliver gene therapy and label the modified stem cells. After providing to patient tissues, the quantum dots and/or semiconductor nanowires may be imaged, tracked, monitored, regulated, and evaluated in the patient for cell survival and maturation rates, treatment efficacy, etc. In one embodiment the particles and/or nanowire may be adapted to respond to electromagnetic radiation by emitting fluorescence radiation and the distribution and/or state of the nanoparticles and/or nanowires may be evaluated using a fluorescence microscope emitting the appropriate wavelength of light to activate the particles. In one embodiment autologous stem cells treated with particles linked to magnetic nanoparticles may be used to both label stem cells and provide directional bias to the cells. The particles and/or nanowires and magnetic nanoparticles may be conjugated with natural or synthetic biomolecules, e.g., proteins, peptides, nucleic acids, oligonucleotides, etc., that bind to specific locations in and/or on a cell and, after administration to a patient, may be subjected to a magnetic field applied outside the tissue, e.g., by permanent magnets temporarily affixed to the body in proximity to the eye, brain, heart, etc., to provide a predetermined directionality to the cells through attraction to the magnetic field. The particles may be made biocompatible by coating them with a biocompatible polymer such as (poly)ethylene glycol (PEG) moieties. Various biomolecules may be conjugated to one or the other or both of the particles and linked magnetic nanoparticles to cause them to bind to different locations in and/or on the treated cells.

In one embodiment, the nanoparticles, such as a semiconductor-metal particle, can be coated such that the nanoparticle is amphiphilic, where a portion of the nanoparticle is rendered hydrophilic and another portion of the nanoparticle is rendered hydrophobic. In one embodiment, and using a CdSe/Au particle as an example, the CdSe/Au particles are covered by trioctylphosphine oxide and alkylphosphonic acid, both of which are hydrophobic. Surface functionalization covers the Au portion of the CdSe/Au particles with polyethylene glycol, making them hydrophilic; the CdSe portion, still covered by trioctylphosphine oxide and alkyl phosphonic acid, remains hydrophobic. In one embodiment, CdSe/Au particles are suspended in N,N-dimethylformamide containing detergent (e.g., 1% Triton X-100) and exposed to polyethylene glycol-$(CH_2)_{10}$—SH to coordinate the thiol to the Au end.

Such amphiphilic particles may be inserting into cell membranes with the hydrophobic portion of the particle embedded within the cell membrane and the hydrophilic portion of the particle exposed to the intracellular and/or extracellular space. Alternatively, the hydrophobic portion may associate with the inner and/or outer surface of the cell membrane. In embodiments, the amphiphilic particles may be incorporated into micelles or liposomes, using methods known in the art, and the particle-containing liposome or micelle can be administered to a patient. After incorporation of amphiphilic particles into a bilayer membrane of a liposome, assimilation of the liposome into a cell membrane delivers the particle into the membrane, with the hydrophobic portion immersed in the lipid portion of the membrane, and the hydrophilic extending into the aqueous phase. The liposome or micelle may contain additional biomolecules, e.g., targeting moieties such as antibodies, cell surface receptors, etc., as well as additional therapeutic agents.

The inventive method may be more fully appreciated with respect to its utility in a single organ, such as the eye. One skilled in the art will realize, however, that it is not so limited and is applicable to other cells.

In one embodiment, the inventive method externally administers to a patient a composition or, alternatively a device in a biocompatible composition, comprising particles and/or nanowires or solar cells to stimulate the cell membranes from inside of the cell or outside of the cell or within the cell membrane of all retinal cells. In one embodiment, the quantum dots and/or semiconductor nanowires injected into the eye and are delivered to the retinal cell cytoplasm or nucleus or cell membrane. In one embodiment, the quantum dots and/or semiconductor nanowires injected into the eye and are delivered into the cell membrane of retinal ganglion cells. In one embodiment, the quantum dots and/or semiconductor nanowires are introduced into the central nervous system. In one embodiment, the quantum dots and/or semiconductor nanowires are conjugated or otherwise associated with proteins or other moieties and provided using a vector to a patient to effect functional recovery of neuronal cells. One non-limiting example of this embodiment is quantum dots conjugated with a channel proteins introduced via a viral vector (e.g., adeno-associated virus (AAV)) to effect retinal gene therapy. Such a vector and/or quantum dots can be labeled for visualization, tracking, sensing, etc. For example, the quantum dots can be labeled or tagged with a signal recognition moiety. Such a vector can incorporate quantum dots into the viral capsid using, e.g., (poly)ethylene glycol (PEG) moieties. Another non-limiting example is the use and selective regulation, selective activation/deactivation alone or in combination, to monitor interfering RNA (RNAi) delivery and regulate gene silencing. Another non-limiting example is the use of quantum dots for in situ visualization of gene expression. This may be performed using quantum dot-DNA-coated polymer. Semiconductor nanowires may be used in place of or in addition to quantum dots in each of these examples. Combinations of these embodiments are contemplated and included, using methods known by one skilled in the art and as subsequently described.

As used herein, particles, quantum dots, and solar cells are used synonymously.

The retinal cells comprise at least ganglion cells, glial cells, photoreceptor cells, Muller cells, bipolar cells, horizontal cells, microglial cells, and cells of the neural fibers, etc. The amount of stimulation, or degree of membrane stimulation, can be regulated by the amount of energy provided by the particles. The total amount of energy provided by the particles to transmit to the membrane depends upon the time of particle activation.

The particles are activated by the energy source; the response to the specific wavelength depends on the inner material building the inner semiconductor. The energy source to activate the particles provides ambient light, ultraviolet light, visible light, infrared light, or ultrasound radiation. In one embodiment, the particles respond to blue, red, green, or IR light. In one embodiment, a plurality of particles respond to various specific wavelengths. In one embodiment, the particles have multiple semiconductor cores, and thus respond to various wavelengths. The wavelength selections are photons with different energies. The particles must have energy bandgaps or energy statues that match the energy of the photons. One skilled in the art tunes the energy levels using materials with different band-gaps or by carefully selecting the quantum size as it effects the energy level. Thus, one uses different size particles and/or particles with different cores. In one embodiment, the activation time interval ranges from 1 nanosecond to 100 nanoseconds. In one embodiment, the activation time interval ranges from 1 second to 100 seconds.

The source of energy activates the particles for the particles to provide sufficient energy to activate the membrane. In one embodiment, the energy source sufficient to activate the particles ranges from about one picojoule to one microjoule. In one embodiment, the activation energy source is external ambient light. In one embodiment, the activation energy source is a diode, LED, etc. Other activation energy sources are possible, as known by one skilled in the art. The energy source provides electromagnetic radiation, as known to one skilled in the art. Electromagnetic radiation includes infrared radiation (700 nm to 1 mm), visible light (380 nm to 760 nm), and ultraviolet radiation (4 nm to 400 nm). The energy source is varied to vary the response of the particles; as one skilled in the art is aware, the shorter the wavelength, the more energy is delivered. As an example, infrared wavelengths (thermal activation), visible and ultraviolet wavelengths are provided for activating the particles to produce the desired photovoltaic (energy) response from the particle by a separate energy source or one that can provide combinations of the required wavelength ranges. The energy source(s) may be externally programmed (such as by computer software) to produce different wavelengths resulting in photovoltaic responses at desired time intervals. The regulation or control of the timed production of generated photovoltaic responses from the particles can be used to control the regulation of cell membrane potentials. The energy input from the energy source may be varied to vary the particles responses, hence regulating and/or controlling the membrane potential. The particles respond to the specific wavelength(s) to which they are exposed. A specific coating to the particles renders them specific. The protein coating can direct them to attach to certain cell membranes, and/or to enter a cell such as a normal cell, a tumor cell, a nerve cell, a glial cell, The particles, albeit relatively non-selective, can potentially increase the membrane potential of any cells to which they come into contact. After exposure to light, a diode, etc. they emit an electrical potential, current, or fluorescence. The electrical potential generated by this exposure to radiation increases the cell membrane potential. In an example of a specific application, a particle may be adapted to bind a photoreceptor of the eye and to trigger a hyperpolarization of the photoreceptor in response to activation by infrared light. The administration of such a particle may enable a patient to visually perceive at least some sources of infrared radiation, i.e., to have a 'night vision'-like visual perception.

FIG. 1 shows a mammalian eye 10. The structures and locations of the anterior chamber 11, cornea 12, conjunctiva 13, iris 14, optic nerve 15, sclera 16, macula lutea or macula 17, lens 18, retina 20, choroid 22, and fovea 41 are indicated. The macula is located in the center of the posterior part of the retina 20 and is the most sensitive portion of the retina. It is an oval region of about 3 mm by 5 mm, in the center of which is a depression, the fovea centralis 41, from which rods are absent. Inside the fovea 41 is the point of entrance of the optic nerve 15 and its central artery. At this point, the retina 20 is incomplete and forms the blind spot.

Figure 2:
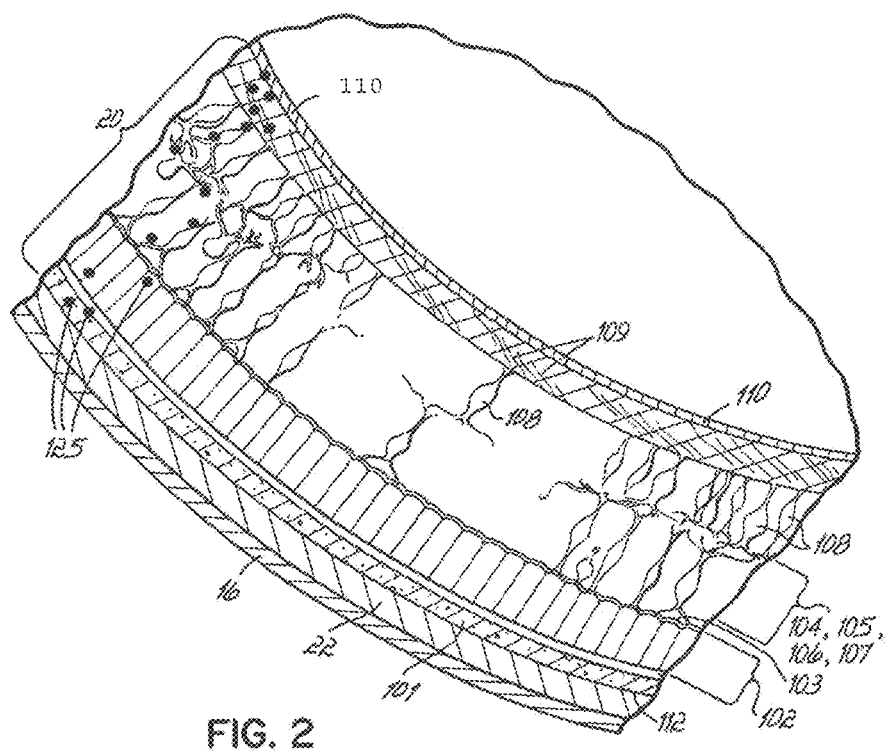
FIG. 2 is an enlarged diagrammatic illustration of the circled area 2 of FIG. 1 showing detailed retinal structures.

The encircled area 2 of FIG. 1 is shown in exploded form in FIG. 2. As shown in FIG. 2, the retina 20 forms the innermost layer of the posterior portion of the eye and is the photoreceptor organ. The retina 20 has an optical portion that lines the inner surface of the choroid 22 and extends from the papilla of the optic nerve 15 to the ora serrata 21 anteriorly. At the papilla, where the retina 20 stops, and at the ora serrata 21, the retina 20 is firmly connected with the retinal pigment epithelium (RPE) 101.

The retina 20 has ten parallel layers. These are, from the choroid in, as follows: the RPE 101, photoreceptor cells (rod and cone inner and outer segments) 102, the external limiting membrane 103, the outer nuclear layer 104, the outer plexiform layer 105, the inner nuclear layer 106, the inner plexiform layer 107, the layer of ganglion cells 108, the layer of optic nerve fibers or neurofiber layer 109, and the internal limiting membrane 110. The internal limiting membrane 110 is very thin (less than 5 µm), and normally adheres with the neurofiber layer 109 of the ganglion cells 108.

The pigment epithelial cell layer or RPE 101 rests on a basal lamina termed Bruch's membrane 112 that is adjacent to the choroid 22.

The next three layers are composed of various portions of one cell type, termed the first neuron. These layers are the photoreceptor region (lamina) 102 of rods and cones, the external limiting membrane 103, and the outer nuclear layer 104 composed of the nuclei of the rods and cones cells. The rods have long, thin bodies, and the cones have a broad base. The rods have greater sensitivity for low light levels; the cones have better visual acuity in daylight and are also responsible for color perception. There are three types of cones, each absorbing light from a different portion of the visible spectrum: long-wavelength (red), mid-wavelength (green), and short-wavelength (blue) light. Both rods and cones contain the transmembrane protein opsin, and the prosthetic group retinal, a vitamin A derivative. The opsins in each cell type contain different amino acids that confer differences in light absorption.

The RPE, photoreceptor cells, external limiting membrane, outer nuclear layer, and outer plexiform layer constitute the neuro-epithelial layer of the retina.

The inner nuclear layer, inner plexiform layer, ganglion cell layer, nerve fiber layer, and internal limiting membrane constitute the cerebral layer of the retina. The inner nuclear layer contains bipolar cells, ganglion cells, horizontal cells, amacrine cells, Muller cells, and astrocytes, the latter two being types of glial cells. The Muller cells have nuclei in the inner nuclear area and cytoplasm extending from the internal limiting membrane 110 to the external limiting membrane 103. The external limiting membrane 103 is a region of terminal bars between Muller's cells and the visual receptors.

The next three layers of the retina are composed of various parts of the second neurons, whose nuclei reside in the inner nuclear layer and whose cytoplasmic processes extend into the outer plexiform layer to synapse with the receptor cells and to the inner plexiform layer to synapse with the ganglion cells. Thus, the second neuron is bipolar.

The third neuron, the multipolar ganglion cells, sends its nerve fiber (axon) to the optic nerve.

The last layer of the retina is the internal limiting membrane (ILM) on which the processes of the Muller's cells rest.

The retina contains a complex interneuronal array. Bipolar cells and ganglion cells are sensory cells that together form a path from the rods and cones to the brain. Other neurons form synapses with the bipolar cells and ganglion cells and modify their activity. For example, ganglion cells, or ganglia, generate action potentials and conduct these impulses back to the brain along the optic nerve. Vision is based on the modulation of these impulses, but does not require the direct relationship between a visual stimulus and an action potential. The visual photosensitive cells, the rods and cones, do not generate action potentials, as do other sensory cells (e.g., olfactory, gustatory, and auditory sensory cells).

Muller cells, the principal type of glial cells, form architectural support structures stretching radially across the thickness of the retina, and forming the limits of the retina at the outer and inner limiting membranes, respectively. Muller cell bodies in the inner nuclear layer project irregularly thick and thin processes in either direction to the outer and inner limiting membranes. These processes insinuate themselves between cell bodies of the neurons in the nuclear layers, and envelope groups of neural processes in the plexiform layers. Retinal neural processes can only have direct contact, without enveloping Muller cell processes, at their synapses. The junctions forming the outer limiting membrane are between Muller cells, and other Muller cells and photoreceptor cells, as sturdy desmosomes or zonula adherens. Muller cells perform a range of functions that contribute to the health of the retinal neurons. These functions include supplying endproducts of anaerobic metabolism (breakdown of glycogen) to fuel neuronal aerobic metabolism; removing neural waste products such as carbon dioxide and ammonia and recycling spent amino acid transmitters; protecting neurons from exposure to excess neurotransmitters using uptake and recycling mechanisms; phagocytosis of neuronal debris and release of neuroactive substances; synthesizing retinoic acid, required in the development of the eye and nervous system, from retinol; controlling homeostasis and protecting neurons from deleterious changes in their ionic environment by taking up and redistributing extracellular $K^+$; and contributing to generation of the electroretinogram (ERG) b-wave, the slow P3 component of the ERG, and the scotopic threshold response (STR) by regulating $K^+$ distribution across the retinal vitreous border, across the whole retina, and locally in the inner plexiform layer of the retina.

Astrocytes, the other type of glial cell, envelope ganglion cell axons and have a relationship to blood vessels of the nerve fiber, suggesting they are axonal and vascular glial sheaths and part of a blood-brain barrier. They contain abundant glycogen, similar to Muller cells, and provide nutrition to the neurons in the form of glucose. They may serve a role in ionic homeostasis in regulating extracellular $K^+$ levels and neurotransmitter metabolism. They have a characteristic flattened cell body and fibrous radiating processes which contain intermediate filaments. The cell bodies and processes are almost entirely restricted to the nerve fiber layer of the retina. Their morphology changes from the optic nerve head to the periphery: from extremely elongated near the optic nerve to a symmetrical stellate form in the far peripheral retina.

Microglial cells are not neuroglial cells and enter the retina coincident with mesenchymal precursors of retinal blood vessels in development, and are found in every layer of the retina. They are one of two types. One type is thought to enter the retina at earlier stages of development from the optic nerve mesenchyme and lie dormant in the retinal layers for much of the life of the retina. The other type appears to be blood-borne cells, possibly originating from vessel pericytes. Both types can be stimulated into a macrophagic function upon retinal trauma, in degenerative diseases of the retina, etc. when they then engage in phagocytosis of degenerating retinal neurons.

All glial cells in the central nervous system (CNS) are coupled extensively by gap junctions. This coupling underlies several glial cell processes, including regulating extracellular $K^+$ by spatial buffering, propagating intercellular $Ca^{2+}$ waves, regulating intracellular ion levels, and modulating neuronal activity.

Activation of retinal glial cells with chemical, mechanical, or electrical stimuli often initiate propagated waves of calcium ions ($Ca^{2+}$). These $Ca^{2+}$ waves travel at a velocity of 23 μm/second and up to 180 μm/second from the site of initiation. The waves travel through both astrocytes and Muller cells, even when the wave is initiated by stimulating a single astrocyte.

$Ca^{2+}$ waves propagate between glial cells in the retina by two mechanisms: diffusion of an intracellular messenger through gap junctions, and release of an extracellular messenger. $Ca^{2+}$ wave propagation between astrocytes is mediated largely by diffusion of an intracellular messenger, likely inositol triphosphate (IP3), through gap junctions, along with release of adenosine triphosphate (ATP). Propagation from astrocytes to Muller cells, and from one Muller cell to other Muller cells, is mediated by ATP release.

Retinal neurons and glial cells also communicate. Muller cells have transient $Ca^{2+}$ increases that occur at a low frequency. Stimulating the retina with repetitive light flashes significantly increases the frequency of these $Ca^{2+}$ transients, most prominent in Muller cell endfeet at the retinal surface, but also in Muller cell processes in the inner plexiform layer. This neuron-to-glial cell communication indicates that glial cell $Ca^{2+}$ transients are physiological responses in vivo.

Stimulated glial cells directly modulate the electrical activity of retinal neurons, leading either to enhanced or depressed neuronal spiking. Inhibitory glial modulation of neuronal spiking may be $Ca^{2+}$-dependent, because the magnitude of neuronal modulation was proportional to the amplitude of the $Ca^{2+}$ increase in neighboring glial cells. Glial cells can modulate neuronal activity in the retina by at least three mechanisms. In some ganglion cells, glial cell activation facilitates synaptic transmissions and enhances light-evoked spiking. In other ganglion cells, there is depressed synaptic transmissions and decreased spiking. Glial cell activation can also result in ganglion cells hyperpolarization, mediated by activating A1 receptors and opening neuronal $K^+$ channels.

Stimulated glial cells also indirectly modulate the electrical activity of retinal neurons. This is mediated by glutamate uptake by Muller cells at synapses by glutamate transporters such as GLAST (EAAT1) and GLT-1 (EAAT2) in Muller cells. When glutamate transport in the retina is blocked, both the amplitude and the duration of ganglion cell EPSCs are increased. Glial cell modulation of electrical activation of retinal neurons is also mediated by regulating extracellular $K^+$ and $H^+$ levels. Neuronal activity leads to substantial variations in the concentration of $K^+$ and $H^+$ in the extracellular space, which can alter synaptic transmission; an increase of $K^+$ depolarizes synaptic terminals, while an increase of $H^+$ blocks presynaptic $Ca^{2+}$ channels and NMDA receptors. Muller cells regulate extracellular concentrations of $K^+$ and $H^+$, thus influencing the effect of these ions on synaptic transmission.

With reference to FIG. 2, one skilled in the art will appreciate that solar cell micro- and/or nano-particles 125, provided selectively or substantially throughout the all regions of the retina, enhance, facilitate or boost the ability of these biological cells to regulate their polarity. This is in contrast to use of a device that supplies an electrical potential, that is implanted in an invasive surgical procedure, that is localized, etc. In embodiments solar cell micro- and/or nano-particles 125 may be provided in combination with implanted light guides, such as fiber optics, to enhance the efficiency of therapeutic stimulation. The micro- and/or nano-particles 125 may be coated with or, if the light guide material includes a polymer, included in at least a surface layer of guides having conventional cylindrical shapes, tubular shapes, substantially two-dimensional shapes, or three-dimensionally-branching tree-like structures. As one example, an implanted guide structure coated with the particles and membrane ion channel activators may be implanted inside any layer of the eye (e.g., subretinally, intraretrinally, epiretinally, in the vitreous, in the choroid, etc.) and activated with light to stimulate specific layers of cells. As another example, injected particles may be stimulated by implanted guide structures with light at lesser intensities than would be required by purely transmissive exposure from an entirely extra-ocular source.

Besides pathologies in one or more of the above described mechanisms to maintain and/or regulate retinal cell polarity, other excitable cells besides the retina may have pathologies that occur from defects in cell plasma membrane polarization. As one example, excitable cells in the brain of Alzheimer's patients have abnormal electrical conducting and stabilizing mechanisms, resulting in loss of electrical stimulation. Repolarization of these cells provides additional stimulation to replace the abnormal cell membrane polarization and/or the cell membrane polarization that was diminished or lost. As another example, glial cell scar tissue culminating from epileptic seizures results in abnormal electrical stabilizing mechanisms in excitable cells of the brain. Repolarization of these cells provides a stabilized threshold, resulting in a calming effect. One skilled in the art will appreciate other pathologies for which the inventive method may be used. Therapeutic stimulation of the brain, spinal cord, and/or peripheral nerves may similarly be performed with implanted fiber optics, including cylindrical, tubular, substantially two- or three-dimensional branching tree-like structures, to deliver light to these tissues. In embodiments of a polymeric fiber optic material, the particles and/or nanowires may be included in at least a surface layer of the polymer, with or without conjugated biomolecules with either direct or indirect linkage and/or non-conjugated biomolecules. In one embodiment an implanted three-dimensional branching fiber optic structure coated with membrane ion channel activators is provided, e.g., implanted, and is activated with light to stimulate an organ such as the brain in multiple separate areas simultaneously. In one embodiment the structure is positioned on the organ surface. In one embodiment the structure is positioned internally in the organ. In one embodiment an implanted tubular structure is provided to bridge or to surround cut nerves. In one embodiment such a structure is coated with appropriate stimulating compounds, e.g., nerve growth factor, to stimulate axonal growth, or is coated with appropriate inhibiting compounds to inhibit scar formation at the site of trauma. In one embodiment such a structure is provided with stimulating or inhibiting compounds administered separately. In one embodiment the structures may be positioned on and/or in any organ or system, e.g., spinal cord, peripheral nerves, heart, brain, etc.

The inventive method includes mechanisms to delay, minimize, reduce, alleviate, correct, or prevent electro-sensory polarization pathologies. Such mechanisms may attenuate cellular damage resulting from abnormal polarization, reduced polarization, enhanced polarization, hyperpolarization, or loss of polarization. These polarization defects may be of any type and/or cell combination, and may stimulate and/or de-stimulate the cell(s). They may, for example, be transient in one cell type, sustained in one cell type, propagated to affect adjacent cells, propagated along a network to affect non-adjacent cells, etc.

It is known attaching nanocrystal quantum dots to semiconductor layers increases the photovoltaic efficiencies. The semiconductor solar cells work by using the energy of incoming photons to raise electrons from the semiconductor's valence band to its conduction band. A potential barrier formed at the junction between p-type and n-type regions of the semiconductor forces the pairs to split, thereby producing a current, thus influencing, changing, or regulating the polarization of a membrane. The particles are stimulated by using an external or internal energy source. Polarization of the particles is regulated by producing or varying the current. The particles are used to stimulate the cell membrane by varying the input energy from the energy source.

One embodiment provides nano- or micro-sized solar cells to regulate the polarity of excitable cells. As previously described, excitable cells include, but are not limited to, sensory cells such as the retina of the eye, all three types of muscle cells, and central and peripheral system nerve cells. Such nano- or micro-sized solar cells are hereinafter generally referred to as particles 125 as shown in FIG. 2. In one embodiment, particles encompass any and all sizes which permit passage through intercellular and/or intracellular spaces in the organ or area of the organ of interest. For example, intercellular spaces in the retina are about 30 angstroms ($30 \times 10^{-8}$), so that particles for intercellular retinal distribution may be sized for these spaces, as known to one skilled in the art. In one embodiment, the particles are inserted within the lipid bilayer of liposomes and, following administration, the particles become incorporated within the cell membrane of a desired cell type or types.

The solar cell nano- and/or micro-particles 125 are three dimensional semiconductor devices. The particles use light energy or ultrasound energy to generate electrical energy to provide a photovoltaic effect. In one embodiment, the particle material is a ceramic. In another embodiment, the particle material is a plastic. In another embodiment, the particle material is silicon. Particles of crystalline silicon may be monocrystalline cells, poly or multicrystalline cells, or ribbon silicon having a multicrystalline structure. These are fabricated as microscale or nanoscale particles that are administered to a patient.

The particles may be a nanocrystal of synthetic silicon, gallium/arsenide, cadmium/selenium, copper/indium/gallium/selenide, zinc sulfide, indium/gallium/phosphide, gallium arsenide, indium/gallium nitride, and are synthesized controlling crystal conformations and sizes. In one embodiment, the nanoparticle may comprise a nanocrystal, such as cadmium/selenium (Cd/Se), and a metal. For example, a CdSe/Au nanometer-sized composite particle may be synthesized through a two-step procedure, where CdSe nanorods are formed by the reaction of Cd and Se precursors in a mixture of trioctylphosphine oxide and an alkylphosphonic acid to form rod-shaped CdSe nanoparticles, and the CdSe rods are treated with a mixture of gold chloride, didodecyldimethyl-ammonium bromide, and hexadecylamine to stabilize the nanocrystals and to reduce the gold chloride to elemental gold. Because the two ends of the CdSe rods differ crystallographically, and therefore chemically, control of growth conditions allows growth of Au particles preferentially on one end of each rod. In addition to CdSe/Au particles, one skilled in the art will readily recognize that particles can be constructed from a variety of other semiconductor/metal and semiconductor/semiconductor hetero-junctions. For example, particles based upon semiconductor/metal hetero-junctions between group II-VI, IV, III-V, IV-VI, referring to groups of the periodic table, metal-oxide, or organic semiconductors and a metal, and in particular those based upon Si/Au, GaAs/Au, InAs/Au, and PbS/Au hetero-junctions, can be used in the same way as those discussed here.

The particles (quantum dots and/or semiconductor nanowires) may also be biocompatible short peptides made of naturally occurring amino acids that have the optical and electronic properties of semiconductor nano-crystals. One example is short peptides of phenylalanine. The particles can consist of both inorganic or organic materials, as previously described.

The particles may be coated with biocompatible mono- or bilayers of phospholipid a protein, a peptide polyethylene glycol (PEG) that can be used as a scaffold to aid in biocompatibility of the particle. The particles can be entirely or partially biodegradable.

The particles may also be included in or coated on a bioabsorbable or non-bioabsorbable but biocompatible polymer structured or configured as a fiber, a tube, a substantially two-dimensional structure, or a three-dimensional structure to fit any anatomical or physiological site. The coated polymer structure may be any desirable length or size in order to maintain its position with respect to a tissue structure. The therapeutic stimulation of the polymer and adjacent tissue may stimulate and/or inhibit the excitation of cells depending upon the wavelength of the applied light and the character of the one or more types of particles associated with it, with differing parts of the polymer, e.g., the front and back sides of a substantially two-dimensional structure, having different particles in order to have different effects upon the target cells adjoining those parts.

In one embodiment, the particles are delivered to the retinal cell cytoplasm or nucleus or cell membrane, regardless of the particular injection site in the eye. In one embodiment, the particles are introduced into the central nervous system, e.g., by injection. In one embodiment, the quantum dots are covalently linked, i.e., conjugated, with natural or synthetic biomolecules (e.g., proteins, peptides, nucleic acids, oligonucleotides, etc.) that introduce a vector (e.g., adeno-associated virus (AAV) for retinal gene therapy. Such a vector and/or the bound quantum dots/semiconductor nanowires can be labeled for visualization, tracking, sensing, etc. For example, the quantum dots can be labeled or tagged with a signal recognition moiety. Such a vector can incorporate quantum dots into the viral capsid using, e.g., (poly)ethylene glycol (PEG) moieties. Combinations of these embodiments are contemplated and included in the inventive method, using methods known by one skilled in the art and as subsequently described.

In one embodiment, the particles are conjugated with a moiety such as an ocular peptide or protein, to result in a biologically active quantum dot conjugate. Such conjugation allows the therapeutic effect to be controlled and specific, while sensing and tracking the conjugate location, function, etc. in, e.g., the retina.

Examples of such ocular peptides and proteins include, but are not limited to, membrane-bound G-protein coupled photoreceptors (opsins, including the rod cell night vision pigment rhodopsin and cone cell color vision proteins), and members of the family of ocular transport proteins (aquaporins).

In one embodiment, short peptides of naturally occurring amino acids that have the optical and electronic properties of semiconductor nano-crystals are conjugated to the particles. One non-limiting example of such a short peptide is (poly)phenylalanine. In these embodiments, the resulting conjugate contains both inorganic and organic materials, as previously described. In one embodiment, the conjugates may be coated with biocompatible mono- or bilayers of phospholipid, protein, and/or a (poly)ethylene glycol (PEG) molecule that can be used as a scaffold to aid in biocompatibility of the particle. Any of these organic moieties may be utilized to ionically, electronically or covalently form the biologically active conjugates. The conjugates are entirely or partially biodegradable.

In one embodiment, a particle conjugated to a vector is capable of modifying an ocular gene, e.g., a gene of a retinal cell. In this embodiment, the quantum dot and/or semiconductor nanowire, besides regulating membrane polarity of an excitable cell such as a retinal cell, also provides therapy to ameliorate or prevent a genetically based retinal disease (e.g., retinitis pigmentosa). In one embodiment, the vector may be a plasmid vector, a binary vector, a cloning vector, an expression vector, a shuttle vector, or a viral vector as known to one skilled in the art. The vector typically contains a promoter, a means for replicating the vector, a coding region, and an efficiency increasing region. In one embodiment, the vector is a virus such as an adenovirus, an adeno-associated virus (AAV), a retrovirus, and other viral vectors for gene therapy, as known to one skilled in the art. As one non-limiting example, particles are functionalized and/or linked to viral vectors using (poly)ethylene glycol (PEG) moieties. The number of PEGS can be varied depending on, e.g., ocular site, need to enhanced hydrophilicity, protein size, etc. The viral vector and particle are combined in the presence of at least one biocompatible adjuvant, suspension agent, surfactant, etc. Particles may be coated with or linked to, e.g., folate, polydopamine, etc. so that these molecules are targeted intracellularly, extracellularly, to a cell membrane, to a specific cellular site or organelle, etc.

Conjugation of quantum dots to viral capsids permits in vivo observation of retinal neurons and the individual glycine receptors in living neurons. A single quantum dot can be recognized by optical coherence tomography (OCT) and can be counted, tracked, assessed, monitored, and evaluated for longevity and efficacy, and hence therapy can also be monitored, over time.

In one embodiment, particles associated with other biomolecules, e.g., conjugated with halorrhodopson, conjugated with a customized virus, are used to regulate, i.e., stimulate or inhibit, action potential of a neuron. Quantum dots and semiconductor nanowires can be associated with, e.g., conjugated with, a virus, a virus capsid, a cell penetrating protein, and/or other molecule(s) to stimulate specific neurons or specific neuronal function, or may be provided with appropriate stem cells. In one embodiment, these combinations may stimulate or inhibit the action potential of cells depending upon the wavelength(s) of light applied to them to provide a highly selective "on or off" form of external regulation.

In one embodiment, covalent conjugation may not be required or desired, and in this embodiment particles may be simply associated with a viral vector. In one embodiment, quantum dots may be mixed with an appropriate viral vector in the presence of a cationic polymer, e.g. hexadimethrine bromide POLYBRENE® to form a colloidal complex suitable for introducing into a retinal cell. In one embodiment, particles are tagged with an amide, a thiol, etc. using electrostatic interaction along with functionalizing means known to one skilled in the art.

In one embodiment, the quantum dots that are conjugated or associated with a biomolecule are delivered to a target cell cytoplasm or nucleus, using described methods and/or methods known in the art. In one embodiment, the biomolecule comprises nucleic acid, such as DNA and RNA, as well as synthetic congeners thereof. Non-limiting examples of nucleic acids may include plasmid DNA encoding protein or inhibitory RNA producing nucleotide sequences, synthetic sequences of single or double strands, missense, antisense, nonsense, on and off and rate regulatory nucleotides that control protein, peptide, and nucleic acid production. Nucleic acids include, but are not limited to, genomic DNA, cDNA, RNAi, siRNA, shRNA, mRNA, tRNA, rRNA, microRNA, hybrid sequences or synthetic or semi-synthetic sequences. Each of these may be naturally occurring or synthetic. Each of these may be of human, plant, bacterial, yeast, viral, etc. origin. Each of these may be any size, e.g., ranging from oligonucleotides to chromosomes. They may be obtained by any technique known to one skilled in the art.

In one embodiment, a nucleotide sequence may also encode products for synthesis or inhibition of a therapeutic protein such as, but not limited to, anti-cancer agents, growth factors, hypoglycemic agents, anti-angiogenic agents, bacterial antigens, viral antigens, tumor antigens, and/or metabolic enzymes. Examples of anti-cancer agents include, but are not limited to, interleukin-2, interleukin-4, interleukin-7, interleukin-12, interleukin-15, interferon-α, interferon-β, interferon-γ, colony stimulating factor, granulocyte-macrophage stimulating factor, anti-angiogenic agents, tumor suppressor genes, thymidine kinase, eNOS, iNOS, p53, p16, TNF-α, Fas-ligand, mutated oncogenes, tumor antigens, viral antigens, and/or bacterial antigens. In one embodiment, plasmid DNA may encode for an RNAi molecule designed to inhibit protein(s) involved in tumor or other hyperproliferative cells' growth or maintenance. In one embodiment, a plasmid DNA may simultaneously encode a therapeutic protein and one or more RNAi molecules. In one embodiment, a nucleic acid may be a mixture of plasmid DNA and synthetic RNA, including sense RNA, antisense RNA, ribozymes, etc.

In one embodiment, the disclosed quantum dot-nucleic acid complex is administered to an individual, e.g., patient in need of such therapy, to ameliorate a genetic disease. In one, embodiment, the disclosed quantum dot-nucleic acid complex is administered to an individual, e.g., a patient with a tumor, to reduce the tumor burden, ameliorate tumor effects, treat the tumor, etc. Therapy may be curative, palliative, remediation, etc. and may be either total or partial, and may be either therapeutic or preventive. The disclosed quantum dot-nucleic acid complex may be used in gene targeting or knockout of specific genes, for e.g., with at least one engineered nuclease, tumor suppressor gene(s), etc. In one embodiment, the disclosed quantum dot-nucleic acid complex contains a wild-type or non-mutated form of a gene or part of a gene, and is introduced into a cell or cells, with the wild-type or non-mutated form of the nucleic acid replacing a defective and/or mutated form of the nucleic acid, e.g., DNA. Because the nucleic acid may be synthetic oligonucleotide, the disclosed gene therapy can replace missing or defective copies of a nucleic acid, and/or restore or impart a new function to overcome a disease.

In one embodiment, the disclosed method of gene therapy is somatic gene therapy and thus applied to the patient undergoing therapy. In one embodiment, the disclosed method of gene therapy is germ line gene therapy and thus not limited to the patient undergoing therapy, being capable of transmission to offspring of the patient. In one embodiment, the disclosed gene therapy methods comprise delivery of a single gene or multiple genes. Multiple genes may be in a single quantum dot complex, or may be in multiple quantum dot complexes. Multiple quantum dot-nucleic acid complexes may be administered either at the same times or at different times. In embodiments where the nucleic acid in the quantum dot complex is in a linear form, e.g., a linear DNA fragment, when introduced into cells, the linear nucleic acid molecules are ligated end-to-end by intracellular enzymes to form long tandem arrays, which promote integration of the nucleic acid into a chromosome.

In embodiments, the disclosed gene therapy methods can be provided alone, or in combination with additional treatments such as stem cell therapy. In one embodiment, a method for treating retinal, CNS, and cardiovascular diseases is provided by providing the disclosed quantum dot-nucleic acid complexes to the patient to effect gene therapy, along with stem cell therapy as known in the art. The therapies may be provided together or separately. In one embodiment, the disclosed method may be provided as part of a combination therapy additionally comprising, e.g., agents such as immunomodulators, anti-VEGF agents, anti-integrins, anti-inflammatory agents, antibiotics, anti-viral agents, anti-fungal agents, anti-proliferative agents, anti-cancer agents, etc.

In one embodiment, the disclosed quantum dot-nucleic acid complex may be targeted and/or directed to a specific region of the body, e.g., a specific organ, tissue type, and/or cell type, where the targeted location may be the site of a disease or a location affected by a disease. In one embodiment, the quantum dot contains or is provided with a coating to enhance or impart biocompatibility and/or cell selectivity using, e.g., an antibody, receptor, etc. that directs the complex to a desired location, e.g., a tumor site, a specific receptor, etc. In one embodiment, targeting or directing the complex may occur using a selected site to provide access to the desired location. For example, in ocular diseases, the disclosed quantum dot-nucleic acid complex may be injected intravitreally, introduced into the cornea, choroid, retina, etc., provided as a topical formulation, etc., as also described herein.

In one embodiment, the disclosed quantum dot-nucleic acid complex may provide both therapeutic and imaging functions. For example, to evaluate the effect of gene modification in the eye, visual acuity electroretinogram, visual field, OCT, ophthalmoscopy, and/or photography may be employed. In one embodiment, the disclosed quantum dot-nucleic acid complex is imaged by photography and/or optical coherence tomography (OCT) in accessible regions such as the eye and skin, and/or is imaged by magnetic resonance imaging (MRI). The ability to image the disclosed complex, particularly when the complex comprises a targeting moiety, provides diagnostic value. Complex accumulation, concentration, or localization at a specific site or area of the body, e.g., breast, brain, prostate, etc., is indicative that this area exhibits the disease or condition to be treated. The disclosed complex may also be imaged by more routine methods such as microscopy visualizing the complex in samples of tissue, including biopsy tissue samples, or body fluids including but not limited to blood.

In one embodiment, the disclosed quantum dot-nucleic acid complex further contains at least one moiety that binds to a tumor-specific protein marker. In one embodiment, the complex still further contains a reporter molecule, in addition to the binding moiety, e.g., an antibody directed to a tumor marker. Reporter molecules are known in the art and include, but are not limited to, molecules that are fluorescent, luminescent, phosphorescent, etc. In this embodiment the complex is administered systemically to a patient to diagnose a tumor by locating and/or imaging the protein-nucleic acid-tumor binding moiety at a tumor site. For example, following administration of the complex to a patient, a blood sample is obtained from the patient and subjected to an immunofluorescence assay and/or examined by fluorescent microscopy to detect and/or measure the amount of the tumor marker in the sample. In one embodiment, the quantum dot of the complex and the reporter molecule, such as a fluorescent dye, of the anti-tumor marker antibody have excitation (ex) and emission (em) maxima at different wavelengths, and the sample is examined at multiple wavelengths. The determination of binding by both the complex and anti-tumor marker antibody in the assay provides a more definitive determination that the tumor marker, and thus the tumor, is present in the patient. In one embodiment, the reporter molecule of the anti-tumor marker antibody has emission maxima at the green wavelengths of light. In one embodiment, the specificity of the complex for a tumor is increased by associating multiple tumor marker-binding proteins to the complex. This embodiment provides enhanced opportunities for early detection of a tumor, and prior to tumor metastasis.

The following disclosure demonstrates use in various therapies. In one embodiment, a method for inducing a mammalian cell to produce a recombinant protein is provided. In this embodiment, the disclosed quantum dot-nucleic acid encoding the recombinant protein is provided to a patient. In one embodiment, a method for anemia therapy in a patient is provided. In this embodiment, the disclosed quantum dot-nucleic acid encoding an angiogenic agent, e.g., erythropoietin, is provided to a patient, thereby providing therapy for anemia in the patient. In one embodiment, a method for vasospasm therapy in a patient is provided. In this embodiment, the disclosed quantum dot-nucleic acid encoding inducible nitric oxide synthase (iNOS) is provided to a patient, thereby providing therapy for vasospasm in the patient. In one embodiment, a method for improving cell survival in a patient is provided. In this embodiment, the disclosed quantum dot-nucleic acid encoding a heat shock protein is provided to a patient, therapy providing therapy for increased cell survival. In one embodiment, a method for decreasing incidence of a restenosis of a blood vessel, following a procedure that enlarges the blood vessel, is provided. In this embodiment, the disclosed quantum dot-nucleic acid encoding a heat shock protein is provided to a patient, thereby decreasing incidence of a restenosis in the patient. In one embodiment, a method for increasing growth from a hair follicle in a scalp of a patient is provided. In this embodiment, the disclosed quantum dot-nucleic acid encoding a telomerase or an immunosuppressive protein is provided to a patient, thereby increasing hair growth from a hair follicle. In one embodiment, a method of inducing expression of an enzyme with antioxidant activity in a cell is provided. In this embodiment, the quantum dot-nucleic acid encoding the enzyme is provided to a patient, thereby inducing expression of the enzyme with antioxidant activity in a cell. In one embodiment, a method of cystic fibrosis therapy is provided. In this embodiment, the disclosed quantum dot-nucleic acid encoding Cystic Fibrosis Transmembrane Conductance Regulator (CFTR) is provided, thereby providing therapy for cystic fibrosis in the patient. In one embodiment, a method for treating an X-linked agammaglobulinemia in a patient is provided. In this embodiment, the disclosed quantum dot-nucleic acid encoding a Bruton's tyrosine kinase is provided to a patient, thereby providing therapy for an X-linked agammaglobulinemia in the patient. In one embodiment, a method of therapy for an adenosine deaminase severe combined immunodeficiency (ADA SCID) in a patient is provided. In this embodiment, the disclosed quantum dot-nucleic acid complex encoding an ADA is provided to a patient, thereby providing ADA SCID therapy in the patient. In one embodiment, a method of therapy for hemophilia B in a patient is provided. In this embodiment, the disclosed quantum dot-nucleic acid encoding Factor IX is provided to a patient, thereby providing therapy for hemophilia B. In one embodiment, a method of therapy for spinal muscular atrophy in a patient is provided. In this embodiment, the disclosed quantum dot-nucleic acid complex encoding SMN-1 is provided to a patient, thereby providing therapy for spinal muscular atrophy in the patient. In one embodiment, a method for providing therapy for exudative age related macular degeneration (AMD) in a patient is provided. In this embodiment, the disclosed quantum dot-nucleic acid encoding an anti-VEGF protein is provided, thereby providing therapy to the patient with exudative AMD. In one embodiment, the anti-VEGF protein is sFlt-1, which is a naturally occurring protein antagonist of VEGF. In one embodiment, a method of therapy for choriodemia in a patient is provided. In this embodiment, the quantum dot-nucleic acid complex encoding Rab-Escort Protein (REP-1) is provided to the patient, thereby providing therapy for choriodemia in the patient. In one embodiment, a method of therapy for Leber's congenital amaurosis (LCA) in a patient is provided. In this embodiment, the quantum dot-nucleic acid encoding RPE65 is provided to the patient, thereby providing therapy for Leber's congenital amaurosis in the patient. RPE65 is an RPE-specific 65-kDA protein involved in conversion of all-trans retinol to 11-cis retinal during phototransduction, and has been implicated as a genetic defect in LCA. In one embodiment, a method of therapy for retinitis pigmentosa in a patient is provided. In this embodiment, the quantum dot-nucleic acid encoding MERTK is provided to the patient, thereby providing therapy for retinitis pigmentosa in the patient. In one embodiment, a method of therapy for Stargardt's syndrome in a patient is provided. In this embodiment, quantum dot-nucleic acid encoding ABC4 is provided to a patient, thereby providing therapy for Stargardt's syndrome in the patient. The ABCA4 gene produces a protein involved in energy transport to and from photoreceptor cells in the retina. In one embodiment, a method of therapy for Usher's syndrome (1B) in a patient is provided. In this embodiment, the quantum dot-nucleic acid encoding MY07A is provided to a patient, thereby providing therapy for Usher's syndrome (1B) in the patient. In one embodiment, a method of therapy for advanced and/or metastatic pancreatic cancer in a patient is provided. In this embodiment, the quantum dot-nucleic acid encoding two genes, somatostatin receptor subtype 2 (sst2) and deoxycitidine kinase uridylmonophosphate kinase (dck::umk), which exhibit complementary therapeutic effects, is provided to the patient, thereby providing therapy for advanced and/or metastatic pancreatic cancer in the patient. Both genes induce an antitumor bystander effect and render gemcitabine treatment more efficient.

In embodiments, other ocular pathological conditions as well as additional therapeutic nucleic acids may be provided, some of which were previously described. Examples include, but are not limited to, retinitis pigmentosa, color blindness, wet and dry ARMD, diabetic retinopathy, corneal dystrophies, Meesman syndrome, Fuchs syndrome, granular and macular corneal dystrophies, keratoconous, Sejorgen's syndrome, inherited glaucoma, retinohyaloidopathies, congenital cataract, Marfan syndrome, choridermia x-linked retinoschisis, achromatopsia, etc.

The administration site, location, and/or method of the disclosed quantum dot-nucleic acid complex is not limited. In one embodiment, the disclosed quantum dot-nucleic acid complex may be injected into a vein or artery. In one embodiment, the disclosed quantum dot-nucleic acid complex may be introduced into the cerebrospinal fluid, ventricles, CNS, spinal cord, etc. for therapy of numerous CNS diseases such as Alzheimer's disease, Parkinson's disease, multiple sclerosis, etc. The disclosed method may be used as therapy for patients with spinal muscular dystrophy, muscular dystrophy, diseases affecting myeloid cells, chronic lymphocytic leukemia, multiple myeloma, malignant tumors, melanomas, cancers of various organs including breast, intestine, prostate, CNS, glioblastoma, sarcoma, etc. In addition, the present methods can be used to provide therapy for cystic fibrosis, hemophilia, and sickle cell disease.

In one embodiment, the disclosed quantum dot-nucleic acid complex additionally contains a magnetic or paramagnetic nanoparticle that facilitates introduction of the complex into a cell. In one embodiment, the complex comprises a quantum dot conjugated with a targeting moiety and a biomolecule, such as a gene, DNA, RNA, RNAi, sRNA, plasmid, etc., and a magnetic or paramagnetic nanoparticle also conjugated with the targeting moiety. In embodiments, the targeting moiety is an antibody or a ligand for a receptor.

In one embodiment, a method is provided for introducing the described complex into a desired cell, and thus for introducing the biomolecule, such as a gene for stimulating or silencing cell or tumor cell function. In this embodiment the complex is administered, either systemically or locally, to reach a desired cell. An energy source is then applied, e.g., an alternating magnetic field, electromagnetic radiation, etc., causing a temperature increase in the magnetic or paramagnetic nanoparticle. This temperature increase perturbs the cell membrane of the desired cell, and thus provides or enhances access to the cell at the site of the perturbation, e.g., ranging from an altered membrane conformation to a "hole". Perturbation of the cellular membrane provides enhanced access into the cellular membrane and cytoplasm of the cell. Perturbation of the nuclear membrane provides enhanced access into the nuclear membrane and nucleoplasm of the cell.

Following access of the complex, or at least the nanoparticle containing the biomolecule, into the cell, the biomolecule provides the desired cellular effect. That is, the biomolecule is readily accessible to the cellular cytoplasm or nucleus.

In one embodiment, the quantum dot conjugated with the biomolecule may be coated with a thermosensitive polymer. Thermosensitive polymers are known in the art and include, but are not limited to, chitosan, (poly)ethylene glycol (PEG), etc. Application of an external energy source results in a slight increase in temperature, e.g., to about 39° C. to about 43° C. in one embodiment, to about 40° C. to about 42° C. in another embodiment. This slight temperature increase facilitates release of the biomolecule from the thermosensitive nanoparticles or quantum dot.

In general, the size of the quantum dot defines the wavelength of light that is absorbed by it and, similarly, the wavelength that can be emitted by it which is always longer than that absorbed. For example, a quantum dot with a size of about 200 nm-500 nm dot absorbs a longer wavelength of light than a quantum dot with a size of about 10 nm-50 nm. As a result, the wavelength that is emitted by larger quantum dots will have a larger wavelength (carry less energy, or a shift toward the red), than those wavelengths emitted by smaller quantum dots (carry more energy, or a shift toward the blue). Therefore using different sized quantum dots, one can not only selectively stimulate the specific membrane ion channel or cells, but also make them visible differently due to their different emission of wavelengths of light.

This permits one to selectively activate cells, i.e., turn certain cells on or off, without affecting the other cells. Similarly, such cells selectively activated or turned on can also be coded with one or more different antibody, gene, biomolecule, etc. Such size tunable parameters apply equally to nanowires or nanotubes in addition to quantum dots, and can be used in addition in spectroscopy.

In one embodiment, the complex comprises quantum dots that have two different sizes. Typically, the size of the quantum dots range from about 3 nm to about 50 nm, and the size of the magnetic or paramagnetic nanoparticle ranges from about 70 nm to about 200 nm. In this embodiment, and by way of illustration only, one size of quantum dot is about 10 nm and the other size of quantum dot is about 25 nm. The sizes of the quantum dots are selected such that only one of the two sizes of quantum dot nanoparticles, and not the other size quantum dot nanoparticle, is susceptible to the external energy and increases in temperature, as described above for the magnetic or paramagnetic nanoparticle.

In one embodiment, the disclosed complex is activated by a light source that is implanted in the patient. This embodiment finds particular beneficial use for methods in which the quantum dot-nanoparticle is, or is likely to be, located at a body region or site that is less readily accessible or inaccessible to an external energy source, e.g. brain, spinal cord, etc. In one embodiment, an LED light source with a rechargeable battery is implanted in the patient. The LED provides a light pulse that activates the disclosed complex. In one embodiment, the light is transmitted by a fiber optic or a flexible silicone tube to a desired area(s).

In one embodiment, a fiber optic light source is implanted in a desired area of the brain, e.g., frontal lobe, parietal lobe, occipital lobe, temporal lobe, or cortex. In one embodiment, a fiber optic light source is implanted in a discrete area of the brain, e.g., basal ganglia including striatum, dorsal striatum, putamen, caudate nucleus, ventral striatum, nucleus accumbens, olfactory tubercle, globus pallidus, subthalamic nucleus; cerebellum including cerebellar vermis, cerebellar hemispheres, anterior lobe, posterior lobe, flocculonodular lobe, cerebellar nuclei, fastigial nucleus, globose nucleus, emboliform nucleus, dentate nucleus, and/or cortex including frontal lobe cortex and including primary motor cortex, supplementary motor cortex, premotor cortex, prefrontal cortex, gyri; parietal lobe cortex including primary somatosensory cortex (S1), secondary somatosensory cortex (S2), posterior parietal cortex, occipital lobe cortex including primary visual cortex (V1), V2, V3, V4, V5/MT; temporal lobe cortex including primary auditory cortex (A1), secondary auditory cortex (A2), inferior temporal cortex, posterior inferior temporal cortex; globus pallidus interna (GPi), caudal zona incerta, pallidofugal fibers, at an infarct site, at a scar tissue site, at a site in the spinal cord and/or peripheral nervous system.

In one embodiment, the disclosed complex need not necessarily be localized to the desired site for treatment, but the localized production of light causes activation of the complex at a desired site to treat the condition. The implanted LED/battery/fiber optic functions similar to an implanted cardiac pacemaker In one embodiment, a light source is external to the body with the end of the fiber optic accessible such that treatment can be performed outside a hospital setting, e.g., in a physician's office or in a medical outpatient facility. In one embodiment, the light source's controllable parameters, e.g., pulse frequency, pulse duration, pulse intensity, etc., can be controlled before or after implantation.

In one embodiment, a controller, either internal or external controls the light source's controllable parameters. The controller operates in a manner analogous to a cardiac pacemaker that regulates cardiac rhythm. It can be adjusted or regulated by a physician as needed, either through the skin or by exposing the implanted system at an appropriate and accessible location.

In one embodiment, an electrical sensor is provided with the implanted fiber optic, where the electrical sensor monitors conditions at the treatment site, such as electric potential, action potentials, etc. In embodiments, the electrical sensor is in communication with the controller such that the instructions provided by the controller to the light source, such as pulse frequency, pulse duration, pulse intensity, etc., may be adjusted by the controller based on the information from the electrical sensor.

In one embodiment, the electrical sensor is provided adjacent the implanted fiber optic source, e.g., along a side of the fiber optic source. For example, in one embodiment, the electrical sensor is implanted along a surface of a fiber optic tip, and ribbons, e.g., about 10 micron wide and spaced at 10 micron intervals, of graphene can be deposited/grown; the resulting graphene ribbons are then operatively connected to insulated wires. After implantation, graphene contacts the neuronal cells and terminates at various distances from the fiber optic tip. These graphene ribbons provide a feedback to the controller on the polarization status of the neuronal cells at the different depths of brain tissue. The graphene ribbons transmit the membrane polarization by the insulated wires attached to the graphene and to the controller, which is connected to the implanted light source, such as a light pulse generator (diode). The light source emits the software-controlled light pulses for stimulation of the area of the brain located near the fiber optic tip. One advantage of this embodiment is that the fiber optic device and light do not induce scar formation resulting in less or no tissue damage, and in contrast to currently used wires and devices to deliver electrical pulses. The light pulse achieves the desired results through activation of neuronal cells by activation of the disclosed complex, that is administered locally or systemically.

In one embodiment, the disclosed complex is injected locally immediately prior to placement of the fiber optic device though a cannula, under observation by magnetic resonance imaging (MRI). After the fiber optic is inserted in the cannula, the cannula is removed, leaving the wires connected to the fiber optic in the tissue. The exposed wires are connected to the controller that acts as a pulse receiver/ generator. The results generated by the disclosed system can be evaluated using various methodologies, e.g., electroencephalogram (EEG), etc. In embodiments, the disclosed system creates a feedback for controlling the light-stimulated neuronal cells.

In embodiments, the implanted LED/battery-fiber optic is used with the disclosed quantum dot-nucleic acid complex for therapy of patients with Parkinson's disease, epilepsy, spinal cord injury, and neurological diseases affecting an action potential.

In one embodiment, a method for transferring IGF-I to a cirrhotic liver using the disclosed quantum dot-nucleic acid encoding IGF-I where IGF-I is under control of a liver-specific promoter, is provided. Results show improved liver function and reduced liver fibrosis. As used herein, IGF-I is used interchangeably with insulin-like growth factor I and somatomedin C and relates to a family of polypeptides characterized by showing insulin-like effects and insulin-like structure, sharing nearly 50% of amino acid homology with insulin.

In one embodiment, a method of expressing GLP-1 protein using the disclosed quantum dot-nucleic acid complex encoding GLP-1 or a GLP-1 analog provides therapy for type II diabetes. A GLP-1 analog, also encompassed, is defined as a molecule having a modification including one or more amino acid substitutions, deletions, inversions, or additions when compared with GLP-1. GLP-1 analogs known in the art include, e.g., GLP-1(7-34) and GLP-1(7-35), GLP-1(7-36), Val$^8$-GLP-1(7-37), Gln$^9$-GLP-1(7-37), D-Gln$^9$-GLP-1(7-37), Thr$^{16}$-Lys$^{18}$-GLP-1(7-37), and Lys$^{18}$-GLP-1(7-37), disclosed in U.S. Pat. Nos. 5,118,666, 5,545,618, and 6,583,111. These compounds are the biologically processed forms of GLP-1 having insulinotropic properties.

In one embodiment, the disease for which the quantum dot-nucleic acid complex is provided is characterized by dysregulation of the immune system. In this embodiment, the nucleic acid encodes a cytokine such as human interferon α 2b (hINFα) for therapy.

In one embodiment, using the disclosed methods, a tumor suppressor gene or genes is provided to a patient in need thereof, such as a cancer patient. A tumor suppressor gene as used herein means a nucleotide sequence that may inhibit a tumor phenotype depending on its expression in the cell or may induce apoptosis. Many tumors lack functional tumor suppressor genes that encode proteins that can arrest tumor growth and promote tumor cell apoptosis. For example, the p53 protein arrests the cell cycle following DNA damage and is also involved in apoptosis. Efficient delivery and expression of the wild-type p53 gene cause regression of established human tumors, prevent growth of human cancer cells in culture, and renders malignant cells from human biopsies non-tumorigenic in nude mice. The p53 gene has been combined with standard therapies such as chemotherapy and radiotherapy with positive effect. In one embodiment, a method of therapy for cancer in a patient is provided. In this embodiment, the quantum dot-nucleic acid encoding p53 is provided to a patient, thereby providing therapy to the patient. Besides the p53 gene, other tumor suppressor genes include APC gene, DPC-4/Smad4 gene, BRCA-1 gene, BRCA-2 gene, WT-1 gene, retinoblastoma gene (Lee et al., Nature, 329: 642 (1987)), MMAC-1 gene, adenomatouspolyposis coil protein, deleted in colorectal cancer (DCC) gene, MMSC-2 gene, NF-1 gene, nasopharyngeal carcinoma tumor suppressor gene that maps at chromosome 3p21.3, MTS1 gene, CDK4 gene, NF-1 gene, NF-2 gene and/or VHL gene.

Other therapeutic genes useful for the disclosed method include those that encode enzymes, blood derivatives, hormones, lymphokines such as interleukins, interferons, tumor necrosis factor, etc., growth factors, neurotransmitters or their precursors or synthetic enzymes, trophic factors namely BDNF, CNTF, NGF, IGF, GMF, αFGF, βFGF, NT3, NT5, HARP/pleiotrophin, etc., apolipoproteins such as ApoAI, ApoAIV, ApoE, etc., dystrophin or a minidystrophin, the CFTR protein associated with cystic fibrosis, intrabodies, tumor-suppressing genes such as p53, Rb, Rap1A, DCC, k-rev, etc., genes encoding coagulation factors such as factors VII, VIII, IX, genes participating in DNA repair, suicide genes defined as genes whose products cause cell death, e.g., thymidine kinase (HS-TK), cytosine deaminase, etc., pro-apoptic genes, prodrug converting genes defined as genes encoding enzymes that convert prodrugs to drugs, and anti-angiogenic genes or alternatively, genes such as VEGF that promote angiogenesis.

The nucleic acid portion of the quantum dot-nucleic acid complex can also be used in gene silencing. Such gene silencing may be useful in therapy to switch off aberrant gene expression or studies to create single or genetic knockout models. Such nucleic acid is typically provided in the form of siRNAs. For example, RNAi molecules including siRNAs can be used to knock down DMPK with multiple CUG repeats in muscle cells for myotonic dystrophy therapy. In other examples, plasmids expressing shRNA that reduce the mutant Huntington gene (htt) responsible for Huntington's disease can be delivered. Other target genes include BACE-1 for the therapy of Alzheimer's disease. Some cancer genes may also be targeted with siRNA or shRNAs, such as ras, c-myc and VEGFR-2. Brain targeted siRNA may be useful in silencing BACE-1 in Alzheimer's disease, silencing of α-synuclein in Parkinson's disease, silencing of htt in Huntingdon's disease, and silencing of neuronal caspase-3 used in therapy of stroke to reduce ischemic damage.

In one embodiment, the nucleic acid is an RNA interference (RNAi), small interfering RNA or short interfering RNA (siRNA), short hairpin RNA (shRNA) molecule, or miRNA which is a RNA duplex of nucleotides targeted to a nucleic acid sequence of interest, e.g. huntingtin. As used herein, siRNA is a generic term that encompasses the subset of shRNAs and miRNAs. An RNA duplex refers to the structure formed by the complementary pairing between two regions of a RNA molecule. siRNA is targeted to a gene in that the nucleotide sequence of the duplex portion of the siRNA is complementary to a nucleotide sequence of the targeted gene. In embodiments, siRNAs are targeted to the sequence encoding ataxin-1 or huntingtin. In embodiments, the length of the duplex of siRNAs is less than 30 base pairs. In embodiments, the duplex can be 29, 28, 27, 26, 25, 24, 23, 22, 21, 20, 19, 18, 17, 16, 15, 14, 13, 12, 11 or 10 base pairs in length. In embodiments, the length of the duplex is 19 to 25 base pairs in length. In embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In embodiments the loop is 5, 6, 7, 8, 9, 10, 11, 12, 13, 14, 15, 16, 17, 18, 19, 20, 21, 22, 23, 24 or 25 nucleotides in length. In embodiments, the loop is 18 nucleotides in length. The hairpin structure can also contain 3' and/or 5' overhang portions. In embodiments, the overhang is a 3' and/or a 5' overhang 0, 1, 2, 3, 4 or 5 nucleotides in length. In one embodiment, the various forms of RNA such as microRNA, RNA interference, RNAi, and siRNA are designed to match the RNA copied from a defective gene, thereby inhibiting or diminishing production of the abnormal protein product of that gene.

In some embodiments, it may be useful to assess, monitor, track, evaluate location, evaluate stability, etc. of the particles conjugated or otherwise associated with a moiety as previously described. In these embodiments, the particles are tagged with a recognition moiety to provide a signal, and may themselves be conjugated to another biologically active moiety, e.g., DNA, RNA, peptide, protein, antibody, enzyme, receptor, etc., as known to one skilled in the art. Tagging may be effected via a covalent bond with a amide, thiol, hydroxyl, carbonyl, sulfo, or other such group on the biologically active moiety, as well known to one skilled in the art.

While each solar cell particle is oriented, in one embodiment, the plurality of particles provided in the body are not uniformly directionally oriented, nor do they require a backing layer to maintain orientation or position. They have a positive-negative (P-N) junction diode and may be constructed as either negative-intrinsic-positive (NIP) or positive-intrinsic-negative (PIN), as known to one skilled in the art. In one embodiment, where the nanoparticles are inserted into the cell membrane, the differential coating of portions of the particle with hydrophobic and hydrophilic materials can result in an orientation of the particles in the cell membrane.

As an example, p-type silicon wafers, and doped p-type silicon wafers to form n-type silicon wafers, are contacted to form a p-n junction. Electrons diffuse from the region of high electron concentration, the n-type side of the junction, into the region of low electron concentration, the p-type side of the junction. When the electrons diffuse across the p-n junction, they recombine with an electron deficiency (holes) on the p-type side. This diffusion of carriers does not happen indefinitely however, because of the electric field created by the imbalance of charge immediately either side of the junction which this diffusion creates. Electrons from donor atoms on the n-type side of the junction cross into the p-type side, leaving behind the (extra) positively charged nuclei of the group 15 (V) donor atoms such as phosphorous or arsenic, leaving an excess of positive charge on the n-type side of the junction. At the same time, these electrons are filling holes on the p-type side of the junction and are becoming involved in covalent bonds around the group 13 (III) acceptor atoms such as aluminum or gallium, making an excess of negative charge on the p-type side of the junction. This imbalance of charge across the p-n junction sets up an electric field which opposes further diffusion of charge carriers across the junction. The region where electrons have diffused across the junction is called the depletion region or the space charge region because it no longer contains any mobile charge carriers. The electric field which is set up across the p-n junction creates a diode, allowing current to flow in only one direction across the junction. Electrons may pass from the n-type side into the p-type side, and holes may pass from the p-type side to the n-type side. Because the sign of the charge on electrons and holes is opposite, current flows in only one direction. Once the electron-hole pair has been created by the absorption of a photon, the electron and hole are both free to move off independently within a silicon lattice. If they are created within a minority carrier diffusion length of the junction, then, depending on which side of the junction the electron-hole pair is created, the electric field at the junction will either sweep the electron to the n-type side, or the hole to the p-type side.

One embodiment of the invention uses nanocrystals of semiconductor material referred to as quantum dots (Evident Technologies, Troy N.Y.; Oceano NanoTech, Springdale Ak.). Nanocrystal solar cells are solar cells based on a substrate with a coating of nanocrystal. The nanocrystals are typically based on silicon, CdTe or GIGS and the substrates are generally silicon or various organic conductors. Quantum dot solar cells are a variant of this approach. These have a composition and size that provides quantum properties between that of single molecules and bulk materials, and are tunable to absorb light over the spectrum from visible to infrared energies. Their dimensions are measured in nanometers, e.g., diameter between about 1 nm to about 100 nm. When combined with organic semiconductors selected to have the desired activation properties, they result in particles with selectable features. The particles can also have passive iron oxide coatings with or without polyethylene glycol coatings or positive charge coatings as commercially provided. Quantum dot solar cells take advantage of quantum mechanical effects to extract further performance.

Nanocrystals are semiconductors with tunable bandgaps. The quantum dot nanocrystal absorption spectrum appears as a series of overlapping peaks that get larger at shorter wavelengths. Because of their discrete electron energy levels, each peak corresponds to an energy transition between discrete electron-hole (exciton) energy levels. The quantum dots do not absorb light that has a wavelength longer than that of the first exciton peak, also referred to as the absorption onset. Like other optical and electronic properties, the wavelength of the first exciton peak, and all subsequent peaks, is a function of the composition and size of the quantum dot. Smaller dots result in a first exciton peak at shorter wavelengths.

The quantum dots may be provided as a core, with a shell or coating of one or more atomic layers of an inorganic wide band semiconductor. This increases quantum yield and reduces nonradiative recombination, resulting in brighter emission provided that the shell is of a different semiconductor material with a wider bandgap than the core semiconductor material. The higher quantum yield is due to changes in the surface chemistry of the core quantum dot. The surface of nanocrystals that lack a shell has both free (unbonded) electrons, in addition to crystal defects. Both of these characteristics tend to reduce quantum yield by permitting nonradiative electron energy transitions at the surface. A shell reduces opportunities for nonradiative transitions by giving conduction band electrons an increased probability of directly relaxing to the valence band. The shell also neutralizes the effects of many types of surface defects.

The quantum dots may respond to various wave lengths of electromagnetic radiation, i.e., visible, invisible, ultrasound, microwaves. The quantum dots respond by emitting an electrical potential or fluoresce when exposed to electromagnetic radiation. The quantum dots may be made, or self-assembled, from CdSe and a shell of zinc gallium arsenide, indium gallium selenide, or cadmium telluride. Luminescent semiconductor quantum dots such as zinc sulfide-capped cadmium selenide may be covalently coupled to biomolecules for use in ultrasensitive biological detection. These nanometer-sized conjugates are water-soluble and biocompatible.

Quantum dots, organic quantum dots, or solar cells may be made from organic molecules such as organic nanocrystal solar cells, polymers, crystalline forms of carbon such as fullerenes, etc. In one embodiment, the crystalline form of carbon is fullerene. In one embodiment, the crystalline form of carbon is graphene. In one embodiment, the crystalline form of carbon is a carbon nanotube. Embodiments also include combinations of such crystalline forms of carbon.

Quantum dots may be coated with organic molecules, biocompatible proteins, peptides, phospholipids, or biotargeted molecules etc., or covalently attached to polyethylene glycol polymers (i.e., they may be PEGylated) to last longer. In one embodiment, hybrid quantum dots including but not limited to graphene/zinc oxide (ZnO) and reduced graphene oxide, or plasmonic nanoparticles coated with reduced graphene oxide, dextran-reduced graphene oxide, etc. may be used. In embodiments, ZnO is added to graphene quantum dots or to a combination of graphene particles and/or carbon nanotubes with a ZnO nanowire or nanorod using an electron gun. In embodiments, particularly those using light to stimulate the described particle, ZnO is useful because it prevents light reflecting off the particle surface, i.e., it serves as an anti-reflective coating, and provides a more efficient quantum dot compared with graphene or a carbon nanotube alone. ZnO additionally has the benefit of being an antibacterial compound and thus can be utilized for transporting biomolecules, such as DNA, along with other polymers; these may contribute a further therapeutic function and/or to the bio-compatibility of the disclosed complex.

In embodiments using a graphene and/or graphene oxide nanoparticle, optionally containing additional therapeutic or biocompatibility enhancing molecules such as peptides, etc., the application of the disclosed nanoparticle enhances neuronal growth. For example, the disclosed nanoparticle may be administered in response to brain and/or spinal cord injury, during ophthalmic LASIK surgery prior to closure of the corneal flap and/or after such surgery to stimulate neuronal growth, to neural tissue affected by Alzheimer's disease, or into the eye in genetic diseases of the eye, or ischemia leading to possible infarction and ischemic stroke, to damaged peripheral nerves, etc. to result in enhanced neuronal growth. The disclosed nanoparticle can be applied, e.g., on the corneal stroma, on an exposed wound, or on damaged nerves, as a drop or injected locally, or can be applied on or with a biocompatible substrate at a neuronal injury or infarction. For example, brain-derived neurotrophic factor (BDNF) may be administered locally in combination with the inventive nanoparticle/quantum dot embodiments. These may be further provided with agents that enhance neurite outgrowth, e.g., myelin basic protein (MBP), valproic acid, ketamine, donepezil hydrochloride, thymosin $\beta$10, thymosin $\alpha$1, choline acetyl esterase, etc. The therapeutic molecules may be contained in or on the quantum dot and enhance local neurite growth and promote neuron functional recovery.

These quantum dots, or devices containing quantum dots, are amenable to large scale production. They may be built from thin films, polymers of organic semiconductors. These devices differ from inorganic semiconductor solar cells in that they do not rely on the large built-in electric field of a PN junction to separate the electrons and holes created when photons are absorbed. The active region of an organic device consists of two materials, one which acts as an electron donor and the other as an acceptor. The short excitation diffusion lengths of most polymer systems tend to limit the efficiency of such devices. However, quantum dots can be used for cell membrane stimulation.

The quantum dots can be made to respond to various wavelengths of light (visible and invisible). In one embodiment they are coated with organic molecules. In one embodiment, they are completely organic. In one embodiment, they are PEGylated to last longer. In one embodiment, they are coated to be attracted to certain receptors or stay only on the cell surface.

In one embodiment, quantum dots, such as graphene nanoparticles, can be made into graphene transistor with a very large cut-off frequency, e.g., greater than 20 gigahertz, greater than 40 gigahertz, or up to 100 gigahertz. In one embodiment, wafer-scale, epitaxially grown graphene is used. Uniform and high-quality graphene wafers can be synthesized by thermal decomposition of a silicon carbide (SiC) substrate. The graphene transistor itself may use a metal top-gate architecture and a gate insulator stack involving a polymer and a high dielectric constant oxide. In embodiments, the gate length can be varied as desired. In one embodiment, the gate length is about 240 nanometers. In one embodiment, a one-atom-thick, two-dimensional metamaterial is produced by controlling the conductivity of sheets of graphene, a single layer of carbon atoms, by manipulating electromagnetic (EM) acoustic waves in the infrared spectrum. Applying direct voltage to a sheet of graphene by a ground plate parallel to a sheet of graphene, the conductivity of the graphene can be altered by varying the voltage or the distance between the ground plate and the graphene sheet. The sheet of graphene can have two areas that have different conductivities: one that can support an EM wave, and one that cannot support an EM wave. The boundary between the two areas acts as a wall, capable of reflecting a guided EM wave on the graphene. In embodiments, a third region may be created that can support a wave, surrounded by two regions that cannot support a wave, producing a "waveguide" that functions as a one-atom-thick fiber optic cable to carry signals. In another embodiment, another non-supporting region is added to bifurcate the waveguide, splitting it in two. In embodiments, as previously described, the one-atom-thick fiber optic cable may be used to stimulate cells and/or to detect changes in the stimulated cells.

Bioelectrical signals exist in all cells and play an important role in allowing the cells to communicate with each other. Quantum dots can facilitate these signal transmission between the cells, such as through cell membranes and their membrane potentials, thereby maintaining normal function in the tissue which include cell survival and growth, individually or collectively. Quantum dots can enhance regeneration of the cells. Quantum dots can enhance neural axons and enhance the wound healing process.

Cell activity relates to depolarization and re-polarization of the cell membrane. Quantum dots and/or semiconductor nanowires can regulate polarization and depolarization and thus enhance the action potential of the membrane. Lack of cell activity leads to cell atrophy. Similarly, loss of the cell membrane potential causes cell degeneration and atrophy. The therapeutic effects of particle administration are achieved by the effects that the particles exert on membrane potential when stimulated, e.g. light, photoelectrical, ultrasound, etc. In the eye and in the nervous system, particles can be stimulated (e.g., through the cornea, sclera or skull etc. for the brain, spinal cord, and nerves), thus enhancing or maintaining the cell membrane potential (e.g., nerve cell, glial cells, astrocytes, etc.). This process preserves the function of such cells (nerve cells, glial cells, astrocytes, etc.) by maintaining their membrane potentials, thus maintaining cell viability and function.

In one embodiment, the method and concept is applied to the eye. In one embodiment, the method and concept is applied to the brain and spinal cord nerve cells and axons. In this embodiment, the method is used to enhance or stimulate regrowth of nerve cells, axons, and/or other brain and spinal cord tissue. In one embodiment the method is applied to the heart.

In one embodiment, the effects of the particles on the cells can be enhanced by combining quantum dots with growth factors. Such growth factors are known to one skilled in the art, and include but are not limited to nerve growth factors, glial growth factors, placenta growth factor, etc. In one embodiment the effects of the particles on the cells can be enhanced by administering and/or regulating quantum dots essentially simultaneously with certain pharmaceuticals or agents, including but not limited to TAXOL®, carbonic anhydrase inhibitors, etc. Quantum dots and/or semiconductor nanowires, when activated by light, enhance drug penetration through the cell membrane. This can be used therapeutically in combination with many medications which may not penetrate the cell membrane easily because of their chemical structures. However, this concept can be used also in conjunction with antibiotics, antifungal agents, etc. to kill the organism that caused skin or mucosa ulcers resisting therapy.

The treatment can be done easily by topically applying the particles along with the appropriate medication and using light to activate the particles. The method of delivery to the eye may be by injection, eye drops, ointments, sprays or other applications to treat an optic nerve. The method of delivery to the brain may be by injection of the particles into cerebrospinal fluid, brain ventricles, intra-ocularly, or administration by nasal sprays or drops. The method of delivery to the skin or mucosa, e.g., nasal mucosa, is by spraying. Most of these applications avoid possible systemic side effects. The size of the particles allows them to easily diffuse into tissues. For neural applications other than the eye, quantum dots and/or semiconductor nanowires, either conjugated or associated with a drug, and/or administered without a drug or other agent, are administered by any route of delivery including but not limited to local, systemic, injection in the CNS, by nasal routes, e.g., spray, drops, to regulate the nasal olfactory nerve, or localized injection in the vicinity of the peripheral nerves or ganglions, etc.

In any of the disclosed embodiments, the nanoparticles may themselves be rendered capable of enhanced penetration into a cell by providing the nanoparticles in formulations, with agents, in composition, etc. that enhance cell penetration, having all requirements for therapeutic and biomedical uses such as biocompatibility, biodegradability (bioerodability and/or bioabsorbability), stability, and low toxicity. Such nanoplatform carriers include micelles, liposomes, dendrimers, and solid, lipid, metallic, semiconductors, peptide, and polymeric nanoparticles as subsequently described.

In one embodiment nanoparticles, e.g., quantum dots, are biocompatible or rendered biocompatible, e.g., by coating with a biocompatible polymer such as (poly)ethylene glycol (PEG) moieties, e.g., quantum dot-DNA-coated polymer, or any other polymer or combinations of polymers meeting these criteria. Exemplary such polymers also include, but are not limited to, polymers or co-polymers of poly(ester amide), poly-hydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate), and poly(3-hydroxyoctanoate), poly(4-hydroxyalknaote) such as poly(4-hydroxybutyrate), poly(4-hydroxyvalcrate), poly(4-hydroxyhexanote), poly(4hydroxyheptanoate), poly(4-hydroxyoctanoate) including 3-hydroxyalknnoate or 4-hydroxyalkanoate monomers, polyesters, poly(D,L-lactide), poly(L-lactide), polyglycolide, poly(D,L-lactide-co-glycolide), poly(lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives, poly(tyrosine ester) and derivatives, poly(imino carbonates), poly(glycolic acid-co-trimethylene carbonate), polyphosphoester, polyphosphoester urethane, poly(amino acids), polycyanoacrylates, poly(trimethylene carbonate) poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers (e.g., polyvinyl chloride), polyvinyl ethers such as polyvinyl methyl ether, polyvinylidene halides such as and polyvinylidene chloride, polyacrylonitrile, polyvinyl ketones, polyvinyl aromatics, such as polystyrene, polyvinyl esters such as polyvinyl acetate, copolymers of vinyl monomers with each other and olefins such as ethylene-methyl methacrylate copolymers, acrylonitrile-styrene copolymers, ABS resins, and ethylene-vinyl acetate copolymers, polyamides such as Nylon 66 and polycapro-lactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose pro-pionate, cellulose ethers, carboxymethyl cellulose, polyethers such as PEG, copoly(ether esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HEMA), hydroxypropyl methacrylamide, PEG acrylate (PEGA), PEG methacrylate, 2-ethacryloyloxyethylphosphoryl-choline (MPC) and n-vinyl pyrrolidone (VP), carboxylic acid bearing monomers such as methacrylic acid (MA), acrylic acid (AA), alkoxymethacrylate, alkoxyacrylatc, and 3-trimethylsilylpropyl methacrylate (TMSPMA), poly(styrene-isoprene-styrene)-PEG (SIS-PEG), polystyrene-PEG, polyisobutylene PEG, polycaprolactone-PEG (PCL-PEG). PLA-PEG, poly(methyl methlcrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone).

These also include nanoparticles, e.g., quantum dots, that are biocompatible or rendered biocompatible using peptides such as arginine-rich peptides, trans-activation transcriptional activator (Tat) peptides, biocompatible short peptides of naturally occurring amino acids that have the optical and electronic properties of semiconductor nano-crystals, e.g., short peptides of phenylalanine with particles consisting of both inorganic or organic materials. These also include nanoparticles, e.g., quantum dots, that are biocompatible or rendered biocompatible using biocompatible mono- or bilayers of phospholipid, liposomes, etc. These also include nanoparticles, e.g., quantum dots, that are biocompatible or rendered biocompatible using a specific agent and/or coating to the nanoparticles renders them specific, e.g., a protein coating to direct nanoparticles to attach to certain cell membranes, e.g., a member of a streptavidin-biotin pair, an immunoglobulin, a member of a cell-specific antibody-antigen pair, etc. These also include nanoparticles, e.g., quantum dots, to enter a cell to increase the membrane potential of the cells to which they come into contact, that are biodegradable either entirely or partially, that are non-biodegradable, and/or that are a combination of organic and metallic quantum dots. These include nanoparticles, nanotubes, nanowires, nanocrystals such as cadmium/selenium (Cd/Se), and particular types of each, e.g., graphene quantum dots, graphene-oxide quantum dots, graphene-zinc oxide quantum dots, graphene nanotubes, and/or carbon nanotubes.

As previously disclosed, all the above embodiments use compounds that are collectively termed nanoparticles. The nanoparticles with enhanced cell penetration may also be included in or coated on a bioabsorbable or non-bioabsorbable but biocompatible polymer structured or configured as a fiber, a tube, a substantially two-dimensional structure, or a three-dimensional structure to fit any anatomical or physiological site, configured as any desirable length or size to maintain its position with respect to an anatomical and/or physiological location, e.g., the eye. Upon activation, cells and adjacent tissue may undergo excitation, which is further tunable, e.g., parts of the polymer, e.g., the front and back sides of a substantially two-dimensional structure, having different particles to effect target cells, adjacent cells, etc.

Nanoplatforms may be developed of such carriers with both superior biocompatibility and superior penetrability. Pan et al., ACS Appl. Mater. Interfaces 5 (2013) 7042, disclose one such example of a family of silica crosslinked micelles that are biocompatible, luminescent, and stable; specifically, silica crosslinked pluronic F127 (difunctional block copolymer surfactant) micelles loaded with decyl capped silicon nanoparticles. Erogbogbo et al. (Integr. Biol. 5 (2013) 144) disclose another such example of a biocompatible silicon quantum dot F127 micelle with multiple silicon quantum dots incorporated into a micelle core having gold deposited on the nanostructure surface to provide light scattering properties facilitating imaging, while the silicon nanocrystals maintain photoluminescence.

Nanoparticles such as quantum dots that are coated on their surface with, encapsulated by, or otherwise associated with polymers, such as any of those previously described, have enhanced cell penetrating ability, as previously disclosed. Synthesis, fabrication, modifications, are possible, e.g., Tomczak et al., Progress in Polymer Science, 34 (2009) 393.

As one example, PEG grafted polyethylenimines (PEI) encapsulate and solubilize luminescent quantum dots through direct ligand-exchange reactions via positive charges and a proton sponge effect. PEG improves nanoparticle stability and biocompatibility, as previously disclosed, and reduces PEI toxicity to cells, as well as facilitating cell penetration. Duan and Nle, J. Am. Chem. Soc. 129 (2007) 3333.

As one example, nanoparticles such as quantum dots can be coated with proton-absorbing polymers, termed proton sponges, to facilitate siRNA delivery by enhanced cell penetration as well as other means. Yezhelyev et al., J. Am. Chem. Soc. 130 (2008) 9006.

As one example, the linear polysaccharide chitosan, in the form of beads, gels, sponges, membranes, scaffolds, etc. may be used as PEG-chitosan and/or folate-chitosan quantum dots. Rajan and Raj, I. Re. CH. E. 5 (2013) 145. As one example, folate conjugated, PEG-coated quantum dots specifically recognized and were internalized by folate receptors that were overexpressed in certain cancer cells, i.e., specific receptor-mediated cellular internalization. Song et al., Clincal Chemistry 55 (2009) 955. As one example, PEG-conjugated chitosan derivatives were synthesized and demonstrated narrow size distribution, good water solubility, low cytotoxicity. Lv et al., Chemical Papers 67 (2013) 1404.

Various coatings and encapsulation conditions, components, linkage types, etc., i.e., nanoparticle architecture, can assist in regulating nanoparticle penetration effects and parameters under various conditions. Smith et al., Advanced Drug Delivery Reviews 60 (2008) 1226. As one example, at least two of the same or different, i.e., hybrid, nanoparticles such as quantum dots can be encapsulated in amphiphillic block copolymer micelles that are crosslinked and thus form a shell surrounding the plurality of nanoparticles. Kim and Taton, Langmuir, 23 (2007) 2196. As one example, nanoparticles such as quantum dots can be encapsulated in carboxylated Pluronic (i.e., poly(ethylene oxide) (PEO) and poly(propylene oxide) (PPO) with a PEO-PPO-PEO structure) 127 triblock, forming a polymeric micelle with efficient cell penetration. Liu et al. Theranostics 2 (2012) 705.

Nanoparticles such as quantum dots may be conjugated with various physiologic biomolecules to enhance or facilitate cell penetration. Examples of such compounds include, but are not limited to, carbohydrates, cholesterol, glutathione (e.g., taking advantage of amino functionalities), collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, and biotin, proving good stability and cell viability, e.g., Jin et al., Int. J. Mol. Sci. 9 (2008) 2044.

One example of this enhanced penetration is quantum dots conjugated or otherwise associated with cell penetrating agents such as cell penetrating peptides (CPP) and activatable-cell penetrating peptides (ACPP).

Cell-penetrating peptides (CPP) and activatable cell-penetrating peptides (ACPPs) that are labeled with fluorescent polycationic CPP coupled by a cleavable linker to a neutralizing peptide have been developed and utilized to visualize tumors during surgery. ACPP conjugated to dendrimers (ACPPDs) and gadolinium chelates can allow MRI visualization of whole body tumors, permitting therapy if the magnetic or gadolinium nanoparticles are labeled with ACPPD.

One embodiment is a composition of a nanoparticle such as a quantum dot that is conjugated to an activatable cell penetrating peptide (ACPP). The quantum dot or nanoparticle may be cleavably conjugated to the ACPP by, e.g., a linker (e.g., ethylene glycol moiety, PEG moiety). In one embodiment, the quantum dot or nanoparticle is labeled with a label such as a fluorescent moiety, chemiluminescent moiety, etc. In one embodiment, the ACPP is labeled with a polycationic cell-penetrating peptide (CPP). ACPP and CPP may be naturally-occurring or artificially constructed protein segments (<30 amino acids) rich in arginine, lysine, cysteine, histidine, ornithine, etc.; preferably α-helices and about 17-amino acids. The ACPP and CPP may include a penetration accelerating peptide sequence (Pas) or an INF7 fusion peptide sequence. CPP and/or ACCP can be linked to cargoes either covalently or noncovalently, or can use block copolymers to form various kinds of micelles. Liu et al., endocytic trafficking of Nanoparticles Delivered by Cell-penetrating peptides Comprised of Nona-arginine and a Penetration Accelerating Sequence, PLOS ONE 8 (2013) e67100; Liu et al., Intracellular Delivery of Nanoparticles and DNAs by IR9 Cell-penetrating Peptides, PLOS ONE 8 (2013) e6405; Liu et al., Cell-Penetrating Peptide-Functionalized quantum Dots for Intracellular Delivery, J. Nanosci Nanotechnol 10 (2010) 7897; Liu et al., Cellular Internalization of Quantum Dots Noncovalently Conjugated with Arginine-Rich Cell-Penetrating Peptides, J. Nanosci Nanotechnol 10 (2010) 6534; Xu et al., Nona-Arginine Facilitates Delivery of Quantum Dots into Cells via Multiple Pathways J. Biomedicine and Biotechnology volume 2010, Article ID 948543, 1-11. Exemplary but non-limiting ACPP and CPP include transportan, penetratin, TAT, VP22, MAP, KALA, ppTG20, proline-rich peptides, MPG-derived peptides, Pep-1, nona-arginine, and the carboxy-terminal tail of TFPI-2, polyproline helices having cationic amino acids and/or cationic-functionalized amino acids within the helix (e.g., guanidinium-functionalized proline), a synthesized oligoarginine cell penetrating peptide (based on the HIV-1 Tat protein motif) bearing a terminal polyhistidine (His8) tract facilitated transmembrane quantum dot delivery (Delehanty et al., Bioconjug Chem 17 (2006) 920). Other cell penetrating agents include oligoguanidinium scaffolds, cationic-functionalized calixarenes, or cyclodextrins, e.g., arginine-functionalized calixarene). For example, CPP comprising a INF7 fusion peptide and nona-arginine produces IR9/QD and IR9/DNA complexes, IR9, IR9/QD and IR9/DNA. Handbook of Cell Penetrating Peptides, Langel (Ed) 2007 (Second Edition) CRC/Taylor & Francis).

One example of this enhanced penetration uses genes capable of modifying cell polarization and, potentially, creating an action potential upon specific prompts. Such genes encode, e.g., a cell membrane ion channel protein or transporter, e.g., a G protein-coupled receptors. Specific examples include genes encoding opsin family members such as rhodopsin, photopsins, halorhodopsin, genes encoding neurotransmitters such as glutamate/aspartate transporters, GABA transporters, glycine transporters, monoamine transporters such as dopamine transporter, norepinephrine transporter, serotonin transporter, and vesicular monoamine transporters. Upon exposure to light of a specific wavelength, quantum dots coated or otherwise associate with organic or non-organic biodegradable compounds may be used. Such agents include silicon, porous silicon, aliphatic biodegradable polymers, etc. the quantum dots range from about 1 nm to 200 nm in one embodiment, and range from about 1 nm to 10 nm in another embodiment. The genes, once in the nucleus, undergo transcription and translation into the specific proteins or protein channels. This embodiment is described in, e.g., Narayanan et al., Scientific Reports 3, article number 2184, doi: 10.1039/srep02184 describing a mimic of microtubule mediated protein transport using designed biotinylated peptides with microtubule-associated sequences (MTAS) and a nuclear localization signaling (NLS) sequence, conjugating with streptavidin-coated CdSe/ZnS quantum dots to enhance endosomal escape and promote targeted nuclear delivery into mesenchymal stem cells by microtubules. This embodiment is also described in Ho et al., J. Vis Exp. 30 (2009) 1432, describing a specific quantum dot-labeled DNA complex (Cy5) that forms by electrostatic self-assembly, facilitating DNA cellular update and protecting against DNA degradation and monitored using combined quantum dot-FRET and microfluidics.

Agents may be linked to, associated with, complexed or conjugated with nanoparticles using linking agents and methods known in the art. These include, but are not limited to, the following: amino groups, carboxyl groups, S—S deprotected sulfhydril groups in biomolecules, e.g., bis (succinimide derivative conjugation, maleimidosuccinimide/succinimidylpyridyldithio/-halosuccinimide derivative conjugation, N-(4-maleimido-phenyl) isocyanate conjugation, carbodiimide conjugation, sulfosuccinimidylsuberyl linkage, synthetic tripyrrole-peptide linkage, NHS-esters and other esters, etc. Cleavage of the linkers by specific proteases, e.g., matrix metalloproteinase-2, dissociates the polyanion and enables arginine-rich CPPs to enter cells.

Figure 5A:
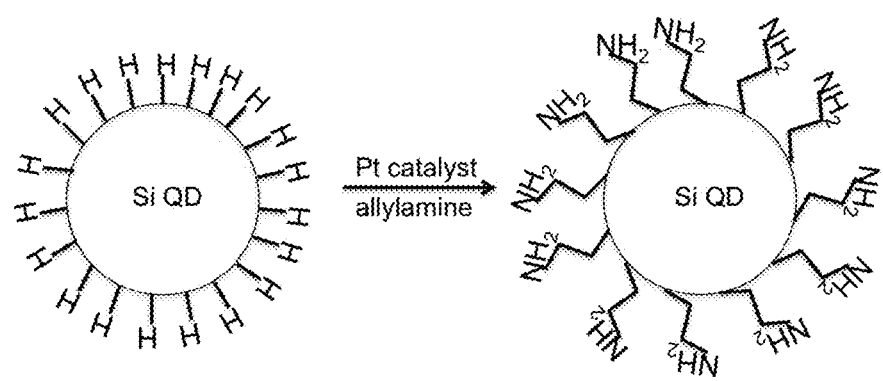
FIGS. 5A-B is a schematic structure of an activated biodegradable silicone or luminescent quantum dot.
Figure 5B:
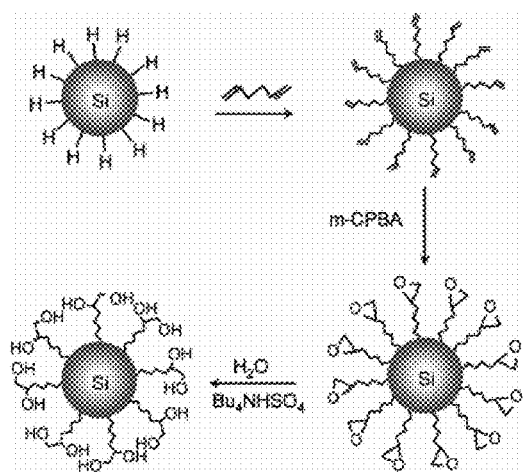

FIGS. 5-7 show various nonlimiting embodiments of selected structures. FIGS. 5A-B schematically show an activated biodegradable silicone or luminescent quantum dot. FIG. 6 schematically shows synthesis of a cell-penetrating peptide (CPP). FIG. 7 shows the chemical structure of an activated fluorescent dye.

In one embodiment, the inventive method is used in a patient with a neurological disorder. While described in detail for use in a patient with epilepsy, which is a common neurological disorder requiring treatment, the inventive method is not so limited and encompasses any neurological disorder of the central and/or peripheral nervous system. Epilepsy is thus used an exemplary but non-limiting embodiment of use of the method.

Epilepsy is a chronic condition that transiently affects about 50 million individuals. It is not a single disorder, but instead is a group of syndromes with vastly divergent symptoms. Its unifying and diagnostic feature is episodic abnormal electrical activity in the brain that results in seizures. These seizures are transient, recurrent, and unprovoked; signs and/or symptoms of abnormal, excessive, or synchronous neuronal activity in the brain. All seizures involve loss of consciousness; types of seizures are characterized according to their effect on the body. These include absence (petit mal), myoclonic, clonic, tonic, tonic-clonic (grand mal), and atonic seizures.

Some forms of epilepsy are confined to particular stages of childhood. In children, epilepsy may result from genetic, congenital, and/or developmental abnormalities. In adults over 40, it may result from tumors. At any age, it may result from head trauma and central nervous system infections. Post-traumatic epilepsy (PTE) is a form of epilepsy that results from brain damage caused by physical trauma to the brain: traumatic brain injury (TBI). An individual with PTE suffers repeated post-traumatic seizures (PTS) more than a week after the initial injury. PTE can also occur after infectious diseases involving the CNS or peripheral nerves.

Epilepsy is usually controlled, but not cured, with medication, although surgery is sometimes needed. Therapeutic agents include (a) sodium channel blockers (voltage dependent), (b) calcium channel blockers (T-type), (c) potentiators of GABA (inhibitory), and (d) those that decrease excitatory transmission (glutaminic).

Some medication, administered daily, may prevent seizures altogether or reduce their frequency. Such medications, termed anticonvulsant drugs or antiepileptic drugs (AEDs), include valproate semisodium (Depakote, Epival), valproic acid (Depakene, Convulex), vigabatrin (Sabril), and zonisamide (Zonegran). A problem is that all have idiosyncratic and non-dose-dependent side effects. Thus, one cannot predict which patients on a therapeutic regimen will exhibit side effects or at what dose.

Some medications are commonly used to abort an active seizure or to interrupt a seizure flurry. These include diazepam (Valium) and lorazepam (Ativan). Drugs used only in the treatment of refractory status epilepticus include paraldehyde (Paral), midazolam (Versed), and pentobarbital (Nembutal).

Bromides, the first of the effective anticonvulsant pure compounds, are no longer used in humans due to their toxicity and low efficacy.

Palliative surgery for epilepsy is intended to reduce seizure frequency or severity. For example, a callosotomy or commissurotomy is performed to prevent seizures from generalizing, i.e., from being transmitted to the entire brain, which results in loss of consciousness Vagus nerve stimulation (VNS) controls seizures with an implanted electrical device, similar in size, shape, and implant location to a pacemaker. The implanted VNS device connects to the vagus nerve in the neck and is set to emit electronic pulses to stimulate the vagus nerve at pre-set intervals and milliamp levels. About 50% of individuals with an implanted VNS device showed significantly reduced seizure frequency.

The Responsive Neurostimulator System (tRNS), in clinical study prior to regulatory approval, is a device implanted under the scalp with leads implanted either on the brain surface or in the brain close to the area where the seizures are believed to start. At the outset of a seizure, small amounts of electrical stimulation are delivered to the brain to suppress the seizure. The RNS system differs from the VNS: the RNS system is patient responsive in that it directly stimulates the brain, whereas the VNS system provides physician-determined pre-set pulses at predetermined intervals. The RNS system is designed to respond to detected signs that a seizure is about to begin and can record events and allow customized response patterns that may provide a greater degree of seizure control.

One class of therapeutic agents for treating epilepsy are the carbonic anhydrase inhibitors, but all have undesirable side effects.

Acetazolamide (Acz), a known inhibitor of carbonic anhydrase, is one such agent. It prevents hypoxic pulmonary vasoconstriction (HPV) and thus is also used to treat altitude sickness, glaucoma, and benign intracranial hypertension. Acetazolamide, however, affects kidney function because it reduces NaCl and bicarbonate reabsorption in the kidney proximal tubule. The reduction results in a mild diuretic effect, although it is partially compensated by the kidney distal segment and the metabolic acidosis produced by the bicarbonaturia. Methazolamide, also a carbonic anhydrase inhibitor, is longer-acting than acetazolamide with fewer kidney effects. Dorzolamide, a sulfonamide and topical carbonic anhydrase II inhibitor, reduces the elevated intraocular pressure in patients with open-angle glaucoma or ocular hypertension that are insufficiently responsive to beta-blockers. Inhibition of carbonic anhydrase II in the ciliary processes of the eye decreases aqueous humor secretion, presumably by slowing the formation of bicarbonate ions with subsequent reduction in sodium and fluid transport. Topiramate is a weak inhibitor of carbonic anhydrase, particularly subtypes II and IV. It is a sulfamate-substituted monosaccharide that is related to fructose. In is approved in the U.S. as an anticonvulsant to treat epilepsy, migraine headaches, and Lennox-Gastaut syndrome. Its inhibition of carbonic anhydrase may be sufficiently strong to result in clinically significant metabolic acidosis.

Acetazolamide and other calcium-inhibiting sulfonamides increase intracellular pH and relax mesenteric arteries preconstricted with norepinephrine. Calcium inhibitors and/or the intracellular alkalinization activate a calcium-dependent potassium channel, resulting in hyperpolarization of the vascular smooth muscle cell, reduction of voltage-dependent calcium channel activity, decreased intracellular calcium, and vasorelaxation.

Spreading depression (SD) is a pathophysiologic event characterized by depressed EEG activity and a change of the direct current potential as an indicator of a short-lasting cell membrane depolarization. It may be induced by a variety of cortical stimuli, including potassium chloride or glutamate application, and electrical or mechanical stimulation; it also occurs secondary to ischemia. It is accompanied by severe changes in ion homeostasis and water shifts from the extracellular to intracellular space, mirrored by changes of electrical impedance and direct current (DC) potential. The area of depolarization spreads along cortical tissue like a wave, moving away from the initiation site toward the periphery, and propagates with an estimated velocity of 3 mm/min. Electrical measurements from the cortex surface show negative deflection of the DC potential, lasting 1 to 2 minutes, combined with EEG suppression. Under normoxic conditions, SD is not followed by permanent neuronal damage, and the depressed neuronal activity is compensated by increased glucose metabolism and blood flow during the repolarization phase. The cell membrane repolarization requires an enormous metabolic effort and is compensated by increased glucose metabolism and increased blood flow.

Serotonin homeostasis, regulated by serotonin receptor 1A (Htr1a), is required for normal serotonin levels. Htr1a also mediates autoinhibition of serotonin production; excessive serotonin autoinhibition is associated with sporadic autonomic dysregulation and death. Tryptophan, a serotonin precursor, increases serotonin production. Administration of the selective Htr Ia antagonist WAY100635 completely shuts down serotonin-induced neuron impulses, resulting in apnea preceded by bradycardia; both lung function and heart function were affected.

Spreading depression (SD) has been extensively studied and is likely an important mechanism in several human diseases. Cerebral hemodynamics, i.e., cerebral blood volume and water changes, were assessed by high-speed MRI during potassium-induced spreading depression. MRI images, and brain voltage readings, were used to determine apparent diffusion coefficients over time that correlated with potassium flux along the cortex. Acetazolamide treatment resulted in vasodilation and arrested spreading depression.

Diffusion-weighted imaging is highly sensitive to slowing water proton translations early in the ischemic episode, i.e., within minutes. MR imaging measured the ADC of brain water decreases by 30% to 60%, and recent findings suggested significant apparent diffusion slowing (ADC decreases) in stroke results predominantly due to cellular swelling and reflects a shift of relatively faster translating extracellular water protons into a more hindered intracellular environment. It has been shown that when the $Na^+/K^+$ pump is disabled by intraparenchymal ouabain, the ADC decreases. This supports a link between altered ion homeostasis and alteration in ADC. There is a relation between membrane polarization and diffusion as measured by the ADC. Failure of the transmembrane ion pumps and subsequent loss in cell membrane potential is immediately followed by disruption of ion homeostasis. The resulting ionic imbalance causes an osmotically driven flow of water into the cells. MR imaging indicates the subsequent cell swelling with restricted extracellular or intracellular diffusion, and increased extracellular tortuosity, reduces the ADC.

The concept of cell preservation by quantum dot administration and treatment applies to the above these diseases and reduces degeneration of all brain cells (nerve cells, glial cells, etc.).

Particles are useful in providing repeated electric pulses either to the brain, spinal cord, or isolated nerve cells that are involved with various neural disorders. In disorders involving these regions low level brain, spinal cord, etc. neural pulses are not passing through for one reason or another, e.g., synapses, scar, misdirection, etc., and are released either as a giant pulse or can circuit back and forth until the membrane potential is completely exhausted. Therefore a pulsed stimulation by an external source, such as light or electric pulses applied to the brain, ventricles, spinal cord, cerebrospinal fluid, having quantum dots and/or semiconducting nanowires would eliminate an avalanche of the pulses in posttraumatic epilepsy, restless leg syndrome, spinal cord epilepsy, etc. A version of this concept could be potentially used to modify brain waves needed for sound sleep, alleviation of depression, etc. Stimulation of the olfactory nerve can enhance neuronal regeneration in the brain in aging adults or in Alzheimer's disease or slow its progression.

In one embodiment the method includes tunability or adjustment of duration and repetition rate or frequency of stimulation in response to cell activity. For example, saccadic eye movements are generated by underlying activity in the cortical cells of the brain, and tend to reflect a summation of the polarization and depolarization of brain cells during diurnal activity and sleep. These depolarization/repolarization or "pulse" frequencies may be influenced by various physiological and, potentially, pathological processes in the brain, monitored to diagnose abnormal patterns in the underlying activity, and altered by therapeutic stimulation of the particles to counteract abnormal activity. Under normal conditions, intrinsic electrical stimulation of the frontal eye fields elicits voluntary or so-called pursuit eye movements, but includes saccadic movements having a frequency of about 27 Hz to 36 Hz during diurnal activity, and up to about 40 Hz to 45 Hz during the rapid eye movement (REM) stage of sleep, Rio-Portilla et al., Int' J. Bioelectromagnetism 10(4) (2008), pp. 192-208. Under abnormal conditions such as epilepsy, etc., pulse avalanches in the brain can effect these saccadic movement frequencies and produce abnormal movement reflecting the underling abnormal condition. Saccadic movement frequencies may range from about 1 Hz to 1000 Hz. A frequency below 20 Hz or above 60 Hz may indicate an abnormality.

In one embodiment the pulse frequency of brain neuronal activity is evaluated using the observed frequency of saccadic eye movements. The observed frequency may be measured using known eye tracking units during diurnal activity and/or an electro-oculogram during both diurnal activities and sleep, i.e., when the eye is potentially closed. The evaluated condition may be used to determine when therapeutic light pulses are to be delivered to particles administered to the eyes, the brain, etc. In one embodiment the particles are conjugated with membrane ion channel activators, as described above.

In one embodiment an eye tracker is used in combination with a light source to therapeutically stimulate particles provided to the eye. A small digital camera may be mounted on the patient's head, e.g., in eyeglasses, to obtain video images of the eye and transmit the images to a computer. The video images may include reflected infrared, visible, and/or ultraviolet light reflected from the eyes and captured by the camera. The video images may be analyzed to determine the average frequency of saccadic movement of the eye for an interval of time, and to compare the average frequency to one or more criteria for apparently normal or abnormal brain function. The light source, e.g., LED or low powered laser, may be activated to stimulate the particles administered to the brain or inhibit an action potential response in the brain at a predetermined frequency using physician-determined pulses of light for predetermined durations at predetermined repetition intervals. The light source in one embodiment emits light that is reflected into the eye through a stationary or rotating mirror positioned within the visual field of the eye. This system is designed to respond to detected signs that a seizure is about to begin, permitting customized response patterns that may provide a degree of seizure control.

In one embodiment equipment similar to that previously described may be used to provide enhanced vision to a patient, e.g., a patient having damaged or diseased outer photoreceptor segments. A small digital camera may be mounted on the patient's head, e.g., in eyeglasses, to obtain video images. In this embodiment, however, the video images are obtained from the viewpoint and across the visual field of the patient, i.e., are images of the external environment, rather than of the eye itself. The images may approximate those viewable using only visible light or be hyperspectral images including infrared, visible, and/or ultraviolet wavelengths. The light source, emitting at least one wavelength of light, may be activated to stimulate the particles administered to the eye in a pattern representative of the video image. For example, color images are typically represented as a combination of images in three primary colors, but may be converted to a combination of images in only two colors or a single image varying only in relative intensity. Particles adapted to specifically bind to one or more of the S-cone, M-cone, and L-cone photoreceptor cells may be activated by pulses of different wavelengths to stimulate the perception of colors. Particles adapted to bind to photoreceptor cells generally, rods, or alternate targets in signaling pathway such as photoreceptor cell body, bipolar ganglion cells, amacrine cells, and Muller cells, may be activated by pulses to stimulate the perception of intensity, i.e., to simulate vision under low-light conditions. In one embodiment, placement of the photovoltaic particles in the membrane mimics the naturally-occurring amphiphilic transmembrane proteins, which have hydrophobic membrane-spanning domain(s) that interact with fatty acyl groups of the membrane phospholipids and hydrophilic domains extending into the aqueous medium on each side of the membrane. An embedded nanoparticle, e.g. with the metal portion inside the cell, acts as a photovoltaic cell where the electric current varies with the rate of photon absorption. Illumination of embedded particles generates a photovoltage that reduces the potential across the cell membrane by about 10 mV. Such membrane depolarization causes enough voltage-sensitive $Na^+$ ion channels to open to generate an action potential that travels down the axon.

The stimulated photoreceptors will transmit the stimulated pulses to the optic nerve and to the brain, where the pulses will be interpreted as images by the visual cortex. The light source may be a complex source, e.g. a small scale LCD or OLED screen positioned in front of the eye, e.g. as a lens of glasses, or to reflect from a stationary mirror positioned within the visual field of the eye. The light source may alternately be single or multiple wavelength scanned-beam system, using one or more discrete light sources, e.g., LEDs or low power lasers, and a rotating mirror to stimulate, pixel by pixel, the photoreceptor cells, the outer segment of the retina, the inner segment of the retina, etc., similar to the manner in which an electron gun excites the phosphors of a cathode ray tube television. The computer may manipulate the image size, intensity, contrast, etc. to improve visibility, as well as to translate between detected wavelengths of light, e.g., the typical red, green, and blue color-filtered detectors employed in Bayer filtered sensors or multi-sensor imaging blocks, and emitted frequencies of light emitted at the appropriate wavelengths to stimulate the one or more types of particles. The particles in the retina can respond to both detection of IR light that is reflected from a real object that acts on the particles, or detection of IR light that is captured by a digital camera and is reemitted by a head-mounted device, with the camera and processor able to amplify the pulse frequency, energy, etc.

In one embodiment an eye tracker is used in combination with a light source to therapeutically stimulate particles provided to the brain. For example, a controller may analyze output from pairs of electrodes placed around an eye to determine the average frequency of saccadic movement of the eye for an interval of time, and to compare the average frequency to one or more criteria for apparently normal or abnormal brain function. Particles administered to the brain, and illuminated by the light source through a window in the skull, an implanted light guide, a fiber optic material, etc., or alternatively using an LED implanted under the skull that is remotely activated to produce the light source, may be stimulated at a predetermined frequency using physician-determined pre-set pulses of light at predetermined intervals. The predetermined frequency and predetermined intervals may be selected to simulate normal electrical activity of the brain to prevent or dampen the effect of abnormal activity generated in, e.g., an epileptic seizure, etc. Alternatively a wavelength can be used that suppresses the activity of those neurons and blocks the acute process for the desired time, and then can one start the process with a normal frequency of stimulation. This embodiment may be used to modify the electrical pulses and involuntary movements in Parkinsons disease.

In one embodiment a controller is combined with a light source and a window in the skull, an implanted light guide, a fiber optic device, etc., to create a form of pacemaker that may be externally controlled. In one embodiment, by therapeutically stimulating the brain at pulse frequencies such as those found in REM sleep, the device may help the patient to achieve sleep or diminish a disturbed mental state such as depression, aggression, psychosis, etc. The system may be adapted to be remotely controlled by a physician or medical staff and include a wireless receiver or transceiver. Such a system may be fully implantable or have an external controller and battery unit. The system may also be adapted to be controlled by the patient, and may include a governing system limiting the frequency and/or duration of self-activation.

In one embodiment such a stimulation system is adapted for use as a pacemaker for the heart, controlling the frequency of activation of the sinoatrial node and/or atrioventricular node to control cardiac contractions. For example, particles conjugated with membrane ion channel activators may be coated on or included in fiber optics implanted within the right ventricle.

A physician may select specific properties and emission frequencies to selectively regulate polarization in specific sites and for specific results. Thus, the particles are tunable to provide desired properties; for example, they may be size specific, current specific, patient specific, disease specific, activation specific, site specific, etc.

As one example, particles provided throughout the retinal layers may be selectively regulated to normalize polarization and/or reduce or prevent repolarization, depolarization, and/or hyperpolarization. As another example, selected particles may be administered to selected sites and selectively regulated (e.g., temporally, spatially, activationally, etc.) to result in different effects to fine-tune a desired outcome. More specifically, a patient's progress may be monitored after a slight regulation and, if warranted, further regulation may be administered until a desired outcome is obtained. For example, a patient with muscle tremors may be treated with the inventive method for a duration, extent, activation energy, etc. to selectively repolarize striated muscle cells until a desired effect is reached.

In one embodiment a patient with cardiac disease or dysrhythmia, including cardiac arrhythmia, is treated with a biocompatible quantum-dot/gene conjugate coated or otherwise containing anti-cardiac muscle antibodies. The quantum dots are administered by intravenous or intracardial routes, e.g., during a cardiac catheterization procedure. Once administered, cardiac cells are then be stimulated with, e.g., an implanted fiber optic device connected to a control system and light generator to stimulate or regulate the cardiac rate as needed. The fiber optic device and its controller are implanted under the skin of the chest, and function similarly to a cardiac pacemaker. In one embodiment, the device and its controller are programmed to automatically initiate so that a pulse is obtained upon cardiac arrest. This embodiment eliminates need for an external defibrillator, which provides indiscriminate electrical action and thus is traumatic.

In embodiments, the disclosed complex comprises nanoparticles other than quantum dots; these include nanowires, nanorods, etc. In embodiments containing a biomolecule, the complex comprises at least a first nanoparticle and a second nanoparticle where the first and the second nanoparticles absorbs energy at different wavelengths, and thus are activated by different energy wavelengths, e.g., light. This embodiment permits control of the activity of the complex, e.g., selective activation using different energy wavelengths, providing further control of the physiological function of excitable cells. In embodiments comprising a biomolecule that targets the complex to a specific location, tissue, cell, etc., the complex comprising multiply excited particles can be used for diagnostic identification. For example, it can be used to identify a specific cell type.

In one embodiment, the particles are mixed into or with a biocompatible fluid that may include one or more types of indirectly associated (non-conjugated) biomolecule. In another embodiment, the particles are in the form of beads or spheres. In another embodiment, the particles are provided as a film. In another embodiment, the particles are drawn and provided as fibers. In any of these embodiments, the particles are provided to a patient by injection to other minimally invasive techniques known to one skilled in the art.

Upon administration, the particles are disseminated and/or located intracellularly (within a cell), intercellularly (between cells), or both intracellularly and intercellularly. They may be administered in a number of ways. With respect to the eye, they may be injected through the retina, under the retina superiorly, over the fovea, through the outer plexiform layer down to the fovea, into the vitreous cavity to diffuse through the retina, etc. The procedure permits particles to be located at any site including the macula, that is, the particles may be directly on the macula, directly on the fovea, etc. distinguishing from procedures requiring electrodes to be located beyond the macula or beyond the fovea so as not to block foveal perfusion. The procedure does not require major invasive surgery and is only minimally invasive, in contrast to procedures that involve surgical implantation of an electrode or photovoltaic apparatus. The procedure locates particles diffusively substantially throughout the eye, or selected regions of the eye, in contrast to procedures in which an electrode or other device is located at a single site. Thus, the site of treatment is expanded with the inventive method. In this way, the particles locate within excitable cells, such as the retina, macula, etc. using an ocular example, and also locate between these excitable cells, and are thus dispersed substantially throughout a region of interest. Particles not located as described are handled by the retinal pigment epithelium.

In one embodiment, and as an example, stem cells are grown or incubated in the presence of antibody and gene-coated magnetic particles, e.g., quantum dots, to permit their digestion of quantum dots or attachment of the quantum dots to the cells. In one embodiment, and as an example, stem cells are grown or incubated in the presence of antibody and channel protein gene coated magnetic particles, e.g., quantum dots, to permit their digestion of quantum dots or attachment of the quantum dots to the cells. After administration of stem cells and quantum dots in the desired area or in the circulation, a fiber optic light and a magnet are placed at the intended area to attract and guide the magnetic quantum dots to that area.

In one embodiment the stem cells and quantum dots are injected in the vitreous cavity, in or under the retina, combined with placement of the magnet over or near the retina on the back of the eye. This embodiment directs the stem cells and quantum dots to the specific areas of the retina, optic nerve, etc.

In one embodiment the stem cells and quantum dots are injected in the cerebrospinal fluid, brain, spinal cord, or tissue near a peripheral nerve. A light and a magnet are placed in or near the damaged areas to direct the stem cells and quantum dots to the degenerative areas of the brain, spinal cord, or peripheral nerve.

In one embodiment the stem cells and quantum dots are injected in the circulation as needed and are captured with an external magnet placed in a desired area.

In each of these embodiments and example, the stem cells and quantum dots can be stimulated as described with light.

Continuing to use the eye as a non-limiting example, the particles migrate through spaces of retinal cells and distribute through retinal layers, including the RPE. To even more widely disperse particles throughout the retina, they may be sprayed over the retina. In one embodiment, they may be delivered and distributed throughout the retinal layers by a spraying or jetting technique. In this technique, a pressurized fluid (liquid and/or gas) stream is directed toward a targeted body tissue or site, such as retinal tissue, with sufficient energy such that the fluid stream is capable of penetrating the tissue, e.g., the various retinal layers. In applications, the fluid stream, which may be a biologically compatible gas or liquid, acts as a carrier for the particles. By way of example, the spraying technique has been used in cardiac and intravascular applications for affecting localized drug delivery. The teaching of those applications may be applied to the delivery of the particles to the retina. For example, U.S. Pat. No. 6,641,553 which is expressly incorporated by reference herein, discloses pressurizing a fluid carrier having a drug or agent mixed therewith and jetting the mixture into a target tissue.

It will also be appreciated that other agents may be included in the fluid in addition to the particles. These other agents include, but are not limited to, various molecules, drugs that have stimulatory or inhibitory activity (e.g., protein drugs, antibodies, antibiotics, anti-angiogenic agents, anti-prostaglandins, anti-neoplastic agents, etc.), vectors such as plasmids, viruses, etc. containing genes, oligonucleotides, small interfering RNA (sRNA), micro-RNA (miRNA), etc.

In one embodiment, quantum dots conjugated or otherwise associated with a molecule or biomolecule are delivered to an eye to enhance functional recovery of an at least partially functional retinal cell in a patient in need of such treatment. This embodiment of the method may be in addition to, or in place of, the method of regulating membrane polarity using the introduced quantum dot previously described. The quantum dot-biomolecule conjugate or particle may be provided to a retinal cell cytoplasm or a retinal cell nucleus, with injection or other introduction means into the subretinal space, into the retina itself, into the macula, under the macula, into the vitreous cavity with vitreous fluid present, and/or into the vitreous cavity with vitreous fluid absent. The quantum dots conjugated or otherwise associated with a vector carrying a protein or other molecule capable of modifying genes in retinal cell provides gene therapy. In one embodiment, racking means (e.g., sensors or other signals) associated with the complex are used to monitor location, stability, functionality, etc. of the complex.

In one embodiment the retinal or other cell so modified by the method contains a light-sensitive protein that itself may be excited directly by light of a specific wavelength, or in an alternative embodiment, be excited by light of a different wavelength or produced by the quantum dot (e.g., fluorescence) after the quantum dot is excited upon exposure of light. For example, if the modified genes of the cell produce halorrhodopson, then the quantum dots to which the halorhodopsin-encoding gene were associated can be excited to then activate the halorhodopsin to silence the cell. If the modified genes of the cell produce channelrhodopsin, then the quantum dots to which the channelrhodopsin-encoding genes were associated can enhance an action potential. As known to one skilled in the art, channelrhodopsins, a family of proteins, function as light-gated ion channels in controlling electrical excitability among other functions. As known to one skilled in the art, halorhodopsin is a light-activated chloride-specific ion pump. When quantum dots are combined with channelrhodopsins or halorrhodopsons, quantum dots enhance the effects of these proteins, and result in enhanced cell polarization responsive to light stimulation.

In one embodiment, quantum dots conjugated or otherwise associated with a molecule or biomolecule are delivered to the heart to enhance functional recovery of an at least partially functional heart cell in a patient in need of such treatment.

In one embodiment of monitoring, a video camera receives an image of the external environment that is projected into an eye containing the functional, excitable retinal cell to be treated. For example, after initial administration of the quantum dots to the eye, a camera mounted on or in the eyeglasses records and produces a digitized image of the external environment, which is then transmitted to a small computer mounted on the glasses. The picture can be recreated on an LCD using a diode array. This image, in turn, is projected through the pupil, onto the retina containing quantum dots to stimulate rods and cones. This process may be optionally repeated to determine the extent or degree to excite the quantum dots and/or to achieve the desired cell polarization state by evaluating retinal function, e.g., by electroretinogram or other methods known to one skilled in the art.

In one embodiment, the eye imaging method, e.g., OCT, confocal microscopy, provides a method of tracking the quantum dots in cells, e.g., stable cells such as neurons.

In one embodiment, the treated cells are restored to normal polarization by treatment using the quantum dots; and concomitantly, the cells are treated with a biological moiety conjugated to the quantum dots to relieve, restore, ameliorate, or treat a functional condition of the retinal cell, e.g., a retinal genetic disease. In one embodiment, the biologically active conjugate is biologically active after the quantum dot ceases to be functional. In one embodiment the quantum dot is active after the biologically active conjugate ceases to be functional.

Figure 3:
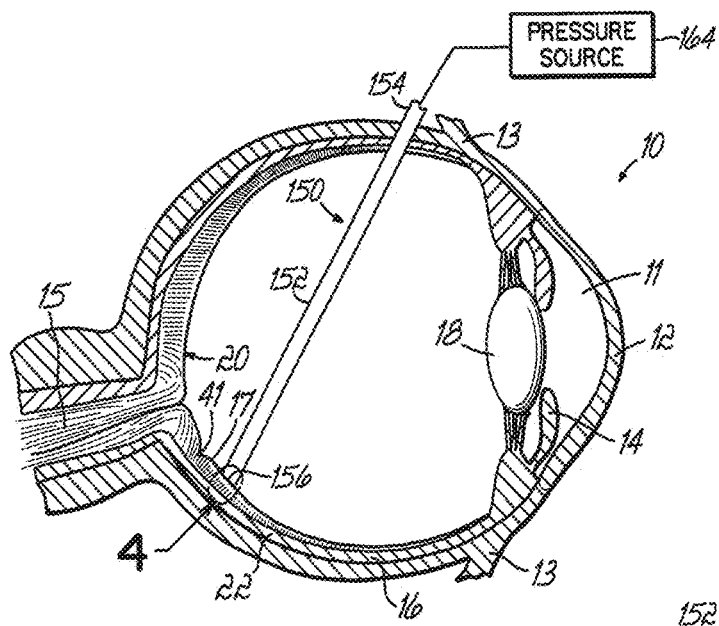
FIG. 3 shows the eye of FIG. 1 with a cannula delivering particles to the retina in accordance with one embodiment of the invention.
Figure 4:
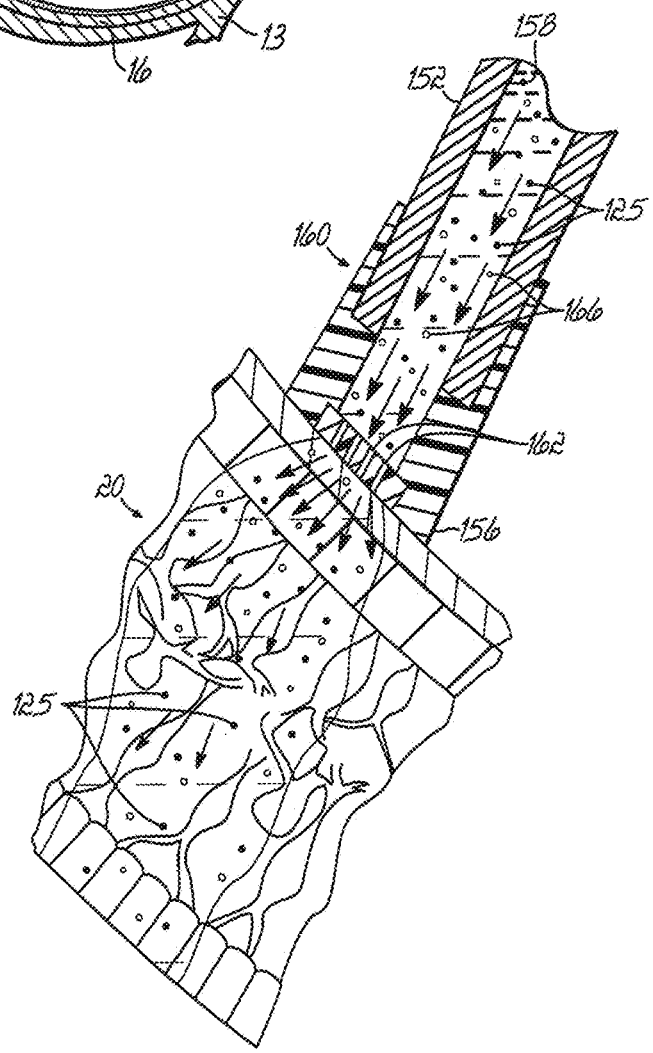
FIG. 4 is an enlarged diagrammatic illustration of the circled area 4 in FIG. 3 showing particles jetting from a cannula and dispersing throughout retinal structures.

As schematically shown in FIGS. 3 and 4, a device 150 for delivering the particles to the retina generally includes an elongated tube or cannula 152 having a proximal end 154 and a distal end 156 and an interior lumen 158 extending between the proximal and distal ends 154, 156. A distal end region 160, which may include a distal end face or a portion of the outer surface of the cannula 152 adjacent the distal end 156, includes a plurality of outlet ports or apertures 162 in fluid communication with the interior lumen 158. The device 150 further includes a pressure control source 164, such as for example a fan or pump, in fluid communication with the lumen 158 and operable for establishing an elevated pressure within the lumen. As known to one skilled in the art, the pressure should be sufficient to effectively disseminate the particles throughout the retina through a spraying or jetting action, but not sufficient to substantially damage retinal tissue. In one embodiment, a pressure may range from 0.0001 psi to 100 psi. The pressurized spraying also assists in distributing particles that disseminate and localize throughout the retinal layers. Localization of the particles permits enhanced control, duration, ease, etc. of stimulating these particles, resulting in enhanced control and effect.

The particles are introduced into the interior lumen 158 from any source, such as from a reservoir chamber, a syringe, etc. (not shown), and are mixed with a carrier fluid 166 such as a biocompatible gas or liquid. As non-limiting examples, air, oxygen, nitrogen, sulfur hexafluoride other perfluorocarbon fluids, etc., alone or in combination, may be used.

The pressurized fluid carrying the particles is regulated for ejection from the outlet ports, and is propelled toward the retina. The diameter of the outlet ports and pressure of the fluid are such as to allow the particles to penetrate the retinal tissue with minimal or no retinal damage. To accomplish a wide distribution of the particles throughout the retinal layers, the pressure may be pulsed to vary the penetration depth of the particles. The cannula may also be rotated or moved to spray or cover a larger area of the retina. Those of ordinary skill in the art will recognize other ways to distribute the particles throughout the retinal layers. As one example, the diameter of the outlet ports may be varied to provide different penetration depths. The outlet port diameters may range from about 0.01 mm to about 1 mm. As another example, the angles of the outlet ports may be varied to provide different spray patterns.

The above-described device may be used in the inventive method to deliver particles to the retina and distribute them substantially throughout the retinal layers, both intracellularly and/or intercellularly. That is, the particles diffusively locate and penetrate the retinal layers.

In one embodiment, an ocular surgeon may remove the vitreous gel, such as by an aspiration probe having vacuum pressure or a cutting probe, and replacing the contents of the vitreous cavity with saline, air, or another biocompatible fluid to facilitate particle penetration. The spraying device is inserted through the incision and into the vitreous cavity. The distal end of the device is positioned on or adjacent the retina, with the surgeon verifying placement using an operating microscope, a slit lamp, or other methods known in the art. Once the distal end of the device is adequately positioned, the pressurized fluid stream carrying the particles is generated and the particles are propelled toward the retina so as to distribute the particles throughout the retinal layers, as previously described. A gas probe may also be inserted into the vitreous cavity, such as by a second incision, to maintain the desired intraocular pressure. In another embodiment, the vitreous gel is not removed and the particles are injected (e.g., using a needle or other type of injection device) without spraying close to the retina, where the particles then diffuse through intercellular spaces of the retina and throughout the eye. Those of ordinary skill in the art will recognize that while the delivery method has been described as using separate aspiration probes, fiber optic probes, and gas probes, a single device that accomplishes delivery of the particles to the retina, removal of the vitreous gel and gas delivery may be used in the inventive method.

Once located at the desired location, the particles are stimulated using an energy source. The energy source may be located external to the eye at either or both the front and back, external to the retina, or on the surface of the retina. Because the retina is transparent, light is able to pass through and hence activate the particles located on and in various retinal tissues, as is subsequently described. The activated particles reset or influence the plasma membrane electrical potential of excitable cells, resulting in a desired change in membrane polarity. As previously described, this may take the form of normalized polarization, repolarization, enhanced polarization (i.e., stimulation), or reduced polarization (i.e., calming), etc.

In one embodiment, the particles are delivered into the eye when the vitreous gel is removed and replaced with saline and the internal limiting membrane (ILM) is removed. In one embodiment, the internal limiting membrane is removed to permit particle dissemination within the retina and throughout retinal intracellular spaces. This enhances diffusion of particles in the retina so that, by fluid flow, particles can then disseminate and penetrate retinal layers. Particles may adhere to the outer cellular membrane and/or may enter retinal cells. The particle size and/or spraying pressure, location, formulation may be altered to aid in selectivity. Particle penetration may be limited by the external limiting membrane (ELM), which may act as a semi-barrier to retinal transport. Excess particles may be removed as a part of the normal phagocytosis process (e.g., by glial cells). Ganglial cells in the eye, responsible for visual processing (discerning motion, depth, fine shapes, textures, colors), have less active phagocytosis mechanisms, so treatment of these cells may be affected by spraying to minimize excess distribution of particles.

Repolarization of cell membranes in a first location may have beneficial effects on polarization of cell membranes in second and subsequent locations. Due to propagation of electrical stimuli, a wave of electrical distribution is disseminated throughout the retina, for example, along a glial cell network. Because the glial cells assist in maintaining electrical balance, propagation also stabilizes polarization of adjacent cells.

It will be appreciated from the above description that stimulation of the entire retina may be achieved, rather than stimulation of a portion of the retina in proximity to a fixed electrode. This achieves substantially uniform repolarization, minimizing or preventing areas of hyper- and/or hypo-polarization, which assist in functional regeneration of glial cells.

In one embodiment, an ocular surgeon may stimulate the particles with an external light source, by ambient light, by ultrasound radiation, or by other mechanisms known to one skilled in the art. The particles facilitate, enhance, or boost a biological cell's regulation of its polarity, with adjacent cells capable of being stimulated due to the glial stimulus-propagating network.

It will be appreciated that nanoparticles are not limited to the previously described quantum dots and nanotubes, and include other carbon-based skeletal-type structures. Examples of such structures encompassed by nanoparticles and/or nanostructures include, but are not limited to, fullerenes, bucky balls, micelle-like structures such as micellar nanoparticles (MNP), lipid-based liposomes, dendrimers, and single-stranded deoxyribonucleic acid- or ribonucleic acid-oligonucleotide aptamer-conjugated or modified nanoparticles.

In one embodiment of the inventive method, such nanoparticles function as carriers and deliver a variety of opsin gene families. Opsin family genes include rhodopsin, halorhodopsin, photopsin, and channelrhodopsin. As known in the art, such gene families can integrate into the cell nucleus and nucleolus. The opsin gene families can be delivered alone, or in combination with one or more other genes to correct a genetic defect of excitable cells, or to induce an action potential in a membrane of excitable cells. Excitable cells include retinal cells, cells of the central nervous system (CNS) or peripheral nervous system (PNS). Stimulation may be directly or indirect, and may be by an external light source or a fiber optic. The method may also be used to stimulate cells that are normally non-excitable, e.g., stem cells including pluripotent mesenchymal stem cells, fibroblasts, glial cells, etc. Other desired gene stimulators, e.g., promotors, or gene silencers, e.g., siRNA, may also be included to up- or down-regulate gene function.

In this embodiment, the nanoparticles are rendered biocompatible, or their biocompatibility is enhanced, by being coated or associated with biocompatible molecules. As known in the art, these biocompatible molecules include, e.g., biotin-streptavadin, (poly)ethylene glycol (PEG), acetyl cysteine, cell penetrating peptide (CPP), arginine-CPP, cysteine-CPP, etc.

In one embodiment, the method is performed on a patient having a condition where excitable cells are partially or completely lacking function, and the method provides delivery of rhodopsin or other opsin-family gene members and stimulates excitable cells. In one embodiment, the method is performed on a patient where it would be beneficial to stimulate cells that are normally non-excitable, and the method provides delivery of rhodopsin or other opsin-family gene members and stimulates such cells that are normally non-excitable.

In one embodiment, the method is performed on a patient having a condition involving a defective gene, and where the condition is in a relatively early stage, amenable to therapy by the inventive method. The method results in stimulation of cells and prolongation of a regenerative process. The method may permanently repair the condition when the defective gene is included with the nanoparticle containing the opsin-family gene.

The nanoparticle-gene(s) composition may be administered intraocularly by intravitreal, intraretinal, subretinal, or other site of injection. The nanoparticle-gene(s) composition may be administered intrathecally into the cerebrospinal fluid, brain, or spinal cord. Intrathecal injection protects the gene(s) that otherwise may be damaged by contact with fluid and/or cellular blood components. The nanoparticle-gene(s) composition may be injected in any location, e.g., heart, peripheral nerves, etc., with a small gauge insulated metallic needle connected to a battery to carry electricity in the tissue for electroporation delivery inside the desired cells. Other types of force may also be simultaneously applied to enhance cell penetration of the nanoparticle. These embodiments facilitate penetration of the nanoparticle-gene(s) complex into cells. Subsequent stimulation of the cells is achieved using a fiber optic to stimulate nerves, cardiac muscle, skeletal muscle, etc. replacing electrical stimulation with light stimulation using a diode laser.

The nanoparticles may further be encapsulated to protect their contents. As only one non-limiting example, the dendrimer poly(amidoamine) (PAMAM) can be functionalized to be biocompatible and cell penetrating. Other dendrimers are poly(amidoamine-organosilicon) (PAMAMOS), poly (propyleneimine) (PPIO), tecto, multilingual, chiral, hybrid, amphiphilic, micellar, multiple antipen peptide, and Frechet-type dendrimers. Dendrimers have been proposed as carriers of luciferase gene, but there are no reports using or suggesting their use to transfer opsin gene family members, activated by light and producing an action potential on cells. The nanoparticles may be rendered visible, e.g., by combining them with other nanostructures such as functionalized quantum dots.

Fullerenes and buckyballs are nano-sized three dimensional carbon molecules having hollow spherical, oval, or tubular structures. Dendrimers are highly symmetrical nano-sized spherical compounds composed of branched polymers that have many functional groups on their outer surface. They are made with variable functionality, thermal stability or solubility, and are commercially available or synthesized as known in the art.

The nanoparticles have a small size of up to about 1 nm. The combined nanoparticle-gene(s) complex may likewise have a small size or up to 3 nm to 800 nm or more, as long as they are able to pass through intracellular spaces of the retina or CNS.

In one embodiment, administration of the inventive method into stem cells causes cellular multiplication upon light stimulation, with the stem cells becoming activated after light pulse exposure. Stem cells thusly treated migrate to the light source where they grow and replace cellular loss in a tissue. This embodiment could be used for therapy in pathologies such as, e.g., age related macular degeneration, and in organs such as heart, spinal cord, or brain. Light is delivered to the desired site using a fiber optic. In this way, damage due to stroke, infarct, is repaired.

In one embodiment, nanoparticles include all particles having a size ranging from of <1 nm to <1 micron. These include, but may not be limited to, quantum dots, dendrimers, fullerenes (buckyballs), liposomes, microspheres, lipids, and/or combinations thereof.

The nanoparticles may be synthetic, organic (e.g., liposomes), non-organic, non-magnetic, magnetic, paramagnetic, diamagnetic, supramagnetic, non-magnetic, mesoporous carbide-derived carbon, iron oxide nanoparticles with gold, graphene oxide and mesoporous silicone nanostructures, carbon, quantum dots, nanoshells, nanorods, nanotubes, nanowires, quantum dots, etc. Illustrative and non-limiting specific examples also include liposomal nanoparticles, liposome-PEG nanoparticles, micellar polymeric platform nanoparticles, L-adenine nanoparticles, L-lysine nanoparticles, PEG-deaminase nanoparticles, polycyclodextrin nanoparticles, polyglutamate nanoparticles, calcium phosphate nanoparticles, antibody-enzyme conjugated nanoparticles, polymeric lipid hybrid nanoparticles, nanoparticles containing a combination of two-three elements such as gold, gold-iron oxide, iron-zinc oxide, metallic nanoparticles, polylacticglycolic acid nanoparticles, ceramic nanoparticles, silica nanoparticles, silica cross-linked block polymer micelles, albumin-based nanoparticles, albumin-PEG nanoparticles, dendrimer attached magnetic or non-magnetic nanoparticles, etc.

In one embodiment, the nanoparticles may be incorporated within liposomes and/or plasmids carrying DNA, RNA, siRNA, medications, etc.

In one embodiment, the nanoparticles may of any shape, e.g., spheres, nanotubes, nanowires, tetragons, hexagons, cylinders, etc.

In one embodiment, the nanoparticles are coated with PEG, PEI, chitosan, biotin, streptavidin, CPP, ACPP etc. along with the specific cell membrane antibodies that can be tested by enzyme linked immunoassay (ELISA) to attach to the cell receptors.

In one embodiment using nanoparticles for gene transfer, a plasmid containing a gene (e.g., rhodopsin, holorodopsin, etc.) is attached to the nanoparticles during the coating process with PEG, chitosan, etc. along with CPP or ACPP. Nanoparticles generally may have improved tolerance in vivo compared to quantum dots. In this embodiment, use of magnetic nanoparticles is desirable for gene transfer because a magnetic field increases the transfection in tissue. In this embodiment, magnetic nanoparticles are administered along with a localized magnet. The electrostatic potential of these nanoparticles can be as high as −25 mV, encouraging further cell membrane penetration. While magnetic nanoparticles may be desirable for some embodiments, non-magnetic nanoparticles and organic nanoparticles can also be used with plasmids for transfection.

In one embodiment using nanoparticles for gene transfer, a liposome containing a gene (e.g., rhodopsin, holorodopsin, etc.) is used, forming a nanoparticle-liposome-gene complex. Liposomes as a carrier for the nanoparticle and gene are then coated and conjugated with the antibody prior to administration to the patient. Methods of preparing liposomes are known in the art, e.g., Akbarzadeh at al., Nanoscale Res. Lett. 8 (2013) 102, which is expressly incorporated herein by reference in its entirety.

In one embodiment, the nanoparticles are used for the transfection of cells, employing a plasmid attached to the labeled nanoparticles/genes that are stimulated by light to affect membrane channels of the cell membrane, regulating the membrane potential of the cells or inducing an action potential or a signal that can be transmitted to another cell or neuron. Examples include, but are not limited to, opsin family genes or similar G-proteins, a group of light sensitive membrane bound G-protein-coupled receptors converting a light pulse or other signals outside the cell to an electrochemical signal, e.g. rhodopsin, holorodpsin, etc. The opsins family consists of Go opsins and Go opsins found in vertebrates or Gq opsins, photoisomerases, and neuropsins. The plasmids are used to transfer the gene-conjugated nanoparticles inside the cell. The plasmids are conjugated or entrapped during the coating process of nanoparticles with the compounds previously described, i.e., PEG, PEI, chitosan, biotin, streptavidin, CPP, ACPP etc. along with the specific cell membrane antibodies.

In one embodiment, the plasmid nanoparticles/genes are administrated systemically or along with other stimulatory or inhibitory medications, locally, e.g. in the eye, central nervous system, peripheral nerves, heart, etc.

In one embodiment when the nanoparticles/genes are injected in the eye or in the CNS fluid naked DNA, RNA, etc. conjugates are not damaged by serine proteases during the process of administration because of the existence of the blood brain and blood ocular barrier, preventing free serum access to these organs.

In one embodiment, the plasmid nanoparticles may be administered through the nasal mucosal by spraying, drops, or injection to access the olfactory nerves. The nanoparticles are picked up by olfactory nerve cells through which they travel to brain affecting the desired brain area. Thus, brain stimulation can be performed by the patient deliberately after nasal nanoparticle administration to affect various disease such as epilepsy, mood, PTSD, depression, fright, Parkinsons disease, Alzheimers disease, and other brain degenerative diseases, or after trauma or stroke, in migraines, addiction, etc.

The plasmid nanoparticles/gene can be admitted to the tissue culture of any cell. They are picked up by the cells having membrane receptors to the nanoparticles antibodies. These cells can be in the body or in the tissue culture. Examples of such cells include, but are not limited to, neuronal, retinal, muscle, or any kind or stem cells e. g. skin, neurons, mesenchymal, fibroblast, mucosal stem cells of the eye, glial cells, endothelial cells. These stem cells can be injected in the circulation, in the CNS or its fluid, eye, under the retina, spinal cord, peripheral nerves through the skin, through the nasal mucosa, in any other organ. The transfected cells or the organ can be directly stimulated by light of any wavelength, e.g. external environment, by diode laser, ultrasound, etc. Stimulation can be performed via a processor as a light pulse (from a diode laser etc.) applied to the transfected organ e.g. brain, eye, spinal cord, peripheral nerves, the heart as a pacemaker using a fiber optic implanted in the organ, or applied externally for superficially located nerves, or the retina through the cornea or directly through the sclera or, as previously described, to the brain through the nasal mucosa, etc. The number of pulses or their duration can be also controlled and/or predetermined by the processor. In one embodiment, application of light pulses to the transfected cells causes them to multiply and increase in number in vivo or in vitro. The number of stem cells can be increased in cells carrying nanoparticles. The stimulating light pulse creates an electrical potential inside the cell that stimulates cell growth and multiplication of the stem cells and their growth in vivo or in vitro, as is known with electrical pulse stimulation. The result is a significant contribution to the number of stem cells needed in vivo to repair damaged tissue. Such an embodiment is useful in therapy for, e.g., vascular occlusion in the retina, spinal cord, brain, and heart leading to strokes or infarcts. Such an embodiment is also useful in therapy for various diseases in the extremities or other degenerative diseases such as Alzeheimer's disease, Parkinson's disease, traumatic brain injury, spinal cord injury, etc.

In one embodiment, one uses magnetic nanoparticles to increase transfection of the cells. When administered in the circulation, eye, CNS, peripheral nerves, heart, etc., a magnet is applied to generate a magnetic field and attract the nanoparticles. The magnet can be a natural magnet or an electromagnet. It is positioned at the desired location of an organ where the intended cell transfection should take place e. g. over the sclera behind the retina, frontal, parietal, posterior cortex, heart, spinal cord, peripheral nerves, nose, etc. The nanoparticles accumulate over a period of time in the organ and transfect the cells. The electrostatic potential of these nanoparticles can be as high as −25 mV, encouraging further the cell membrane penetration.

In one embodiment, these plasmid nanoparticles/genes transfer the gene or genes in the predetermined cells. They are picked up by the cells having membrane receptors to the nanoparticle antibodies. After transfecting the cells, the nanoparticles can be degraded or expelled from the cells, taken up by reticuloendothelial cells, eliminated through the bile, urine, sweat, etc.

The transfected cells are stimulated by light of any wavelength from ultraviolet to infra red and other wave lengths, or by mechanical force, ultrasound, etc., to change the membrane potential of the cell and achieve normalization of the membrane potential or an action potential.

In one embodiment, biomolecules including genes are transferred to the nucleus using inorganic and/or organic solar cell nanoparticles, including hybrids, as subsequently explained, using gene editing by programmable directed nucleases to result in patient therapy. As is appreciated by those skilled in the art, therapy includes any reduction in or amelioration of pathological effects, including but not limited to curing the patient of the pathology. In this embodiment, these nucleases bind to and cut DNA that matches guide RNAs in regions containing clustered regularly interspersed palindromic repeats (CRISPR). Cas9, the CRISPR associated protein 9, is an RNA-guided DNA endonuclease associated with the CRISPR complex. The endonuclease and/or the CRISPR/Cas9 complex, upon cell entry, seek DNA containing a target sequence, e.g., a specific mutation in the mitochondria or the nucleus. The cleavage functions of the endonuclease and/or CRISPR/Cas9 complex destroy the disease-producing DNA by excising it or replacing it with an un-mutated, i.e., normal DNA segment, as known in the art to treat the patient. The nuclease cleaves host DNA at the target site. With one cut, CRISPR can insert a new customized gene sequence; with two cuts, two CRISPRs can excise the DNA, providing the host with a new DNA. The mechanism of action of the CRISPR/cas9 complex and its ability to target and edit genes is known in the art, e.g., Sander and Joung, CRISPR-Cas systems for editing, regulating and targeting genomes. Nature Biotechnology 32 (2014) 347-355 which is expressly incorporated by reference herein.

Briefly, and as previously disclosed in greater detail, inorganic solar cell type nanoparticles include the following. Graphene quantum dots, graphene-oxide quantum dots, graphene-zinc oxide quantum dots, graphene nanotubes, carbon nanotubes, and/or non-quantum dot nanoparticles; these may be non-magnetic, magnetic, paramagnetic, diamagnetic, supramagnetic, non-magnetic, mesoporous carbide-derived carbon, iron oxide nanoparticles with gold, graphene oxide, mesoporous silicone nanostructures, nanoshells, nanorods, nanotubes, nanowires, etc. Organic solar cell type nanoparticles include the following. Fullerenes, buckyballs, dendrimers, liposomes, aptamers, and/or micelles. Specific types include, e.g., dendrimers including poly(amidoamine) (PAMAM), poly(amidoamine-organosilicon) (PAMAMOS), poly(propyleneimine) (PPIO), tecto, multilingual, chiral, hybrid, amphiphilic, micellar, multiple antipen peptide, and Frechet-type dendrimers. Hybrid quantum dots include the following. Graphene/zinc oxide (ZnO) and reduced graphene oxide, plasmonic nanoparticles coated with reduced graphene oxide, and dextran-reduced graphene oxide. Exemplary non-limiting examples include liposome-PEG nanoparticles, micellar polymeric platform nanoparticles, L-adenine nanoparticles, L-lysine nanoparticles, PEG-deaminase nanoparticles, polycyclodextrin nanoparticles, polyglutamate nanoparticles, calcium phosphate nanoparticles, antibody-enzyme conjugated nanoparticles, polymeric lipid hybrid nanoparticles, nanoparticles containing a combination of two-three elements such as gold, gold-iron oxide, iron-zinc oxide, metallic nanoparticles, polylacticglycolic acid nanoparticles, ceramic nanoparticles, silica nanoparticles, silica crosslinked block polymer micelles, albumin-based nanoparticles, albumin-PEG nanoparticles, dendrimer attached magnetic or non-magnetic nanoparticles, etc.

Solar cell nano- and/or micro-particles are three dimensional semiconductor devices using light or ultrasound energy to generate electrical energy to provide a photovoltaic effect. In embodiments, the particle material may be ceramic, plastic, silicon; particles of crystalline silicon may be monocrystalline cells, poly or multicrystalline cells, ribbon silicon having a multicrystalline structure, nanocrystals of synthetic silicon, gallium/arsenide, cadmium/selenium, copper/indium/gallium/selenide, zinc sulfide, indium/gallium/phosphide, gallium arsenide, indium/gallium nitride, a nanocrystal, such as cadmium/selenium (Cd/Se) and a metal, e.g., a CdSe/Au nanometer-sized composite particle as previously described, particles of a variety of semiconductor/metal and semiconductor/semiconductor hetero-junctions, e.g., particles based upon semiconductor/metal hetero-junctions between group II-VI, IV, III-V, IV-VI, referring to groups of the periodic table, metal-oxide, or organic semiconductors and a metal, and in particular those based upon Si/Au, GaAs/Au, InAs/Au, and PbS/Au hetero-junctions. The quantum dots and/or semiconductor nanowires may also be biocompatible short peptides of naturally occurring amino acids that have the optical and electronic properties of semiconductor nano-crystals, e.g., short peptides of phenylalanine. The particles can consist of both inorganic or organic materials, as previously described.

Any of the particles may be coated with biocompatible mono- or bilayers of phospholipid a protein, a peptide polyethylene glycol (PEG) that can be used as a scaffold to aid in biocompatibility of the particle. The particles can be entirely or partially biodegradable. Particles may also be included in/coated on a bioabsorbable, or non-bioabsorbable but biocompatible, polymer fiber, tube, or other two- or three-dimensional structure. Therapeutic stimulation of the polymer and adjacent tissue may stimulate and/or inhibit cell excitation, depending upon the wavelength of the applied light and the character of the associated particles, with differing parts of the polymer, e.g., the front and back sides of a substantially two-dimensional structure, having different particles to exert different effects upon target and adjacent cells.

As previously disclosed, all the above embodiments use compounds that are collectively termed nanoparticles. Nanoplatforms may be developed, as previously described.

The nanoparticles that are coated, targeted, functionalized, and conjugated with opsin and/or other genes, replace the defective cell's gene, using enolase and/or CRISPR technology both of which are known in the art. As previously described, the nanoparticle can be functionalized to render or enhance its biocompatibility, and can be further treated or delivered to enhance cell penetration. The nanoparticles can comprise an enolase or CRISPR complex, and/or a G-protein and/or opsin-family gene, and an antibody that targets the nanoparticles to a cell and coated with a biocompatible molecule for cell uptake, forming a complex that is activated with an energy source. To enhance biocompatibility, association with or covalent coupling to one or more of cell penetrating peptides (CPP), arginine-CPP, cysteine-CPP, polyethylene glycol (PEG), biotin-streptavadin, acetyl cysteine, an antibody, and/or a ligand for a receptor may be employed. As an example, nanoparticles can be functionalized and/or linked to vectors using (poly) ethylene glycol (PEG) moieties, with the number of PEGS varied depending on various factors, such as the need to enhanced hydrophilicity, the protein size, etc. The vector and nanoparticle are combined in the presence of at least one biocompatible adjuvant, suspension agent, surfactant, etc. Particles may be coated with or linked to, e.g., folate, polydopamine, etc. so that these molecules are targeted intracellularly, extracellularly, to a cell membrane, to a specific cellular site or organelle, etc. The nanoparticles may further be encapsulated to protect their contents, e.g., the dendrimer poly(amidoamine) (PAMAM) can be functionalized to be biocompatible and cell penetrating. Other dendrimers are poly(amidoamine-organosilicon) (PAMAMOS), poly(propyleneimine) (PPIO), tecto, multilingual, chiral, hybrid, amphiphilic, micellar, multiple antipen peptide, and Frechet-type dendrimers.

In one embodiment, the nanoparticles, such as a semiconductor-metal particle, can be coated such that the nanoparticle is amphiphilic, where a portion of the nanoparticle is rendered hydrophilic and another portion of the nanoparticle is rendered hydrophobic. In one embodiment, and using a CdSe/Au particle as an example, the CdSe/Au particles are covered by trioctylphosphine oxide and alkylphosphonic acid, both of which are hydrophobic. Surface functionalization covers the Au portion of the CdSe/Au particles with polyethylene glycol, making them hydrophilic; the CdSe portion, still covered by trioctylphosphine oxide and alkyl phosphonic acid, remains hydrophobic. In one embodiment, CdSe/Au particles are suspended in N,N-dimethylformamide containing detergent (e.g., 1% Triton X-100) and exposed to polyethylene glycol-$(CH_2)_{10}$—SH to coordinate the thiol to the Au end. The nanoparticles may be coated with biocompatible mono- or bilayers of phospholipid a protein, a peptide polyethylene glycol (PEG) that can be used as a scaffold to aid in biocompatibility of the particle. The particles can be entirely or partially biodegradable. The particles may also be included in or coated on a bioabsorbable or non-bioabsorbable but biocompatible polymer structured or configured as a fiber, a tube, a substantially two-dimensional structure, or a three-dimensional structure to fit any anatomical or physiological site. The coated polymer structure may be any desirable length or size to maintain its position with respect to a tissue structure. The therapeutic stimulation of the polymer and adjacent tissue may stimulate and/or inhibit the excitation of cells depending upon the wavelength of the applied light and the character of the one or more types of particles associated with it, with differing parts of the polymer, e.g., the front and back sides of a substantially two-dimensional structure, having different particles in order to have different effects upon the target cells adjoining those parts. The nanoparticles may be coated with or linked to, e.g., folate, polydopamine, etc. so that these molecules are targeted intracellularly, extracellularly, to a cell membrane, to a specific cellular site or organelle, etc. The nanoparticles may be coated with a thermosensitive polymer, e.g., chitosan, PEG, etc. Application of an external energy source results in a slight increase in temperature, e.g., to about 39° C. to about 43° C. in one embodiment, to about 40° C. to about 42° C. in another embodiment, that facilitates release of the biomolecule from the thermosensitive nanoparticles or quantum dot. The nanoparticles can be made to respond to various wavelengths of light (visible and invisible). In one embodiment they are coated with organic molecules. In one embodiment, they are completely organic. In one embodiment, they are PEGylated to last longer. In one embodiment, they are coated to be attracted to certain receptors or stay only on the cell surface.

This system is programmed by a processor to define the frequency and the duration of the emitted light pulses.

All nanoparticles that are coated/targeted can be injected locally, in a body cavity or systemically, to treat various diseases.

In one embodiment one administers systemically, in a body cavity, or locally, a plurality of nanoparticles, which can include quantum dots, or plasmonic nanoparticles. The nanoparticles may be magnetic, paramagnetic, nonmagnetic, metallic, non-metallic, organic, inorganic, synthetic, piezoelectric, nanobots, lanthanide, cerium, gold, zinc, silver, silicone, perovskite; or liposomes, dendrimers, nanotubes, nanowires, caged nanoparticles, nanoshells, etc. The nanoparticles may be coated with a biocompatible polymer such as biotin, streptavidin, PEG, cell penetration peptide (CPP), arginine CPP, etc., known in the art. The nanoparticles may be conjugated with antibodies or aptamers for cell targeting.

In one embodiment, the method delivers to the cells nanoparticle-gene conjugates with opsin family genes to simultaneously stimulate the cells by light and to modify a pathology-inducing cellular DNA, either nuclear or mitochondrial DNA, with an endonuclease or a CRISPR/Cas9 conjugated with the nanoparticles. Once inside the cell, the endonuclease or CRISPR/Cas9 seeks the mitochondria or the nucleus, containing a specific DNA mutation, and destroys this disease producing DNA by excision and/or replacement with a normal DNA segment, or adding an opsin gene and/or other required genes, as known in the art.

In one embodiment, the method delivers locally or systemically nanoparticle stimulating genes, such as opsin family genes, conjugated with the CRISPR/cas9 complex to repair or replace a defective gene in the nucleus or mitochondria of retinal cells, CNS neuronal/glial cells, spinal cord cells, peripheral nerve cells, or cardiac cells.

In one embodiment, the method administers a plurality of biocompatible or biodegradable nanoparticles conjugated with opsin family genes and a CRISPR/cas9 complex systemically or locally to an intraocular site, CNS, proximate or adjacent peripheral nerves, in the heart, etc. Once the CRISPR/cas9 DNA enters the cell, it transcribes its DNA into a nuclease which scans the host DNA for a target sequence. The nuclease cuts the host DNA at the target. With one cut, the CRISPR can insert a new custom-made gene sequence; with two cuts, two CRISPRS can excise the DNA, and providing the host with a new DNA, as known in the art.

In one embodiment, the method administers nanoparticles conjugated with an opsin gene along with enolase, alpha, beta, gamma etc., or CRISPR/cas9 DNA while delivering an additional gene and growth factors to the stimulating gene, such as an opsin gene etc. to the retina, CNS, spinal cord, peripheral nerves, or heart of a patient in need of such therapy.

In another embodiment, the method administers targeted nanoparticle conjugated genes systemically or locally by injection. Local injection may be, e.g., in the eye, vitreous cavity, brain ventricles, over or inside the brain, in the CSF, in the heart, close to peripheral nerves. This embodiment of the method provides therapy to degenerative diseases such as retinal degeneration, other retinal diseases, Alzheimer's disease, Parkinson's disease, stroke, spinal cord injuries, peripheral nerve injuries, etc. to stimulate neuronal function and growth or to treat cardiac arrhythmias or dysrhythmias.

In one embodiment, the method administers a plurality of coated nanoparticle conjugated gene and CRISPER/cas9 to modify a genetic defect of stem cells, using in vitro tissue culture to manipulate the DNA of the patient's locally harvested stem cells prior to administration to the patient. The stem cells may be, e.g., conjunctival limbal stem cells, heart stem cell, brain stem cell, spinal cord nerve stem cells, mesenchymal or ectodermal cells, etc.

In one embodiment, the method administers targeted piezoelectric nanoparticles either systemically or locally. The targeted piezoelectric nanoparticles can be controlled remotely by an ultrasound probe with an "off" switch to wirelessly stimulate the piezoelectric nanoparticles and produce an electrical current created by a wireless electrical stimulation of cells inside the body, changing the membrane potential/action potential of cells in contact with the piezoelectric nanoparticles.

In one embodiment, the method administers targeted coated piezoelectric nanoparticles conjugated with genes by routes including, e.g., submucosal injection, and spraying the nasal mucosa. In this embodiment, the nanoparticles travel through the olfactory nerves to various areas of the brain that can be stimulated with an externally applied ultrasound over the nose by a patient as needed e.g. in epilepsy, migraine, depression, Parkinson's disease, Alzheimer's disease, restless leg syndrome, etc.

In one embodiment, the method administers biodegradable targeted nanoparticles, conjugated with appropriate stimulatory and regenerative genes, by direct injection into an excitable organ having a brain blood barrier, thus without being degraded by serum enzymes, to be incorporated into those various excitable organs.

In one embodiment, the method systemically or locally delivers to cells an opsin gene with targeted nanoparticles using an implanted small diode having piezoelectric electric nanoparticles acting as an "on"/"off" switch of the battery supplying electricity to the diode laser. An externally located ultrasonic probe controls the piezoelectric nanoparticles, which stablishes the electric current for the diode laser, producing wireless switchable "on"/"off" laser light pulses for stimulating cells containing an opsin family gene or channel rhodopsin.

In one embodiment, the method uses a plurality of targeted nanoparticles along with biocompatible polymer-coated piezoelectric nanoparticles. Such biocompatible polymer-coated piezoelectric nanoparticles include zirconate titanate, perovskite-based, oxides, barium titanate, polyvinylidene fluoride (PVDF), etc. They are delivered systemically or locally, e.g., to the brain, spinal cord, peripheral nerves, retina, heart, etc. to stimulate the piezoelectric nanoparticles with extra-corporal ultrasound. The stimulation initiates an electric "on"/"off" response from the piezoelectric nanoparticles, which is transmitted to adjacent cells and modifies cellular membrane potential, resulting in hyperpolarization, hypopolarization, depolarization, or an action potential.

In one embodiment, the method uses a ribbon of piezoelectric nanoparticles attached to an "on"/"off" switch of a small implantable battery of a small diode. This system can initiate an "on"/"off" light laser response from the diode laser. Upon ultrasound activation, an electrical current is created in the piezoelectric nanoparticles that leads to the diode laser's battery, thus controlling activation of the diode laser light production. This initiates an "on"/"off" action potential in the membrane of excitable cells, depending on the frequency and duration of the electrical pulse.

In one embodiment of the method, piezoelectric nanoparticles are administered with nanoparticles conjugated with an opsin gene, and an implantable battery of a diode laser controllable by a programmable processor from a remote ultrasonic probe to remotely controllably stimulate laser light production and, in turn, excitable cells. The diode laser can be implanted external or internal to the skull, adjacent to an organ, adjacent to sympathetic or parasympathetic ganglions cells, adjacent to the brain, heart, eye, spinal cord, sympathetic or parasympathetic ganglion cells, peripheral nerves, etc. The system creates a remotely controlled ultrasonic "on"/"off" switch to indirectly remotely stimulate, by diode light, light-sensitive cells with the diose laser and, in turn, controlling organ function. For example, it may be used to control peripheral nerves to repair a paresis or paralysis, spastic muscles numbness, in nerve injuries, in the eye, in CNS degenerative diseases, epilepsy, depression, dementia, Alzheimer's disease, Parkinson's disease, spinal cord injury, peripheral nerve injury, etc.

Each reference previously disclosed and disclosed below is expressed incorporated by reference herein in its entirety:

Bakalova et al. Quantum Dot-Conjugated Hybridization Probes for Preliminary Screening of siRNA Sequences. J. Am. Chem. Soc. 127 (2005) 11328-11335.

Biju et al., Chem. Soc. Rev. 39 (2010) 3031

Derfus et al. Targeted Quantum Dot Conjugates for siRNA Delivery. Bioconjugate Chem. 18 (2007) 1391-1396.

Deisseroth, Optogenetics, Nature Methods, published online Dec. 20, 2010, available at http://www.stanford.edu/group/dlab/papers/deisserothnature2010.pdf.

Dixit et al. Quantum Dot Encapsulation in Viral Capsids. Nano Letters, 6 (2006) 1993-1999.

Ebenstein et al. Combining atomic force and fluorescence microscopy for analysis of quantum-dot labeled protein-DNA complexes. J. Molecular Recognition, 22 (2009) 397-402.

Gill et al. Fluorescence Resonance Energy Transfer in CdSe/ZnS-DNA Conjugates: Probing Hybridization and DNA Cleavage. J. Phys. Chem. B, 109 (2005) 23715-23719.

Huang et al. Intermolecular and Intramolecular Quencher Based Quantum Dot Nanoprobes for Multiplexed Detection of Endonuclease Activity and Inhibition. Anal. Chem. 83 (2011) 8913-8918.

Joo et al. Enhanced Real-Time Monitoring of Adeno-Associated Virus Trafficking by Virus-Quantum Dot Conjugates. ACS Nano 5 (2011) 3523-3525.

Lim et al. Specific Nucleic Acid Detection Using Photophysical Properties of Quantum Dot Probes. Anal. Chem. 82 (YEAR) 886-891.

Mossman, Quantum dots track who gets into cell nucleus. Physorg.com, Sep. 2, 2010 http://www.physorg.com/news202628740.html Sarkar et al. Doped Semiconductor Nanocrystals and Organic Dyes: An Efficient and Greener FRET System J. Phys. Chem. Lett. 1 (2010) 636-640.

Suzuki et al. Quantum Dot FRET Biosensors that Respond to pH, to Proteolytic or Nucleolytic Cleavage, to DNA Synthesis, or to a Multiplexing Combination. J. American Chemical Society 130 (2008) 5720-5725.

Wang et al. Nucleic Acid Conjugated Nanomaterials for Enhanced Molecular Recognition. ACS Nano 3 (2009) 2451-2460.

You et al. Incorporation of quantum dots on virus in polycationic solution. Int. J. Nanomedicine 1 (2006) 59-64.

Audero et al. Sporadic Autonomic Dysregulation and Death Associated with Excessive Serotonin Autoinhibition. Science 321 (2008) 130-133.

De Crespigny et al. Magnetic Resonance Imaging Assessment of Cerebral Hemodynamics During Spreading Depression in Rats. Journal of Cerebral Blood Flow and Metabolism 18 (1998) 1008-1017.

Höhne et al. Acetazolamide prevents hypoxic pulmonary vasoconstriction in conscious dogs. J. Appl. Physiol. 97 (2004) 515-521.

Rio-Portilla et al., REM Sleep POST-EYE Movement Activation, Int' J. Bioelectromagnetism 10 (2008) 192-208.

U.S. Pat. No. 8,324,344

Other variations or embodiments of the invention will also be apparent to one of ordinary skill in the art from the above description. As one example, the inventive technology, in the absence of a viral vector, finds use in plants, animals, and/or cell cultures along with a marker gene, such as GFP, to indicate that the cell, organ, plant, fruit, etc. are genetically modified. As one example, other forms, routes, and sites of administration are contemplated. As another example, the invention may be used in patients who have experienced ocular trauma, retinal degeneration, ischemia, inflammation, etc. As another example, the particles may include sensing devices for qualitative and/or quantitative chemistry or other determinations. For example, the particles may include sensors or other detection means for glucose, oxygen, glycosylated hemoglobin, proteins including but limited to enzymes, pressure, indicators for retinal degenerative disease, etc. Thus, the forgoing embodiments are not to be construed as limiting the scope of this invention.

What is claimed is:

1. A method for at least one of editing or regulating a gene in a target excitable cell, the method comprising
   administering to a patient in need thereof a plurality of nanoparticles coated with a biocompatible molecule for cell uptake, the nanoparticles conjugated with at least one opsin family gene, a second unmutated gene other than the opsin family gene which ameliorates a genetic or acquired degenerative disease or condition, an antibody that targets the nanoparticles to the target excitable cell, and a CRISPR/cas9 complex to form a complex of coated nanoparticle-gene-CRISPR/cas9;
   delivering the nanoparticle-gene-CRISPR/cas9 complex to the target cell using the nanoparticle of the complex as a carrier without using a viral vector, and stimulating the complex and the target excitable cell with one or more energy sources under conditions sufficient to introduce the at least one opsin-family gene, the second gene, and the CRISPR/cas9 complex into the target excitable cell;
   using the CRISPR/cas9 complex to excise from the DNA of the target excitable cell a DNA segment bearing a mutation inducing the genetic or acquired degenerative disorder or condition; and
   replacing the excised mutated DNA segment with the second unmutated gene to treat the patient;
   wherein stimulating the complex and the target excitable cell with one or more energy sources includes stimulating the nanoparticle of the complex and the target excitable cell with light.

2. The method of claim 1, wherein the DNA of the target excitable cell is selected from the group consisting of nuclear DNA and mitochondrial DNA.

3. The method of claim 1 where the excitable cell is selected from the group consisting of a retinal cell, a central nervous system neuronal cell, a central nervous system glial cell, a spinal cord cell, a peripheral nerve cell, a cardiac cell, and combinations thereof.

4. The method of claim 1 where the complex is administered systemically or locally.

5. The method of claim 1 where the complex is administered to a site selected from the group consisting of intraocular, intravitreal, intrathecal, brain ventricle, proximate a central nervous system neuron, proximate a peripheral nerve, or intracardiac.

6. The method of claim 1, where the nanoparticles include piezoelectric nanoparticles and the stimulating step further includes remotely controlling the piezoelectric nanoparticles to wirelessly stimulate the piezoelectric nanoparticles and produce an electrical current resulting in wirelessly altering the membrane or action potential of the target excitable cell in contact with the piezoelectric nanoparticles.

7. The method of claim 6, where wirelessly altering the membrane or action potential results in a response selected from the group consisting of hyperpolarization, hypopolarization, and depolarization.

8. The method of claim 6, where remotely controlling the piezoelectric nanoparticles is via an ultrasound probe.

9. The method of claim 6 where the piezoelectric nanoparticles are administered by a route selected from the group consisting of injecting submucosally, spraying the nasal mucosa, and combinations thereof, where the piezoelectric nanoparticles travel through olfactory nerves to the brain that is stimulated with an externally applied ultrasound over the nose by the patient as needed.

10. The method of claim 1 where the nanoparticles include piezoelectric nanoparticles and the stimulating step further includes remotely controlling the piezoelectric nanoparticles to wirelessly stimulate the piezoelectric nanoparticles and control a diode laser surgically implanted in the patient to produce laser light for stimulating the target excitable cell with the at least one opsin-family gene, and the piezoelectric nanoparticles act as an "on"/"off" switch of a battery supplying electricity to the diode laser.

11. The method of claim 10 where stimulation is controlled by a programmable processor of an extra-corporal ultrasonic probe wirelessly controlled by the diode laser.

12. The method of claim 10 where the diode laser is surgically implanted at a site selected from the group consisting of external to the skull, internal to the skull, adjacent to an organ, adjacent to sympathetic ganglion cells, adjacent to parasympathetic ganglion cells, adjacent to the brain, adjacent to the heart, adjacent to an eye, adjacent to the spinal cord, adjacent to peripheral nerves, and combinations thereof.

13. The method of claim 6 where the piezoelectric nanoparticles are rendered biocompatible by coating with a compound selected from the group consisting of zirconate titanate, perovskite-based, oxides, barium titanate, polyvinylidene fluoride (PVDF), and combinations thereof.

14. The method of claim 11 where a ribbon of piezoelectric nanoparticles is attached to the battery of the diode laser that, upon ultrasound stimulation, creates a pulsating electrical current in the piezoelectric nanoparticles attached to the battery of the diode laser, thus controlling activation of the diode laser light production and initiating an "on"/"off" action potential in the membrane of excitable cells depending on the frequency and duration of the electrical pulse.

15. The method of claim 1 where the light stimulating the nanoparticle of the nanoparticle-gene-CRISPR/cas9 complex is delivered by a fiber optic.

16. The method of claim 1, wherein stimulating the complex and the target excitable cell with light further comprises stimulating both the nanoparticle of the complex and the opsin expressed by the target excitable cell with a particular wavelength of light to produce a complementary effect that results in an enhanced action potential in the target excitable cell.

17. A method for at least one of editing or regulating a gene in a target excitable cell, the method comprising administering to a patient in need thereof a plurality of nanoparticles coated with a biocompatible molecule for cell uptake, the nanoparticles conjugated with at least one opsin-family gene, a second unmutated gene other than the opsin family gene which ameliorates a genetic or acquired degenerative or condition, an antibody that targets the nanoparticles to the target excitable cell, and a CRISPR/cas9 complex to form a complex of coated nanoparticle-gene-CRISPR/cas9, the nanoparticles including piezoelectric nanoparticles;

delivering the nanoparticle-gene-CRISPR/cas9 complex to the target excitable cell using the nanoparticle of the complex as a carrier without using a viral vector and stimulating the complex and the target excitable cell with an energy source under conditions sufficient to introduce the at least one opsin-family gene, the second unmutated gene, and the CRISPR/cas9 complex into the target excitable cell; and using the CRISPR/cas9 complex to excise a DNA segment bearing a mutation inducing the genetic or acquired degenerative or condition from the target excitable cell; and replacing the excised mutated DNA segment with the second unmutated gene to treat the patient;

wherein stimulating the complex and the target excitable cell further comprises remotely controlling the piezoelectric nanoparticles with an ultrasound probe to wirelessly stimulate the piezoelectric nanoparticles and control a diode laser surgically implanted in the patient to produce laser light for stimulating the target excitable cell expressing the at least one opsin-family gene, the piezoelectric nanoparticles acting as an "on"/"off" switch of a battery supplying electricity to the diode laser, and wherein a ribbon of piezoelectric nanoparticles are attached to the battery of the diode laser that, upon ultrasound stimulation, creates a pulsating electrical current in the piezoelectric nanoparticles attached to the battery of the diode laser, thus controlling activation of the diode laser light production.

* * * * *